(12) United States Patent
Zhang et al.

(10) Patent No.: US 12,410,140 B2
(45) Date of Patent: Sep. 9, 2025

(54) METHOD FOR SYNTHESIS OF ROXADUSTAT AND INTERMEDIATE THEREOF, AND INTERMEDIATE THEREOF

(71) Applicant: JUMPCAN (SHANGHAI) MEDICAL TECHNOLOGY CO., LTD, Shanghai (CN)

(72) Inventors: Yong Zhang, Shanghai (CN); Guo Wang, Shanghai (CN); Fei Yang, Shanghai (CN); Fengwei Liu, Shanghai (CN); Chundong Zhou, Shanghai (CN); Zitong Zhang, Shanghai (CN)

(73) Assignee: JUMPCAN (SHANGHAI) MEDICAL TECHNOLOGY CO., LTD, Shanghai (CN)

( * ) Notice: Subject to any disclaimer, the term of this patent is extended or adjusted under 35 U.S.C. 154(b) by 519 days.

(21) Appl. No.: 17/913,488

(22) PCT Filed: Jun. 18, 2021

(86) PCT No.: PCT/CN2021/100797
§ 371 (c)(1),
(2) Date: Sep. 22, 2022

(87) PCT Pub. No.: WO2021/254469
PCT Pub. Date: Dec. 23, 2021

(65) Prior Publication Data
US 2024/0018109 A1    Jan. 18, 2024

(30) Foreign Application Priority Data

Jun. 19, 2020 (CN) .......................... 202010566080.2
Oct. 23, 2020 (CN) .......................... 202011148392.8

(51) Int. Cl.
C07D 217/26 (2006.01)
(52) U.S. Cl.
CPC ................... *C07D 217/26* (2013.01)
(58) Field of Classification Search
CPC ...................................................... C07D 217/26
See application file for complete search history.

(56) References Cited

U.S. PATENT DOCUMENTS

| | | | | |
|---|---|---|---|---|
| 9,174,976 | B2 * | 11/2015 | Arend .................... | C07D 417/12 |
| 9,371,288 | B2 * | 6/2016 | Witschi ................. | C07D 217/26 |
| 10,851,062 | B2 * | 12/2020 | Wang ..................... | C07D 217/26 |
| 2015/0031721 | A1 | 1/2015 | Kang et al. | |
| 2015/0175550 | A1 | 6/2015 | Thompson et al. | |
| 2016/0194285 | A1 | 7/2016 | Thompson et al. | |

FOREIGN PATENT DOCUMENTS

| | | |
|---|---|---|
| CN | 103435546 A | 12/2013 |
| CN | 104024227 A | 9/2014 |
| CN | 104892509 A | 9/2015 |
| CN | 108017583 A | 5/2018 |
| CN | 108341777 A | 7/2018 |
| EP | 305769 B1 | 9/1991 |
| EP | 3415502 A | 12/2018 |
| JP | 2015524409 A | 8/2015 |
| JP | 2019506441 A | 3/2019 |

OTHER PUBLICATIONS

Nov. 30, 2022 Chinese Decision of Final Rejection issued in Chinese Patent Application No. 2022102958575.
Sep. 3, 2021 International Search Report issued in International Patent Application No. PCT/CN2021/100797.
Sep. 3, 2021 Written Opinion of the International Searching Authority issued in International Patent Application No. PCT/CN2021/100797.
Feb. 21, 2022 Chinese First Office Action issued in Chinese Patent Application No. 2021106830326.
Jun. 1, 2022 Chinese Second Office Action issued in Chinese Patent Application No. 2021106830326.
Sep. 19, 2022 Chinese First Office Action issued in Chinese Patent Application No. 2022102958575.

(Continued)

*Primary Examiner* — D Margaret M Seaman
(74) *Attorney, Agent, or Firm* — Harness, Dickey & Pierce, P.L.C.

(57) ABSTRACT

Disclosed are a method for the synthesis of roxadustat and an intermediate thereof, and an intermediate thereof. In particular, disclosed is a method for the synthesis of compound M1, the method comprising the following steps: carrying out a reaction as shown below between compound SM and compound SM-A under the action of an oxidizing agent. The method of the present invention uses cheap and easily available raw materials, has short reaction steps, produces a high yield, has simple and convenient post-treatment procedures, and is suitable for industrial production.

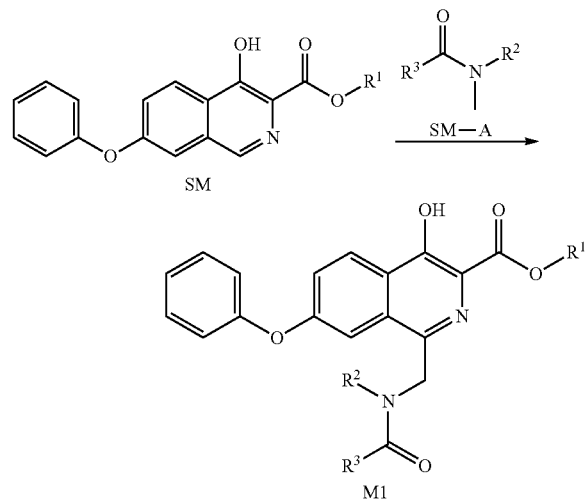

20 Claims, No Drawings

(56) References Cited

OTHER PUBLICATIONS

Nov. 9, 2022 Chinese First Office Action issued in Chinese Patent Application No. 2022108007925.

Zhang Qiwei, et al. "Preogress in the Synthesis of Roxadustat", Chinese Journal of Pharmaceuticals, 2019, 11, 50, 1239-1244, Nov. 30, 2019.

Okugawa, et al.—"Introduction of Quinolines and Isoquinolines onto Nonactivated a.C—H Bond of Tertiary Amides through a Radical Pathway"—J. Org. Chem., 2016, 1, 82, 170-178, Dec. 7, 2016.

Truscello, Ada M, et al.—"Revisiting the Minisci Reaction: New Mild Amidoalkylation of Benzo-Fused N-Heteroaromatic Bases under Metal-Free Conditions"—Org. Process Res. Dev., 2019, 7, 23, 1450-1457, Jun. 11, 2019.

Jun. 13, 2023 First Office Action issued in Japanese Patent Application No. 2022559397.

Zhang Qiwei et al., Chinese Journal of Pharmaceuticals, 2019,50(11), pp. 1239-1244.

\* cited by examiner

METHOD FOR SYNTHESIS OF ROXADUSTAT AND INTERMEDIATE THEREOF, AND INTERMEDIATE THEREOF

CROSS-REFERENCE TO RELATED APPLICATIONS

The present application is a U.S. National Phase Application under 35 U.S.C. 371 of International Application No. PCT/CN2021/100797, filed on Jun. 18, 2021, which claims the priorities of Chinese patent applications CN2020105660802 filed on Jun. 19, 2020 and CN2020111483928 filed on Oct. 23, 2020. The entire disclosures of the above applications are incorporated herein by reference in their entireties.

TECHNICAL FIELD

The present disclosure relates to a synthesis method of roxadustat and an intermediate thereof, and an intermediate thereof.

BACKGROUND

Roxadustat is a hypoxia inducible factor proline hydroxylase inhibitor (HIF-PHI), developed by FibroGen Company, USA, and Astellas and AstraZeneca have received authorized permission, and roxadustat has been marketed in China to treat anemia related to chronic kidney disease and end-stage kidney disease.

The chemical name of roxadustat is: N-[(4-hydroxy-1-methyl-7-phenoxy-3-isoquinoline)carbonyl)]glycine, and the structural formula is as follows:

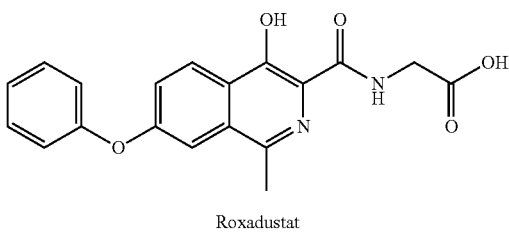 [SMILES: Cc1nc(C(=O)NCC(=O)O)c(O)c2ccc(Oc3ccccc3)cc12]

Roxadustat

The known synthetic routes of roxadustat are mainly as follows:

(1) CN201310302822.0 discloses a synthetic route of roxadustat. In this route, an intermediate 4-hydroxy-7-phenoxyisoquinoline-3-carboxylate was synthesized first, then reacted with tetramethylmethanediamine, and then reacted with acetic anhydride, completed a methylation reaction of 1-position of isoquinoline ring by using palladium/carbon hydrogenation to obtain a key intermediate 4-hydroxyl-1-methyl-7-phenoxyisoquinoline-3-carboxylate of roxadustat, and finally subjected to an ammonolysis reaction with glycine to obtain a final product. The route is as follows:

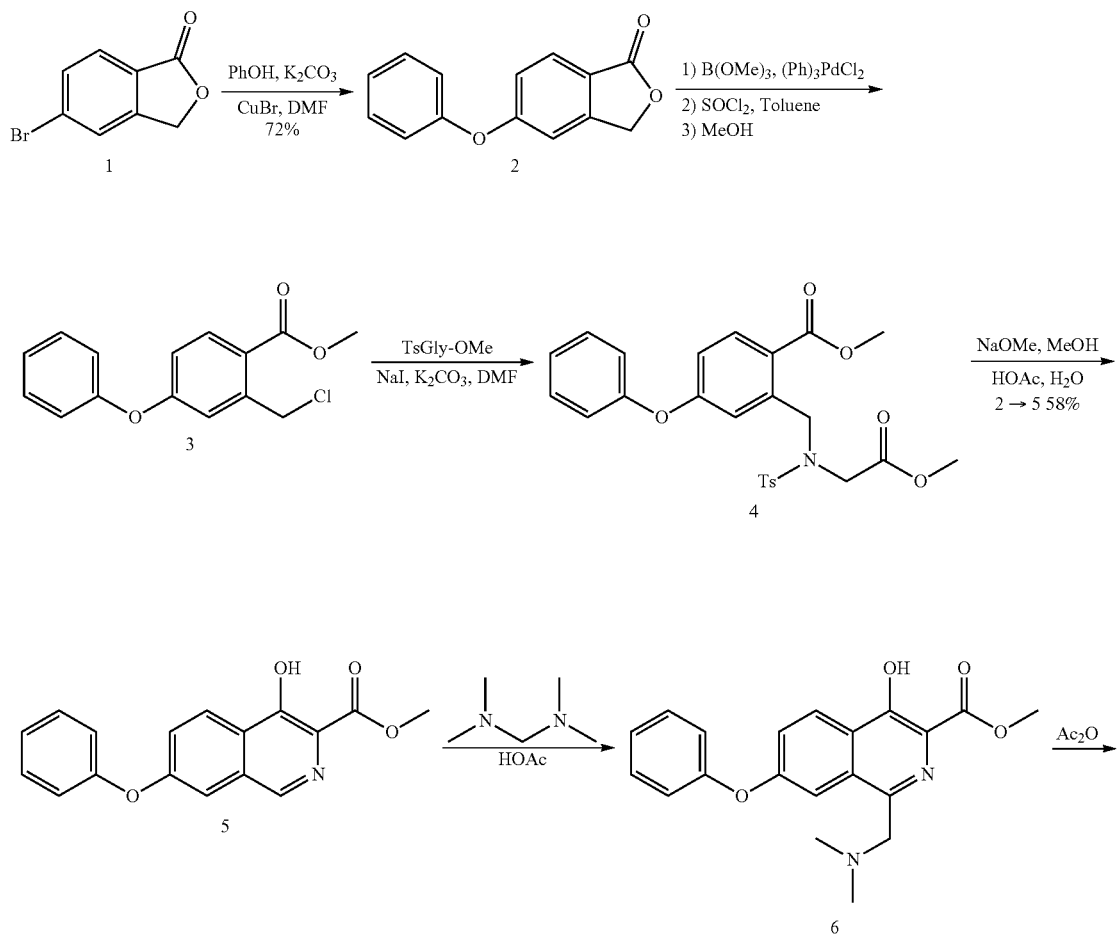

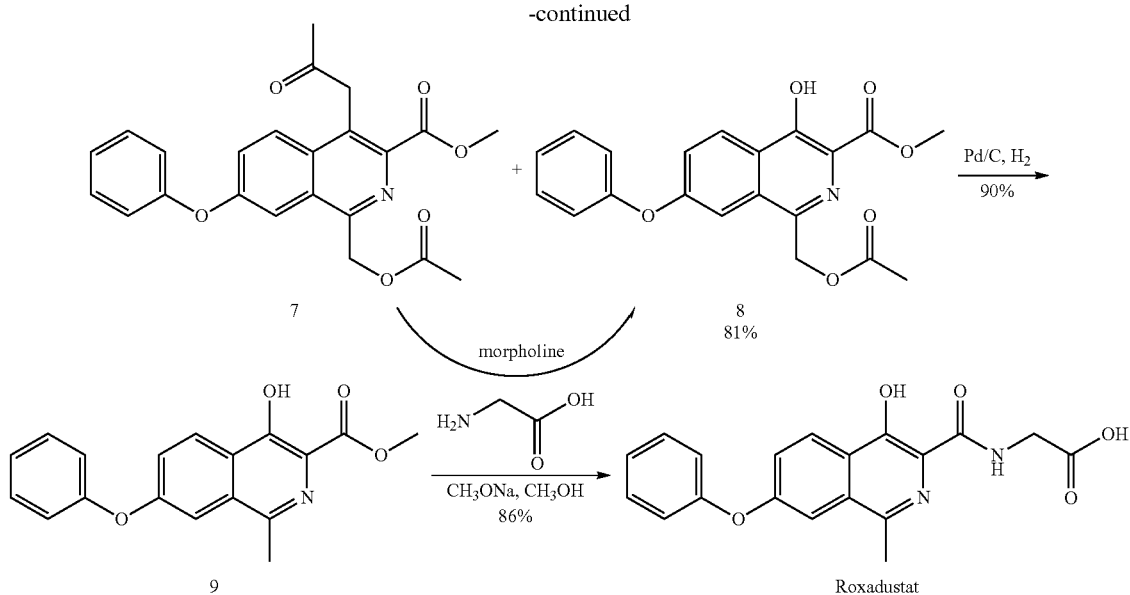

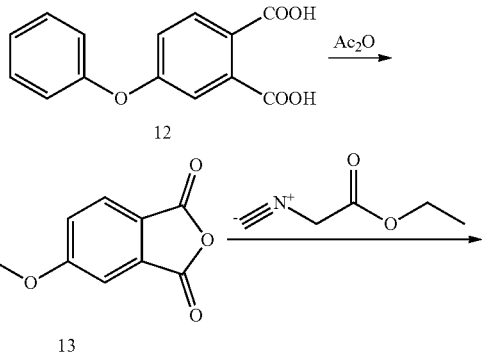

In this route, the reaction from intermediate 5 to intermediate 9 appears to be three steps. In fact, since a considerable by-product 7 is produced in a step of preparing intermediate 8 from intermediate 6, it is required to add an additional reaction step of converting intermediate 7 to intermediate 8 through morpholine, so it actually takes four steps to prepare intermediate 9. In addition, reagents such as acetic anhydride and morpholine with a high boiling point are used in this route, which are difficult to remove in a subsequent purification, and more impurities may be introduced in the removal process. In addition, the deacetylation of intermediate 8 to prepare intermediate 9 is catalyzed by noble metal palladium, and the price of palladium is higher, resulting in large consumption and high cost in industrial production.

(2) CN201280036322.0 discloses a synthetic route of roxadustat. In this route, 4-nitrophthalonitrile was used as a raw material, then reacted with ethyl isocyanatoacetate after etherification, hydrolysis, condensation, and then isoquinoline ring was obtained by cyclization under the action of an acid. Isoquinoline ring was chlorinated at position 1 by phosphorus oxychloride, then methylated, and finally condensed with glycine methyl ester and hydrolyzed to obtain roxadustat. The route is as follows:

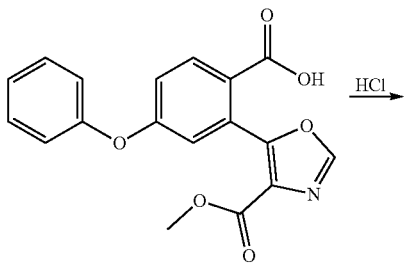

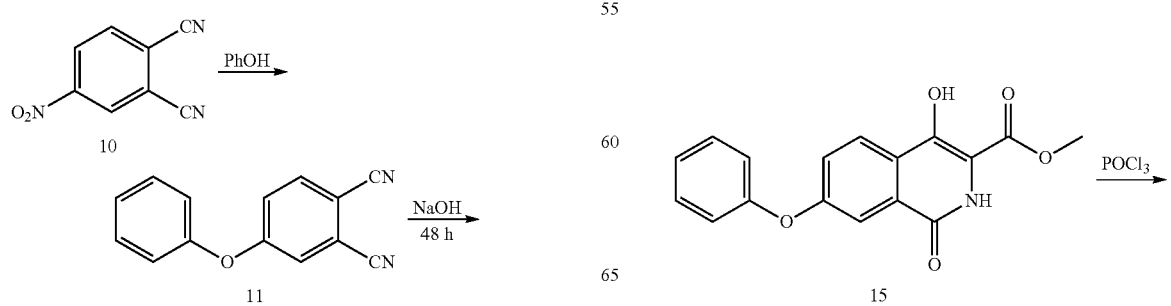

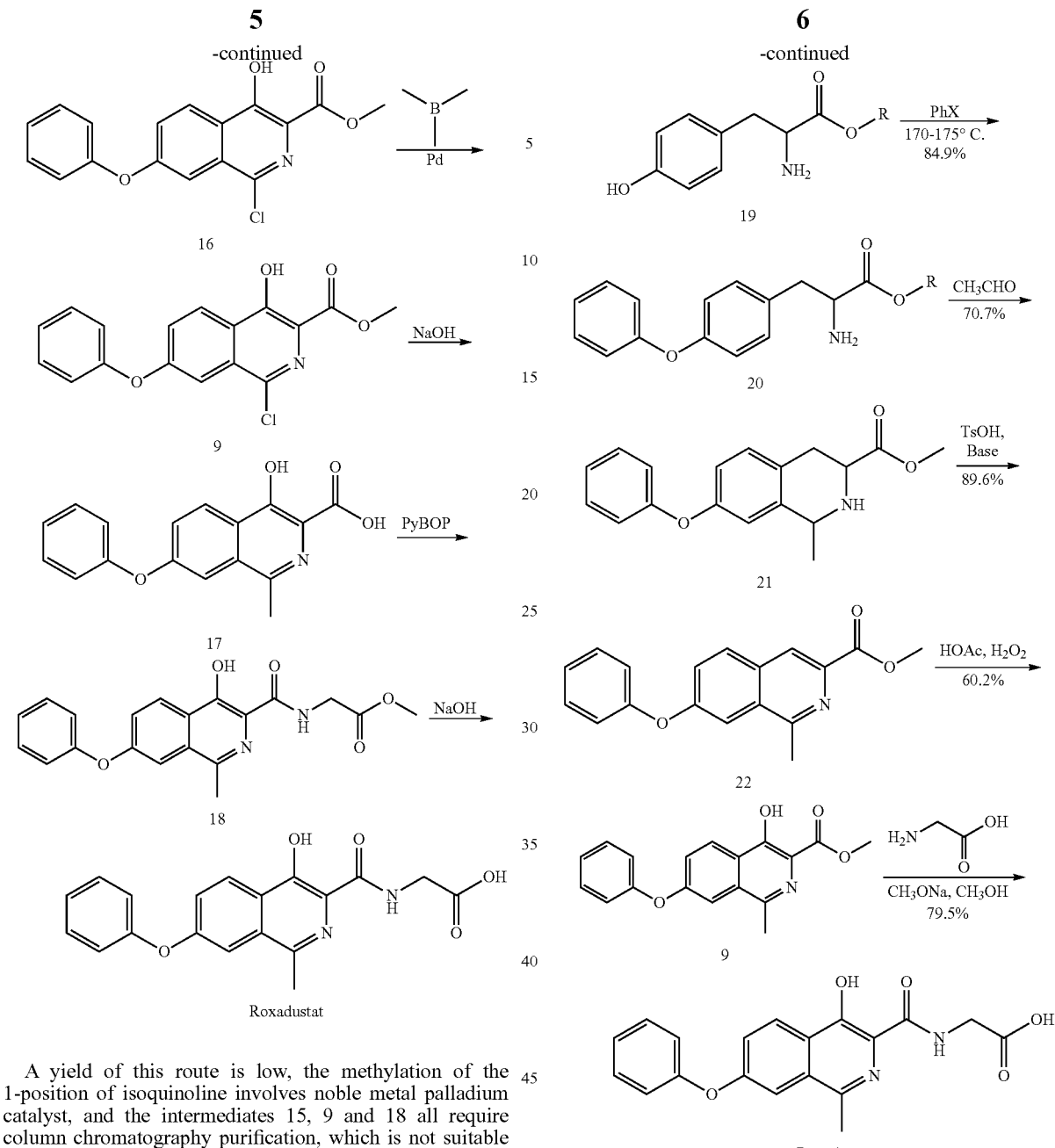

A yield of this route is low, the methylation of the 1-position of isoquinoline involves noble metal palladium catalyst, and the intermediates 15, 9 and 18 all require column chromatography purification, which is not suitable for large-scale industrial production.

(3) CN201510299804.0 discloses a synthetic route of roxadustat. In this route, tyrosine was used as a starting material, which was esterified, etherified, cyclized and dehydrogenated to obtain the isoquinoline ring, then oxidized and rearranged to obtain the key intermediate 4-hydroxyl-1-methyl-7-phenoxyisoquinoline-3-carboxylate, and finally acylated with glycine under the action of an acid-binding agent to obtain roxadustat. The route is as follows:

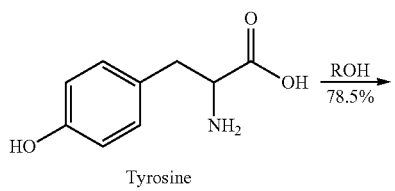

In this route, a high temperature of 170° C. to 175° C. is required when the intermediate 19 prepares the intermediate 20, which has a high energy consumption and is difficult to realize industrially. The use of hydrogen peroxide in the preparation of intermediate 9 from intermediate 22 has certain risks in industrial production.

(4) EP 305769 B1 discloses a synthetic route of roxadustat. In this route, methyl 2-bromo-4-fluorobenzoate was used as the starting material, etherified with phenol, cyclized with ethyl isocyanatoacetate, conducted a Heck reaction with ethylene butyl ether, and then cyclized under an acidic condition to form the isoquinoline ring, and finally acylated with glycine under the action of DBU to form roxadustat. The route is as follows:

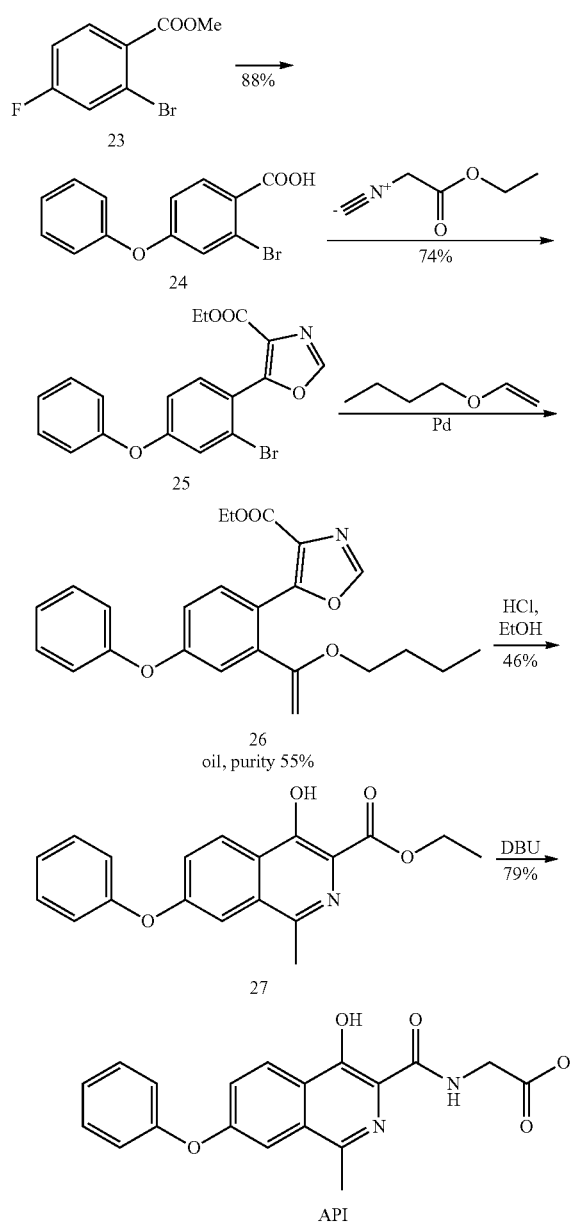

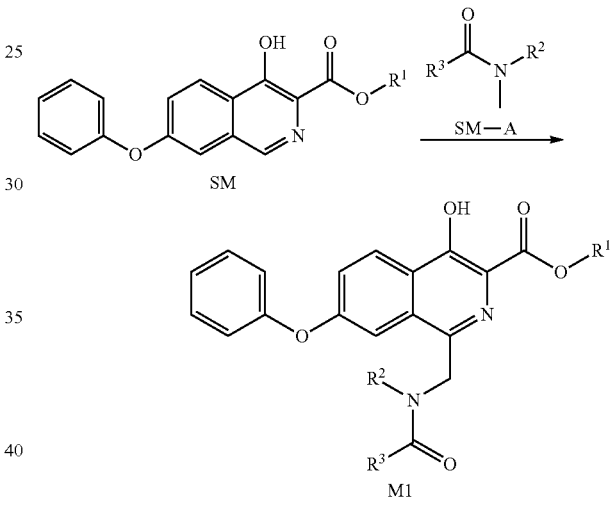

In this route, ethyl formate on an oxazole ring is easily decarboxylated when intermediate 24 prepares intermediate 25, and a yield of preparing key intermediate 27 is not high, and the Heck reaction requires the noble metal palladium catalysis, resulting in a higher overall cost of this route, which is not conducive to large-scale industrial production.

It can be seen that the known synthetic routes of roxadustat have the following defects: the steps are cumbersome, and additional reaction process for controlling by-products needs to be introduced; or high boiling point reagents which are difficult to remove and noble metal palladium catalysts are used; or the yield is low and column chromatography purification is required; or a high-temperature reaction is required, and the reagents used are dangerous, which makes the synthetic routes of roxadustat costly and is not conducive to industrial production. This situation needs to be solved urgently.

CONTENT OF THE PRESENT INVENTION

The technical problem to be solved by the present disclosure is to overcome the defects such as long steps, cumbersome operation, high cost and unfavorable industrial production in the synthetic routes of roxadustat in the prior art, and to provide a synthesis method of roxadustat and an intermediate thereof, and an intermediate thereof. The method of the present disclosure uses cheap and easily available raw materials, has short reaction steps and mild reaction conditions, has a high yield, has simple and convenient post-treatment procedures, and is suitable for industrial production.

The present disclosure solves the above technical problems through the following solutions.

The present disclosure provides a synthesis method of compound M1, and the method comprises the following steps: carrying out a reaction as shown below between compound SM and compound SM-A under the action of an oxidizing agent;

$R^1$ is H, $C_1$-$C_4$ alkyl or $C_6$-$C_{10}$ aryl;

$R^2$ is H or methyl;

$R^3$ is H, $C_1$-$C_4$ alkyl, $C_4$-$C_6$ cycloalkyl or $C_6$-$C_{10}$ aryl;

wherein, the $C_1$-$C_4$ alkyl, the $C_6$-$C_{10}$ aryl and the $C_4$-$C_6$ cycloalkyl are optionally substituted by 1, 2 or 3 R, and each R is independently halogen, hydroxyl, amino, $C_1$-$C_4$ alkyl, $C_1$-$C_4$ alkoxy, mono($C_1$-$C_4$ alkyl)amino, di($C_1$-$C_4$ alkyl)amino, cyano or nitro.

In the present disclosure, preferably, $R^1$ is H, $C_1$-$C_4$ alkyl or $C_6$-$C_{10}$ aryl; more preferably, $R^1$ is H, methyl, ethyl, n-propyl, isopropyl, n-butyl, isobutyl, sec-butyl, tert-butyl, phenyl or naphthyl; most preferably, $R^1$ is H, methyl or ethyl.

In the present disclosure, preferably, $R^3$ is H, $C_1$-$C_4$ alkyl, $C_4$-$C_6$ cycloalkyl or $C_6$-$C_{10}$ aryl; more preferably, $R^3$ is H, methyl, ethyl, n-propyl, isopropyl, n-butyl, isobutyl, sec-butyl, tert-butyl, cyclobutyl, cyclopentyl, cyclohexyl, phenyl or naphthyl; most preferably, $R^3$ is H or methyl.

According to the public content of the present disclosure, those skilled in the art know that when R exists, it should appear on a $R^1$ substituent of compound SM and/or a $R^3$ substituent of compound SM-A.

In an embodiment of the present disclosure, compound SM-A is
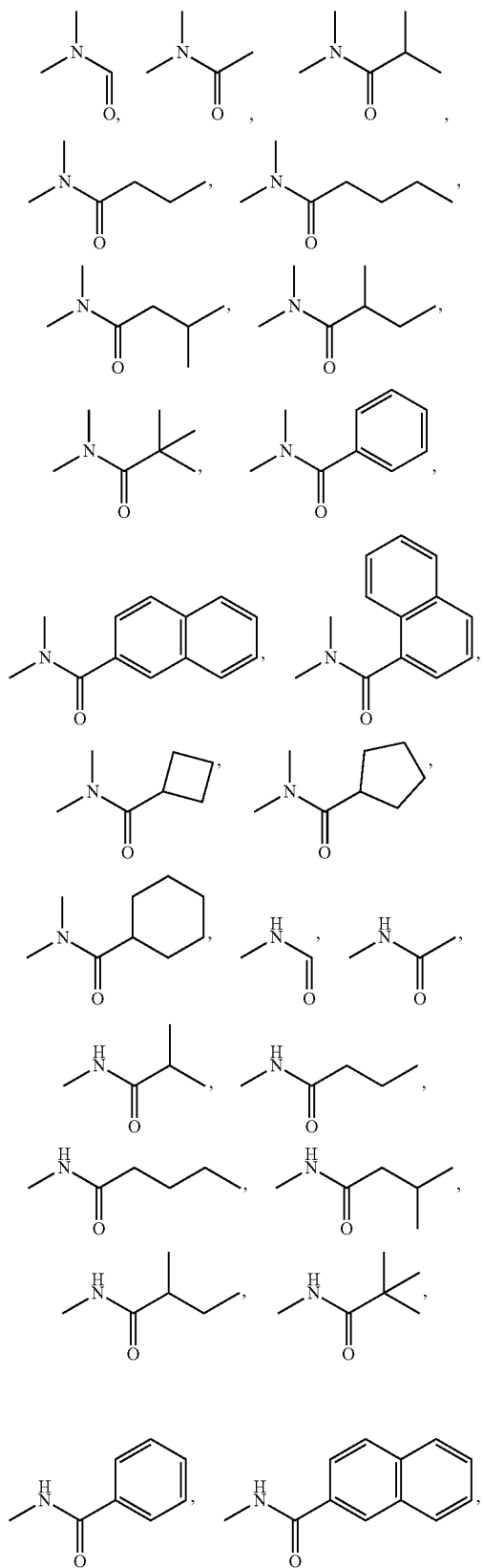
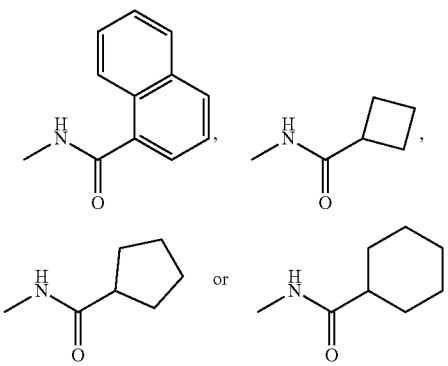
optionally substituted by 1, 2 or 3 R.
In an embodiment of the present disclosure, compound SM-A is preferably
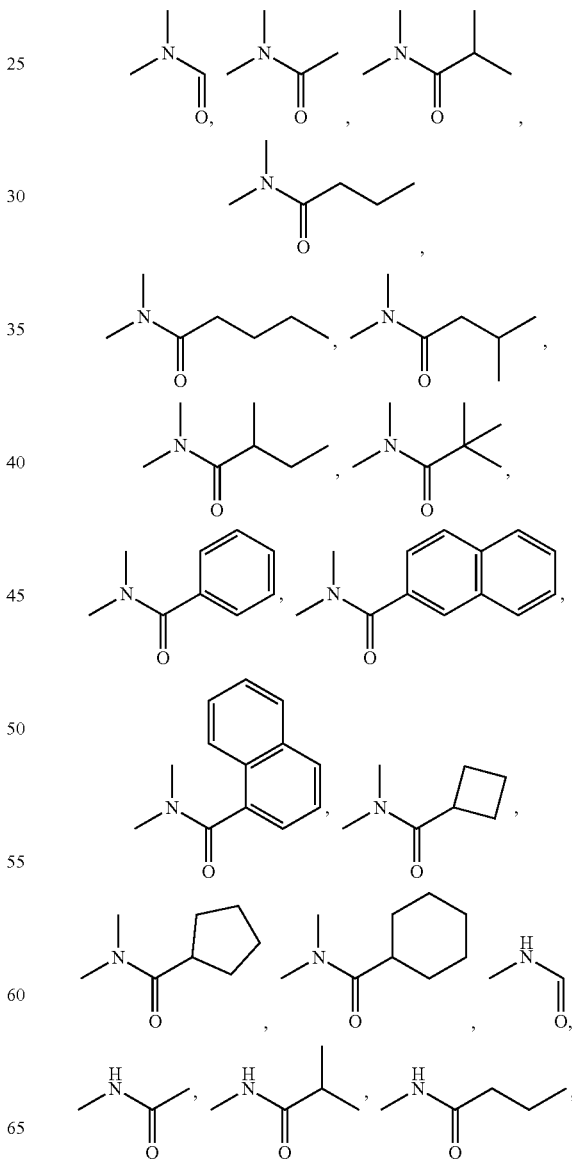

-continued
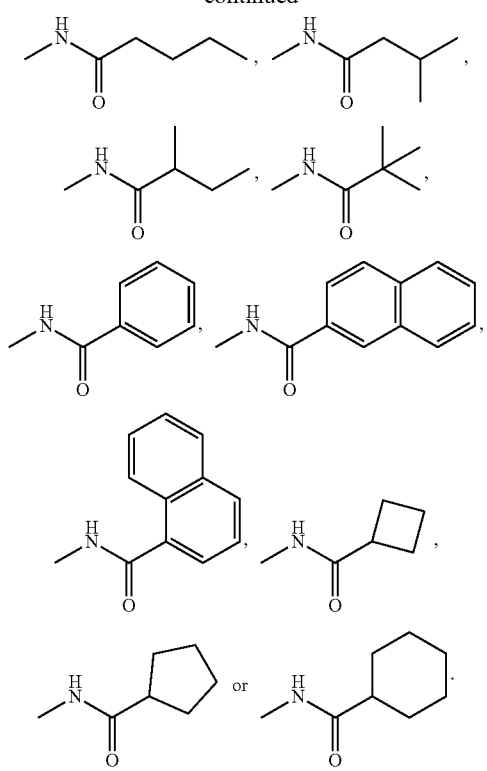
In an embodiment of the present disclosure, compound SM is preferably
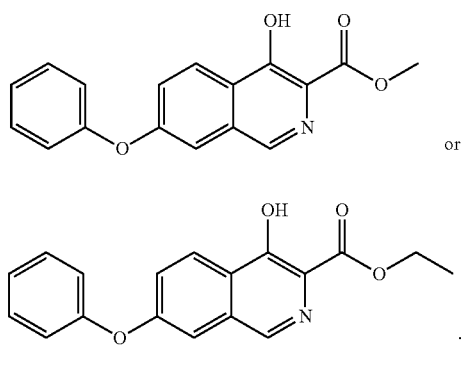
In an embodiment of the present disclosure, compound M1 may be
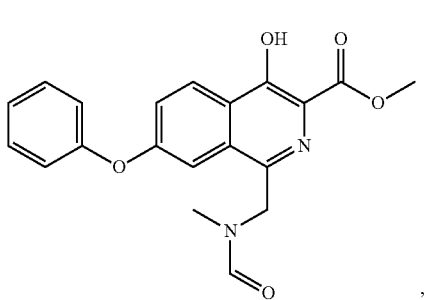
M1-1
-continued
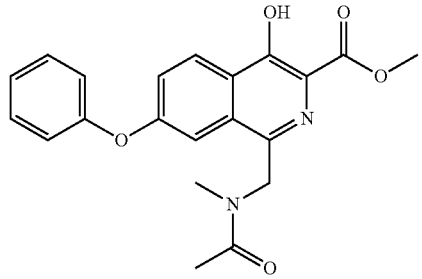
28
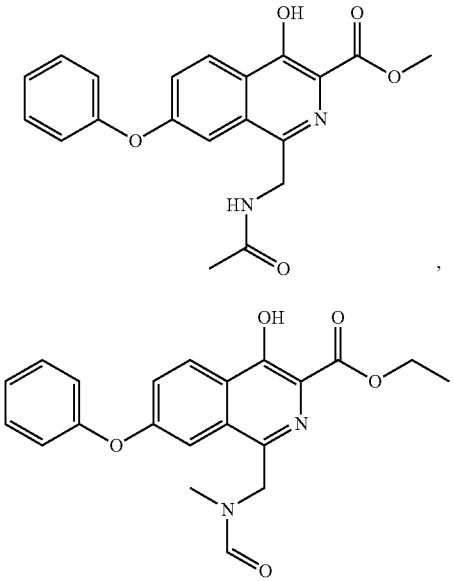
M1-2
M1-F
M1-A
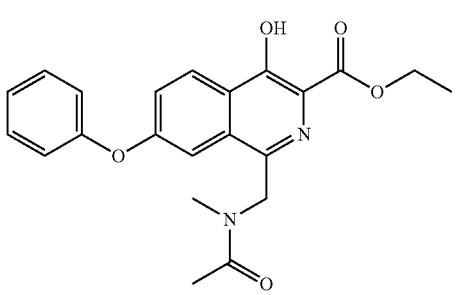
M1-C
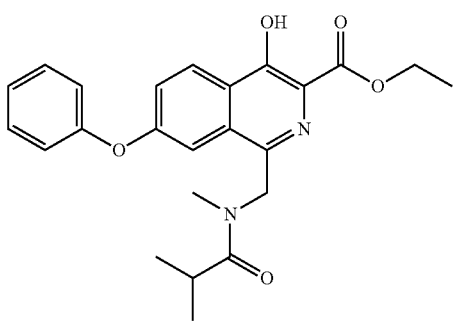

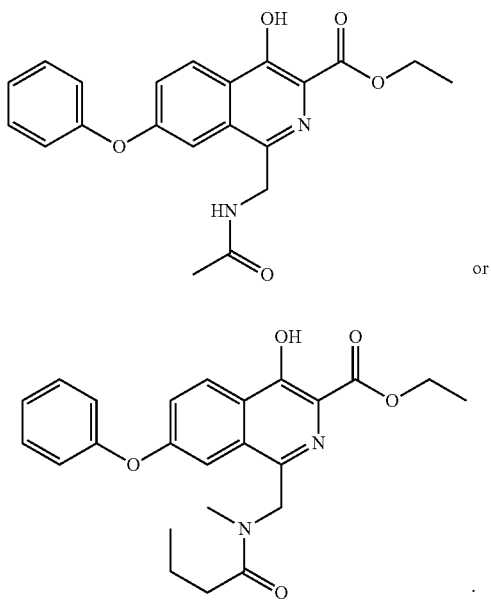

In the synthesis method of compound M1, the oxidizing agent may be a conventional oxidizing agent for such reactions in the art. In the present disclosure, the oxidizing agent may be, for example, a persulfate oxidizing agent, a peroxide oxidizing agent or a mixture thereof. Herein, the persulfate oxidizing agent may be, for example, alkali metal persulfate, alkaline earth metal persulfate or a mixture thereof. The alkali metal persulfate may be sodium persulfate, potassium persulfate, potassium peroxymonosulfate composite salt (Oxone) or a mixture thereof. The alkaline earth metal persulfate may be magnesium persulfate. The peroxide oxidizing agent generally refers to a compound containing peroxy —O—O—. In the present disclosure, the peroxide oxidizing agent may be, for example, $R'''$—O—O—$R''$; wherein $R'''$ and $R''$ are independently H, $C_1$-$C_4$ alkyl or benzoyl optionally substituted by 1, 2 or 3 halogens. The peroxide oxidizing agent may be, for example, hydrogen peroxide ($H_2O_2$), peracetic acid, peroxytrifluoroacetic acid, BPO (benzoyl peroxide), TBHP (tert-butyl hydroperoxide), DTBP (di-tert-butyl peroxide) or a mixture thereof.

In the synthesis method of compound M1, the amount of the oxidizing agent may be a conventional amount of the oxidizing agent for such reactions in the art. In the present disclosure, a molar ratio of the compound SM to the oxidizing agent is 1:1-1:5, for example, 1:1.5-1:3, for another example, 1:2.

In the synthesis method of compound M1, the amount of the compound SM and the compound SM-A may be the conventional amount for such reactions in the art. In the present disclosure, a molar ratio of the compound SM-A to the compound SM may be greater than 1:1, for example, greater than 5:1, greater than 10:1, greater than 20:1, greater than 40:1, or greater than 50:1. In principle, in order to control the cost, those skilled in the art know that the amount of the compound SM-A should be controlled within an appropriate range.

In the synthesis method of compound M1, when the compound SM-A is a liquid, the compound SM-A serves as a reaction raw material and a solvent simultaneously. When the compound SM-A is a solid, the compound SM-A only serves as the reaction raw material. At this time, the synthesis of compound M1 carries out the reaction in the presence of a solvent. The solvent may be a conventional solvent for such reactions in the art, such as a chlorinated hydrocarbon solvent, an ether solvent or a mixture thereof. The solvent generally has good solubility for compound SM, and is not easily oxidized or does not participate in the reaction. Therefore, the solvent may be, for example, dichloromethane, tetrahydrofuran, dioxane, or a mixture thereof.

In the synthesis method of compound M1, the temperature of the reaction may be a conventional temperature for such reactions in the art. In the present disclosure, the reaction temperature may be 30° C. to 100° C., for example, 50° C. to 80° C., and for another example, 60° C. to 70° C.

In an embodiment of the present disclosure, in the synthesis method of compound M1, the temperature of the reaction may be 30° C. to 100° C., for example, 60° C. to 70° C., and for another example, 65° C. to 70° C.

In the synthesis method of compound M1, the progress of the reaction may be monitored by a conventional detection method in the art (such as TLC, MS, HPLC or NMR, etc.). In the present disclosure, the progress of the reaction is monitored by TLC when the compound SM disappears as the end point of the reaction. The time of the reaction may be, for example, 20 minutes to 10 hours (e.g., 1 hour, 4 hours, 5 hours, 6 hours, or 8 hours).

In the synthesis method of compound M1, the oxidizing agent may be directly used alone, or the oxidizing agent may be used in the form of a mixed solution with water, or the oxidizing agent may be used in the form of a mixed solution with an organic solvent. The water is conventional water in the art, such as purified water, distilled water or a mixture thereof. The organic solvent may be, for example, a chlorinated hydrocarbon solvent, an ether solvent, or a mixture thereof. The organic solvent generally has good solubility for the oxidizing agent. The organic solvent may be, for example, dichloromethane, tetrahydrofuran, dioxane or a mixture thereof. In the mixed solution (a mixed solution with water or a mixed solution with organic solvent), a molar ratio of the oxidizing agent to the water or the organic solvent may be 1:1-1:50, for example, 1:2-1:35, for another example, 1:2-1:30, for still another example, 1:20-1:35; and for yet another example, 1:20-1:30.

In the synthesis method of compound M1, the following steps are preferably comprised: mixing a mixture of the compound SM and the compound SM-A with the oxidizing agent to carry out the reaction. Further preferably, heating the mixture of the compound SM and the compound SM-A to 30° C. to 100° C., and then adding the oxidizing agent to carry out the reaction.

In the synthesis method of compound M1, after monitoring the completion of the reaction, a conventional post-treatment method in the art may be used for a post-treatment. In the present disclosure, the post-treatment may comprise the following steps: extracting the reaction solution after the completion of the reaction with an organic solvent, concentrating the organic phase, optionally slurrying the residue obtained after the concentration with the organic solvent, performing a solid-liquid separation, and optionally washing the solid with the organic solvent and drying to obtain a target compound; or, mixing the reaction solution after the completion of the reaction with water, performing the solid-liquid separation, and optionally washing the solid with the organic solvent and drying to obtain the target compound.

In an embodiment of the present disclosure, in the synthesis method of compound M1, after monitoring the completion of the reaction, the post-treatment may comprise the following steps: extracting the reaction solution after the completion of the reaction (for example, extracting at room temperature, preferably extracting with the ester solvent such as ethyl acetate or the halogenated hydrocarbon solvent such as dichloromethane), and then concentrating to obtain a concentrated solution (the volume of the concentrated solution is, for example, ⅛ to 1/10 of the volume of the extraction solvent), performing the solid-liquid separation (e.g., filtration under reduced pressure), washing a filter cake with the organic solvent for extraction (preferably washing with the ester solvent such as ethyl acetate or the halogenated hydrocarbon solvent such as dichloromethane), and drying the filter cake (e.g., draining or vacuum drying) to obtain the target compound;

in another embodiment of the present disclosure, in the synthesis method of compound M1, after monitoring the completion of the reaction, the post-treatment may comprise the following steps: mixing the reaction solution after the completion of the reaction with water (for example, mixing at room temperature, the amount of water is appropriate to generate a large amount of solid in the reaction solution), performing the solid-liquid separation (for example, filtration under reduced pressure), and drying the filter cake (for example, vacuum drying) to obtain the target compound;

in another embodiment of the present disclosure, in the synthesis method of compound M1, after monitoring the completion of the reaction, the post-treatment may comprise the following steps: extracting the reaction solution after the completion of the reaction (for example, extracting at room temperature, preferably extracting with the ester solvent such as ethyl acetate or the halogenated hydrocarbon solvent such as dichloromethane), removing the solvent in the organic phase, and slurrying the residue (preferably slurrying with a mixed solvent of the ester solvent and an alkane solvent, such as a mixed solvent of ethyl acetate and n-heptane, wherein a volume ratio of the ester solvent to the alkane solvent may be, for example, 1:2/v:v), performing the solid-liquid separation (such as filtration under reduced pressure), and drying the filter cake (such as vacuum drying) to obtain the target compound.

In the present disclosure, the synthesis method of compound M1 may be carried out in the absence of light. For example, the synthesis method of compound M1 may not require an irradiation of a mercury lamp, a tungsten lamp, or the like.

The present disclosure also provides a synthesis method of compound M2, and the method comprises the following steps: carrying out a reaction as shown below on compound M1 under the action of an acid; wherein the compound M1 is prepared according to the synthesis method as described above;

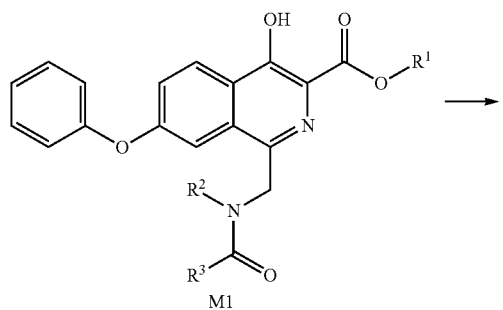

M1

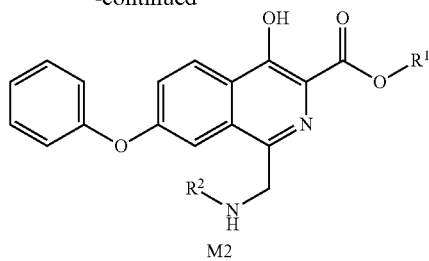

M2 wherein, the definitions of $R^1$, $R^2$ and $R^3$ are the same as above.

In the synthesis method of compound M2, the acid may be a conventional acid for such reactions in the art, such as an inorganic acid, an organic acid or a mixture thereof. The inorganic acid may be, for example, a hydrochloric acid (for example, a concentrated hydrochloric acid with a mass fraction of 36% or a hydrogen chloride ethanol solution), a sulfuric acid, a phosphoric acid or a mixture thereof (wherein a mass fraction of the sulfuric acid and the phosphoric acid may be, for example, 30%-85%). The organic acid may be, for example, an acetic acid, a trifluoroacetic acid, or a mixture thereof. The amount of the acid may be a conventional amount of such reactions in the art, and a volume-to-mass ratio of the acid to compound M1 is preferably 0.2 mL/g-5 mL/g, for example, 0.5 mL/g-5 mL/g, for another example, 0.2 mL/g-2.5 mL/g, and for still another example, 1 mL/g-2.5 mL/g.

In the synthesis method of compound M2, a solvent may be a conventional solvent for such reactions in the art, such as an ether solvent, an alcohol solvent, an amide solvent, a sulfoxide solvent or a mixture thereof. The ether solvent may be, for example, tetrahydrofuran, dioxane or a mixture thereof. The alcohol solvent may be, for example, methanol, ethanol, isopropanol or a mixture thereof. The amide solvent may be, for example, N,N-dimethylformamide, N,N-dimethylacetamide or a mixture thereof. The sulfoxide solvent may be, for example, DMSO.

In the synthesis method of compound M2, the solvent in the reaction may be a single solvent or a mixture of two or more solvents.

In an embodiment of the present disclosure, the solvent is preferably the alcohol solvent, or a mixed solvent of the ether solvent and the alcohol solvent, such as ethanol, or a mixed solvent of tetrahydrofuran and methanol. In the mixed solvent, a volume ratio of the ether solvent to the alcohol solvent may be 0.5:1-4:1, for example, 1:1-2:1. The amount of solvent may be a conventional amount for such reactions in the art, and a volume-mass ratio of the solvent to compound M1 is preferably 3 mL/g to 10 mL/g, for example, 3 mL/g to 8 mL/g; for another example, 5 mL/g to 8 mL/g.

In the synthesis method of compound M2, the temperature of the reaction may be a conventional temperature for such reactions in the art.

In the synthesis method of compound M2, the temperature of the reaction may be a conventional temperature for such reactions in the art. In the present disclosure, the reaction temperature may be 25° C. to 50° C., for example, 30° C. to 50° C., and for another example, 30° C. to 45° C.

In the synthesis method of compound M2, in the synthesis method of compound M2, the temperature of the reaction is 30° C. to 40° C.

In the synthesis method of compound M2, in the synthesis method of compound M2, the temperature of the reaction is 40° C. to 45° C.

In the synthesis method of compound M2, compound M1 may be

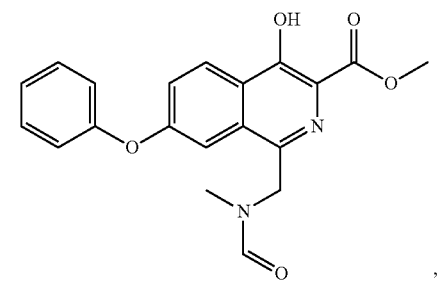
M1-1

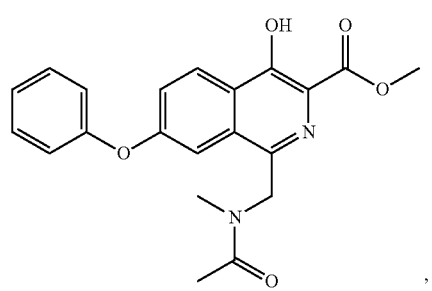

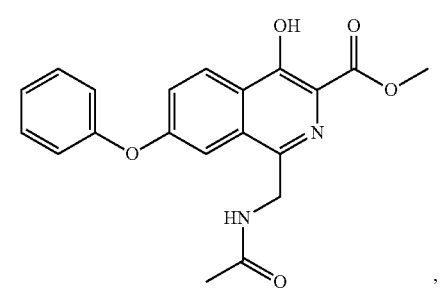

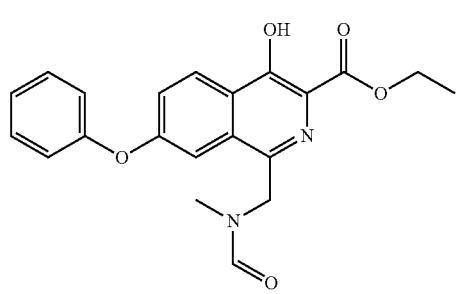
M1-A

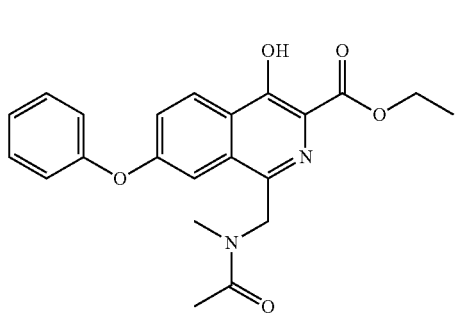

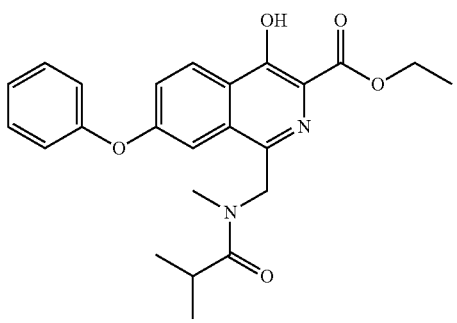
M1-C

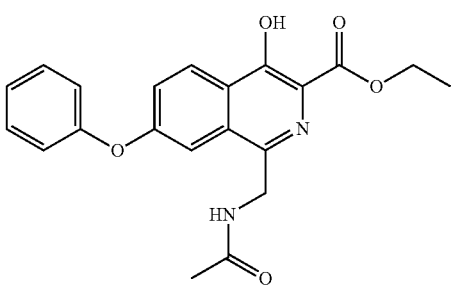
M1-D or

M1-E

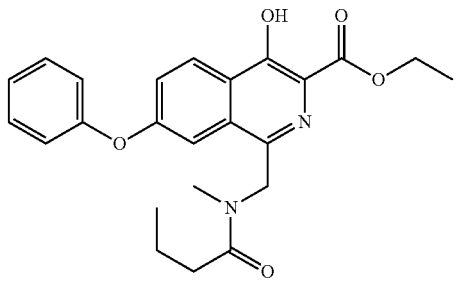

In the synthesis method of compound M2, the progress of the reaction may be monitored by a conventional detection method in the art (such as TLC, MS, HPLC or NMR, etc.). In the present disclosure, the progress of the reaction is monitored by TLC when the compound M1 disappears as the end point of the reaction. The time of the reaction may be, for example, 5 hours to 16 hours (e.g., 8 hours).

The synthesis method of compound M2 preferably comprises the following steps: mixing a mixture of compound M1 and the solvent with the acid to carry out the reaction. Preferably, the method further comprises the following steps: mixing the compound M1 with the solvent, heating to 25° C. to 50° C., and then adding the acid to carry out the reaction.

In the synthesis method of compound M2, after monitoring the completion of the reaction, a conventional post-treatment method in the art may be used for a post-treatment. In the present disclosure, the post-treatment may comprise the following steps: removing the solvent from the reaction solution after the completion of the reaction or adding an anti-solvent with a relatively large polarity difference from the reaction solvent until a large amount of solid is precipitated, performing a solid-liquid separation, optionally washing the solid with an organic solvent, and drying to obtain the target compound.

In an embodiment of the present disclosure, in the synthesis method of compound M2, after monitoring the completion of the reaction, the post-treatment may comprise the following steps: concentrating the reaction solution after the completion of the reaction until the solvent is removed or a large amount of solid is precipitated (e.g., vacuum concentration), performing the solid-liquid separation (e.g., filtration under reduced pressure), washing a filter cake with the alcohol solvent (e.g., methanol), and drying (e.g., draining or vacuum drying) to obtain the target compound.

In another embodiment of the present disclosure, in the synthesis method of compound M2, after monitoring the completion of the reaction, the post-treatment may comprise the following steps: concentrating the reaction solution after the completion of the reaction until the solvent is removed or a large amount of solid is precipitated (e.g., vacuum concentration), performing the solid-liquid separation (e.g., filtration under reduced pressure), washing the filter cake with the ether solvent (e.g., methyl tert-butyl ether), and drying (e.g., draining or vacuum drying) to obtain the target compound.

In another embodiment of the present disclosure, in the synthesis method of compound M2, after monitoring the completion of the reaction, the post-treatment may comprise the following steps: adding an anti-solvent to the reaction solution after the completion of the reaction until a large amount of solid is precipitated (the anti-solvent is preferably the ether solvent, such as isopropyl ether), performing the solid-liquid separation (e.g., filtration under reduced pressure), washing the filter cake with the ether solvent (e.g., isopropyl ether), and drying (e.g., vacuum drying) to obtain the target compound.

In an embodiment of the present disclosure, in the synthesis method of compound M1, the reaction solution after the completion of the reaction is directly reacted under the action of the acid to prepare compound M2 without the post-treatment.

The present disclosure also provides a synthesis method of compound M3, and the method comprises the following steps: carrying out a reaction as shown below on compound M2 in the presence of a hydrogen source; wherein the compound M2 is prepared according to the synthesis method as described above;

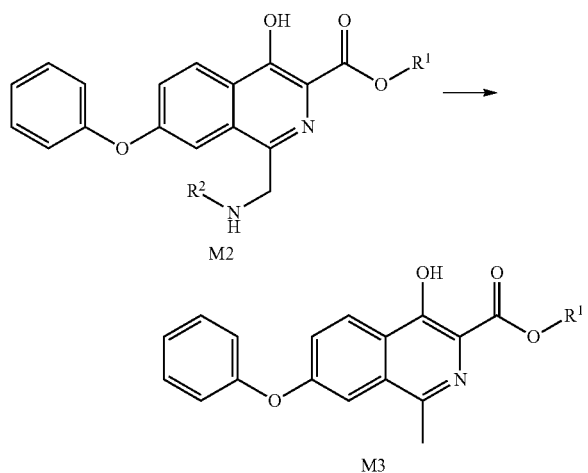

wherein, the definitions of $R^1$ and $R^2$ are the same as above.

In the synthesis method of compound M3, the hydrogen source may be a conventional hydrogen source for such reactions in the art, such as a metal element/hydrogen donor.

The metal element is, for example, a zinc powder, an iron powder or a mixture thereof. The amount of the metal element may be a conventional amount for such reactions in the art, and a molar ratio of the metal element to the compound M2 is preferably 1:1-10:1, for example, 2:1-8:1, for another example, 2:1-6:1, and for still another example, 2:1-3:1. The hydrogen donor may be a conventional hydrogen donor for such reactions in the art, such as an acid, ammonium formate, ammonium chloride or a mixture thereof. The amount of the hydrogen donor may be a conventional amount for such reactions in the art, and a molar ratio of the hydrogen donor to the metal element is preferably greater than 1:1, for example, greater than 5:1, greater than 10:1, greater than 20:1, greater than 40:1, or greater than 50:1.

In the synthesis method of compound M3, the metal element is preferably the zinc powder.

In the synthesis method of compound M3, the hydrogen donor may be any one of the acid, ammonium formate, ammonium chloride, or a mixture of the acid and ammonium chloride, or a mixture of the acid and ammonium formate.

In the synthesis method of compound M3, when the hydrogen donor is the acid, the acid is preferably a liquid, which may simultaneously serve as the solvent. The acid is preferably an inorganic acid, an organic acid or a mixture thereof. The inorganic acid is preferably a hydrochloric acid, a sulfuric acid, a phosphoric acid or a mixture thereof. The organic acid is preferably a formic acid, an acetic acid, a trifluoroacetic acid or a mixture thereof, more preferably, the acetic acid. The amount of the acid may be a conventional amount for such reactions in the art, and a volume-mass ratio of the acid to the compound M2 is preferably 3 mL/g-40 mL/g, for example, 8 mL/g-15 mL/g, and for another example, 8 mL/g-10 mL/g.

In the synthesis method of compound M3, when the hydrogen donor is ammonium formate or ammonium chloride, the amount of the hydrogen donor may be a conventional amount for such reactions in the art, and a molar ratio of the hydrogen donor to compound M2 is preferably 1:1-50:1, for example 5:1-40:1, and for another example, 10:1-30:1.

In the synthesis method of compound M3, when the hydrogen donor is the mixture of the acid and ammonium chloride, the acid is preferably a liquid, preferably an inorganic acid, an organic acid or a mixture thereof. The inorganic acid is preferably a hydrochloric acid, a sulfuric acid, a phosphoric acid or a mixture thereof. The organic acid is preferably a formic acid, an acetic acid, a trifluoroacetic acid or a mixture thereof, more preferably, the acetic acid. The amount of the acid may be a conventional amount for such reactions in the art, and a volume-mass ratio of the acid to ammonium chloride is preferably 2 mL/g-10 mL/g, for example, 3 mL/g-8 mL/g, and for another example, 5 mL/g. The volume-mass ratio of the amount of the acid to the compound M2 is 1 mL/g-10 mL/g, for example, 1 mL/g-5 mL/g, and for another example, 2 mL/g.

In the synthesis method of compound M3, when the hydrogen donor is a solid such as ammonium formate or ammonium chloride, the reaction may also be carried out in a solvent. The solvent may be a conventional solvent for such reactions in the art, such as water, an alcohol solvent, an amide solvent, a sulfoxide solvent or a mixture thereof. The alcohol solvent may be, for example, methanol, ethanol, isopropanol or a mixture thereof. The amide solvent may be, for example, N,N-dimethylformamide, N,N-dimethylacetamide or a mixture thereof. The sulfoxide solvent may be, for example, DMSO. The amount of the solvent may be selected according to actual needs.

In the synthesis method of compound M3, when the hydrogen donor is the mixture of the acid and ammonium formate or the mixture of the acid and ammonium chloride, the reaction may also be carried out in the solvent. The solvent may be a conventional solvent for such reactions in the art, such as water, an alcohol solvent, an amide solvent, a sulfoxide solvent or a mixture thereof. The alcohol solvent may be, for example, methanol, ethanol, isopropanol or a mixture thereof. The amide solvent may be, for example, N,N-dimethylformamide, N,N-dimethylacetamide or a mixture thereof. The sulfoxide solvent may be, for example, DMSO. The amount of the solvent may be selected according to actual needs.

In the synthesis method of compound M3, the temperature of the reaction may be a conventional temperature for such reactions in the art.

In the present disclosure, in the synthesis method of compound M3, the temperature of the reaction may be 25° C. to 60° C., for example, 40° C. to 60° C.

In an embodiment of the present disclosure, in the synthesis method of compound M3, the temperature of the reaction may be 25° C. to 60° C., for example, 45° C. to 60° C., and for another example, 50° C. to 60° C.

In an embodiment of the present disclosure, in the synthesis method of compound M3, the temperature of the reaction may be 25° C. to 60° C., for example, 40° C. to 60° C., and for another example, 40° C. to 50° C.

In the synthesis method of compound M3, compound M2 may be

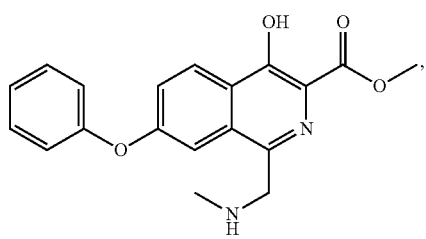

M2-1

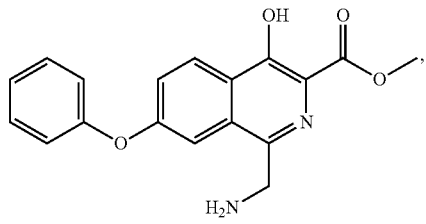

M2-2

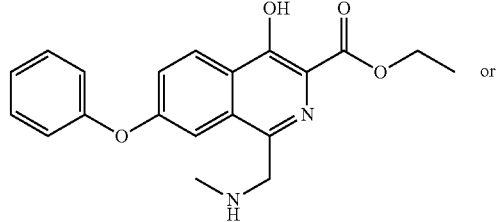

M2-A or

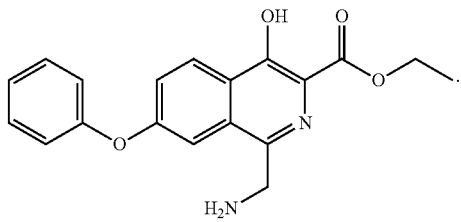

M2-D

In the synthesis method of compound M3, the progress of the reaction may be monitored by a conventional detection method in the art (such as TLC, MS, HPLC or NMR, etc.). In the present disclosure, the progress of the reaction is monitored by TLC when the compound M2 disappears as the end point of the reaction. The time of the reaction may be, for example, 1 hour to 10 hours (for example, 2 hours to 6 hours, and for another example, 2 to 3 hours).

The synthesis method of compound M3 preferably comprises the following steps: mixing a mixture of the compound M2 and the acid with a reducing agent to carry out the reaction; and further preferably comprises the following steps: adding the reducing agent to the mixture of the compound M2 and the acid, and heating to 25° C. to 60° C. to carry out the reaction.

The synthesis method of compound M3 preferably comprises the following steps: mixing a mixture of the compound M2 and the hydrogen donor with the metal element to carry out the reaction; and further preferably comprises the following steps: adding the metal element to the mixture of the compound M2 and the hydrogen donor, and heating to 25° C. to 60° C. to carry out the reaction.

In the synthesis method of compound M3, after monitoring the completion of the reaction, a conventional post-treatment method in the art may be used for a post-treatment. In the present disclosure, the post-treatment may comprise the following steps: performing a solid-liquid separation on the reaction solution after the completion of the reaction, concentrating the filtrate, adding an organic solvent to precipitate the solid, slurrying the obtained solid with the organic solvent, and performing the solid-liquid separation to obtain the target compound; or, mixing the reaction solution after the completion of the reaction with water or a sodium chloride aqueous solution to precipitate the solid, optionally slurrying the obtained solid with the organic solvent, and performing the solid-liquid separation to obtain the target compound.

In an embodiment of the present disclosure, in the synthesis method of compound M3, after monitoring the completion of the reaction, the post-treatment may comprise the following steps: performing the solid-liquid separation (for example, filtration) on the reaction solution after the completion of the reaction, washing a filter cake (preferably twice) with the organic solvent (preferably a mixed solvent of the halogenated hydrocarbon solvent and the alcohol solvent, such as a mixed solvent of dichloromethane and methanol), and concentrating the filtrate to ⅕-1/15 of the amount of the organic solvent used for washing (for example, 1/7.5-1/10) to obtain a concentrated solution, and then adding a mixed solvent of the alcohol solvent and water (for example, a mixed solvent of isopropanol and water, a volume ratio of the alcohol solvent to water may be 1:1-1:5, such as 1:2, a volume ratio of the mixed solvent to the concentrated solution may be, for example, 3:1-7.5:1), performing a solid-liquid separation (such as filtration under reduced pressure), slurrying the filter cake with the mixed solvent of the alcohol solvent and water (such as a mixed solvent of methanol and water, the volume ratio of the alcohol solvent to water may be, for example, 1:3), performing the solid-liquid separation (for example, filtration under reduced pressure) to obtain the target compound.

In an embodiment of the present disclosure, in the synthesis method of compound M3, after monitoring the completion of the reaction, the post-treatment may comprise the following steps: mixing the reaction solution after the completion of the reaction with the sodium chloride aqueous solution, performing a solid-liquid separation (e.g., filtration under reduced pressure), adding the organic solvent to the filter cake for slurrying, wherein the organic solvent is preferably acetone, performing the solid-liquid separation (e.g., filtration under reduced pressure), and drying the filter cake (e.g., vacuum drying) to obtain the target compound.

In another embodiment of the present disclosure, in the synthesis method of compound M3, after monitoring the completion of the reaction, the post-treatment may comprise the following steps: mixing the reaction solution after the completion of the reaction with the sodium chloride aqueous solution, performing a solid-liquid separation (e.g., filtration under reduced pressure), and drying the filter cake (e.g., vacuum drying) to obtain the target compound;

In the present disclosure, in the synthesis methods of compounds M1, M2, M3, after the reaction is completed, the compounds M1, M2 and M3 may be directly subjected to the next reaction without post-treatment steps.

The present disclosure also provides a synthesis method of roxadustat, and the method comprises the following steps: carrying out a reaction as shown below between compound M3 and $NH_2CH_2COOR^a$; wherein the compound M3 is prepared according to the synthesis method as described above;

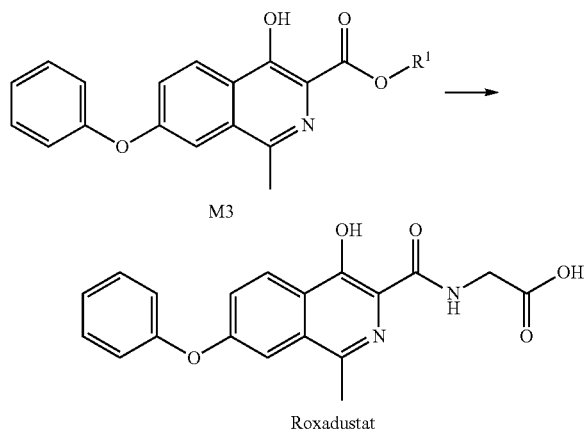

wherein, $R^a$ is H or Na; $R^1$ is defined as above;

in the synthesis method of roxadustat, when $R^a$ is H, the compound M3 reacts with $NH_2CH_2COOR^a$ in the presence of alkali; when $R^a$ is Na, the compound M3 and $NH_2CH_2COOR^a$ may optionally react in the presence of alkali.

In the synthesis method of roxadustat, the alkali may be a conventional alkali for such reactions in the art. In the present disclosure, the alkali is selected from one or more of sodium methoxide, sodium ethoxide, sodium tert-butoxide, potassium tert-butoxide, sodium hydroxide, potassium hydroxide, lithium hydroxide, 1,8-diazabicycloundec-7-ene, triethylamine, N,N-diisopropylethylamine and pyridine; the alkali is preferably 1,8-diazabicycloundec-7-ene.

In the synthesis method of roxadustat, a solvent of the reaction may be a conventional solvent for such reactions in the art. In present disclosure, the solvent is selected from one or more of methanol, ethanol, n-butanol, tetrahydrofuran, 1,4-dioxane, N,N-dimethylacetamide, acetonitrile, dimethyl sulfoxide, N-methylpyrrolidone, toluene and benzene; the solvent is preferably methanol, acetonitrile or ethanol.

In the synthesis method of roxadustat, the temperature of the reaction may be a conventional temperature for such reactions in the art. In the present disclosure, the temperature of the reaction may be 50° C. to 130° C., for example, 60° C. to 120° C., and for another example, 60° C. to 90° C.

In the synthesis method of roxadustat, compound M3 may be

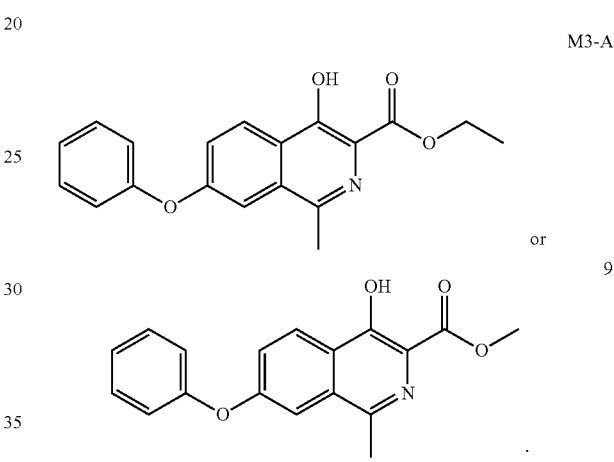

In the synthesis method of roxadustat, a condition of the reaction is a conventional condition for such reactions in the art.

In the present disclosure, the synthesis method of roxadustat has the following routes:

route 1:

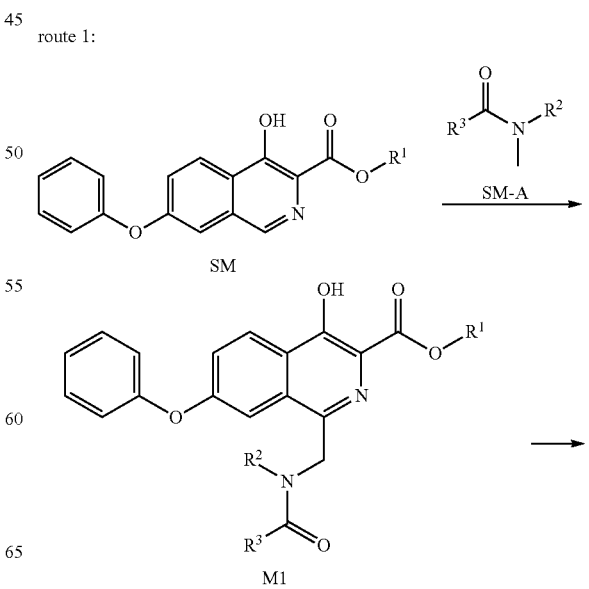

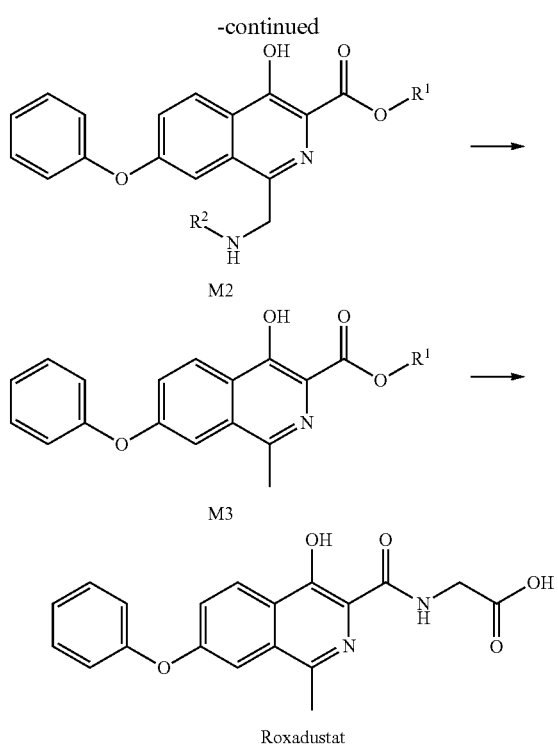

route 2:

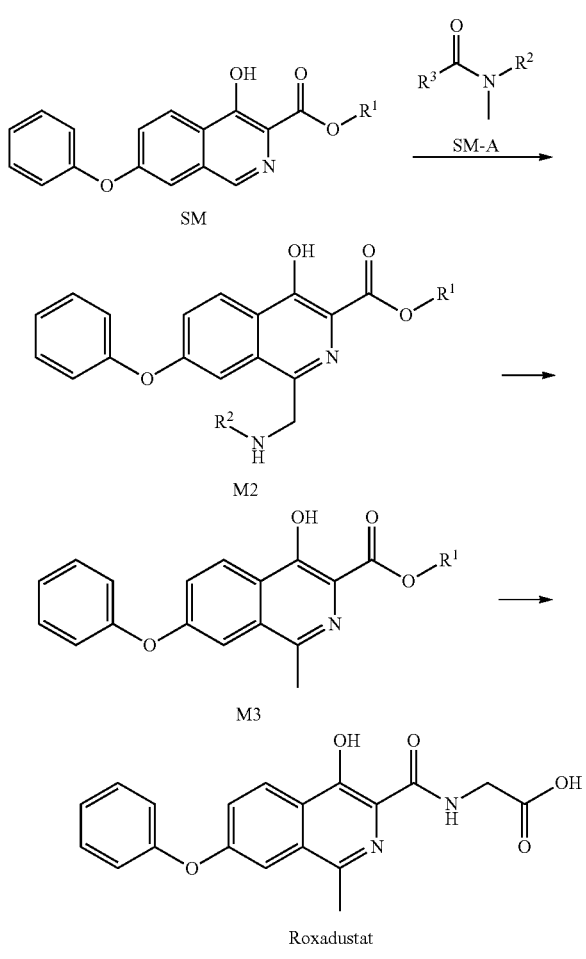

wherein, the definitions of $R^1$, $R^2$ and $R^3$ are the same as above, and the reaction conditions of each step are the same as above.

The present disclosure also provides a compound M1, a compound M2 or a salt thereof:

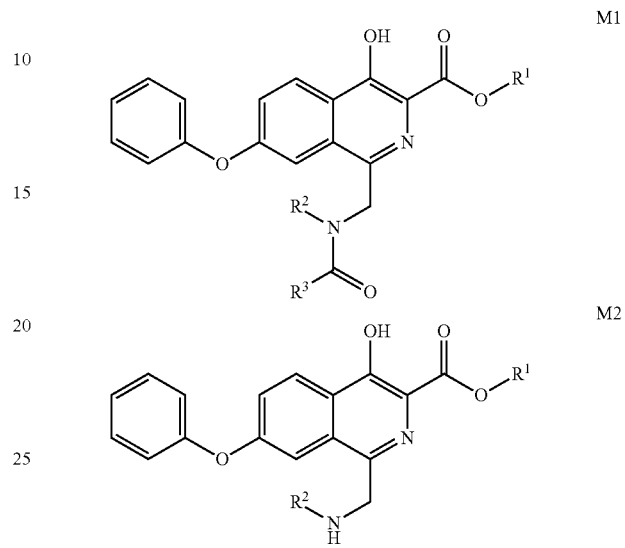

wherein, the definitions of $R^1$, $R^2$ and $R^3$ are the same as above.

The salt of compound M2 is generally a salt formed by compound M2 and an acid. The acid may be, for example, an inorganic acid or an organic acid, such as a hydrochloric acid, a sulfuric acid, a phosphoric acid, an acetic acid or a trifluoroacetic acid. The acid is preferably the hydrochloric acid.

The compounds M1 and M2 of the present disclosure may be used as intermediates for the synthesis of roxadustat.

In the present disclosure, the compound M1 may be

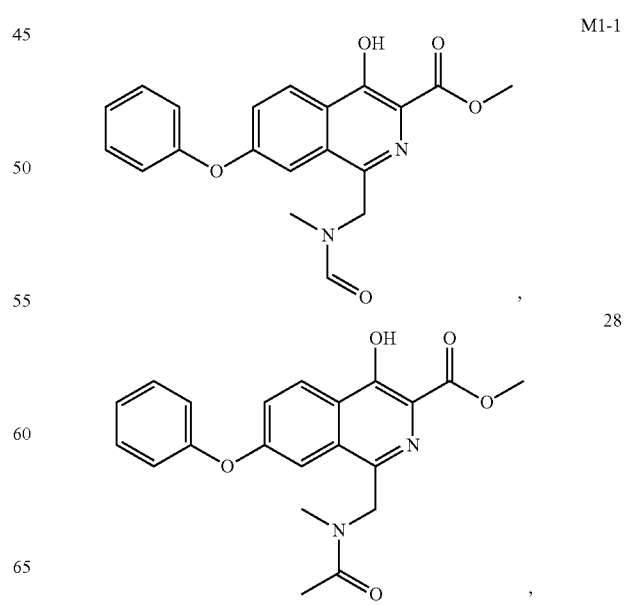

M1-2

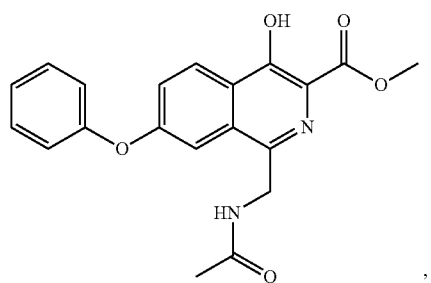

,

M1-F

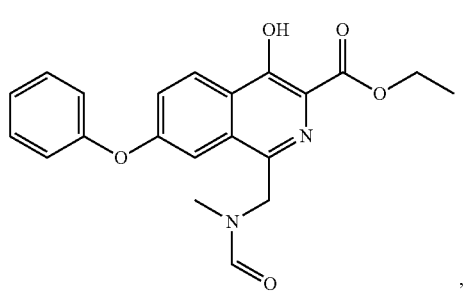

,

M1-A

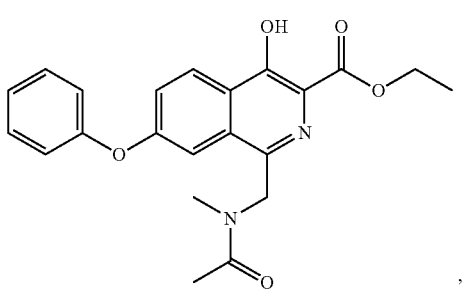

,

M1-C

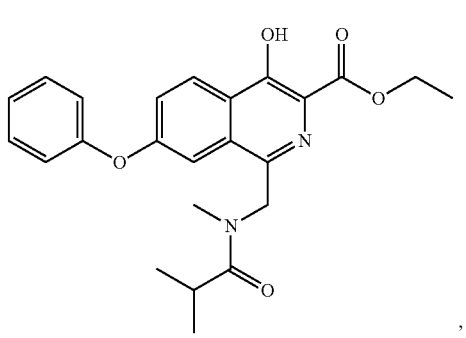

,

M1-D

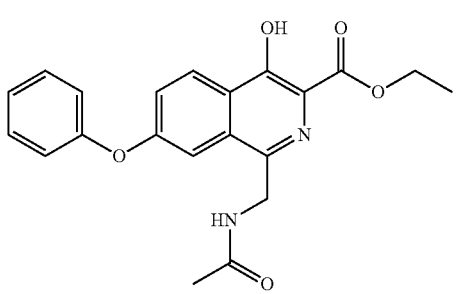

or

M1-E

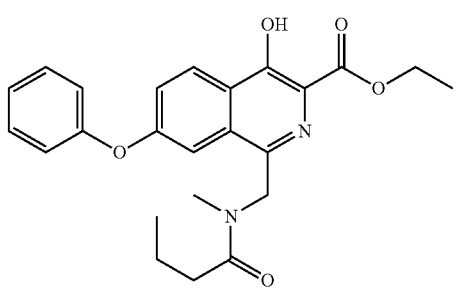

.

In the present disclosure, the compound M2 may be

M2-1

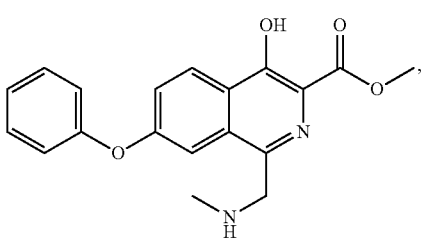

,

M2-2

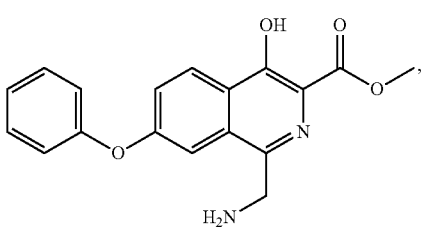

,

M2-A

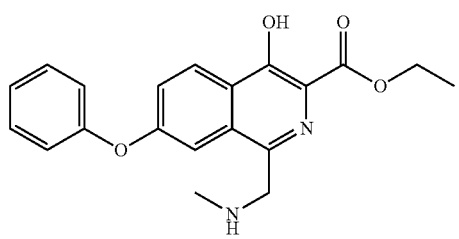

or

M2-D

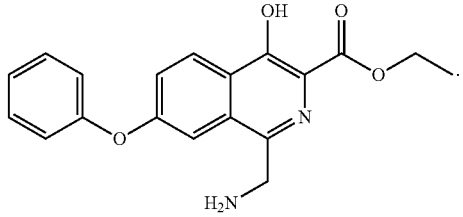

.

The present disclosure also provides a use of the aforementioned compound M1, the aforementioned compound M2 or the salt thereof in the manufacture of roxadustat.

On the other hand, as a new drug on the market in recent years, there is still a lack of research on intermediate process impurities in the process development of the brand-new preparation method of roxadustat. Therefore, the present disclosure provides a compound containing an isoquinoline ring, a preparation method therefor and a use thereof. The compound containing the isoquinoline ring participates in the subsequent reaction, and the derivative impurities of the compound containing the isoquinoline ring are difficult to remove, which have a great impact on the quality of the roxadustat active pharmaceutical ingredients (API). The compound containing the isoquinoline ring may be used as a reference substance to control the quality of roxadustat synthesis intermediates and roxadustat API, which is necessary to control the quality of the roxadustat API and even the drug product.

Specifically, the inventor found that there is always an impurity with a content as high as 0.4%-0.5% in the roxadustat API obtained by the above new preparation method, which significantly exceeds the requirement that the impurity identification threshold should not exceed 0.10% in the pharmaceutical research guiding guidelines promulgated by the International Council for Harmonisation of Technical Requirements for Registration of Pharmaceuticals for Human Use (ICH). After a structural identification of the impurity, the impurity was confirmed to be 4-hydroxy-1-methyl-7-phenoxyisoquinoline-3-carboxylic acid (compound II), and there was a carboxyl group in this structure, which was similar to roxadustat in polarity and solubility, resulting in difficult separation and removal. Through tracing the source of compound II, it was confirmed that there are two ways to produce compound II: (1) compound I with the content greater than 1% was stably produced in the process of preparing intermediate M2-A from intermediate M1-A by hydrolysis, and compound I was comprised in intermediate M2-A and participated in the subsequent zinc powder reduction reaction to convert into compound II; (2) M2-A itself may also produce a certain amount of compound II due to inevitable hydrolysis during the zinc powder reduction reaction. The carboxyl of compound II was unable to be complete the conversion due to insufficient activity and no reaction with sodium glycinate or glycine, and finally remained in the roxadustat API. In view of the above two ways of producing compound II, it is necessary to control compound I and compound II respectively in the process of preparing intermediates M2-A and M3-A (especially process scale-up exploration and process optimization for industrial production), so as to make the purity of roxadustat API meet the requirements of quality standards.

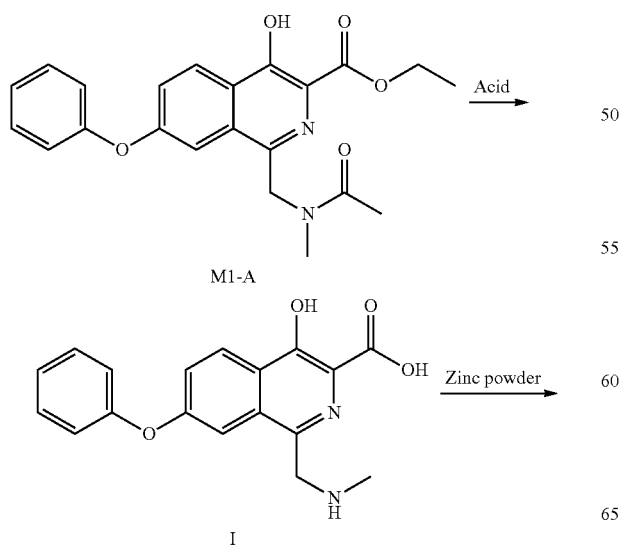

-continued

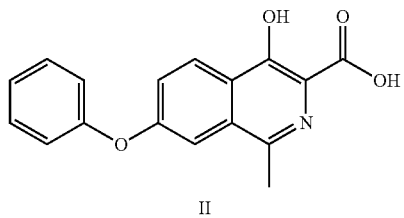

II

On the basis of accurately tracing the source of the above impurities, the inventor has significantly reduced the content of impurity compound II in the finished product of roxadustat API by effectively controlling impurity compound I in intermediate M2-A and impurity compound II in intermediate M3-A continuously, thereby improving the purity of API.

The present disclosure provides a compound containing an isoquinoline ring represented by formula I or a salt thereof:

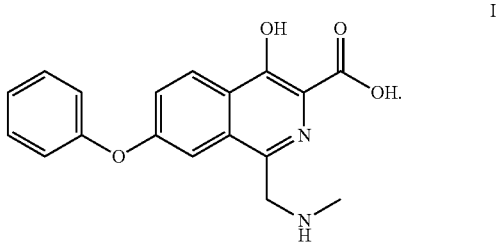 [SMILES: CNCc1nc(C(=O)O)c(O)c2ccc(Oc3ccccc3)cc12]

The present disclosure also provides a preparation method of the compound containing the isoquinoline ring represented by formula I, which is a preparation method using preparative liquid chromatography for separation and purification.

The present disclosure also provides a preparation method of the compound containing the isoquinoline ring represented by formula I, and the method comprises the following steps: performing a gradient elution on a substance containing the compound containing the isoquinoline ring represented by formula I

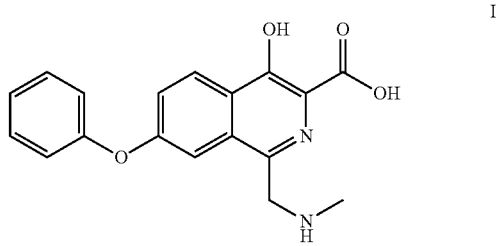 [SMILES: CNCc1nc(C(=O)O)c(O)c2ccc(Oc3ccccc3)cc12]

by high performance liquid chromatography to obtain the compound containing the isoquinoline ring represented by formula I;

the substance containing the compound containing the isoquinoline ring represented by formula I is M2-A

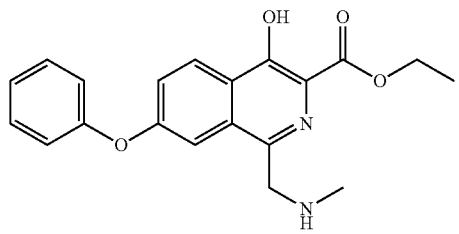

M2-A containing the compound containing the isoquinoline ring represented by formula I;

a stationary phase of the high performance liquid chromatography is octadecyl silane bonded silica gel;

a mobile phase of the high performance liquid chromatography is a mobile phase A and a mobile phase B; the mobile phase A is a 10 mmol/L $NH_4HCO_3$ aqueous solution; the mobile phase B is a mixed solvent of acetonitrile and isopropanol (1:1).

In the preparation method of the compound containing the isoquinoline ring represented by formula I, the substance containing the compound containing the isoquinoline ring represented by formula I

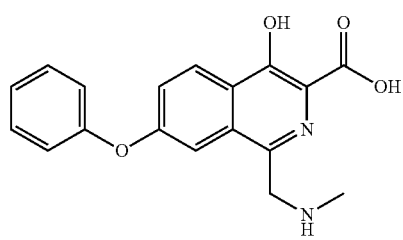

I may be dissolved by water and acetonitrile before adding to the column.

In the preparation method of the compound containing the isoquinoline ring represented by formula I, when the substance containing the compound containing the isoquinoline ring represented by formula I

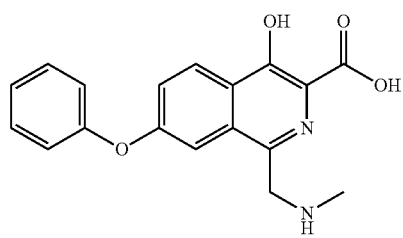

I is dissolved by water and acetonitrile, the ratio of water to acetonitrile may be 4:1.

In the preparation method of the compound containing the isoquinoline ring represented by formula I, when the substance containing the compound containing the isoquinoline ring represented by formula I

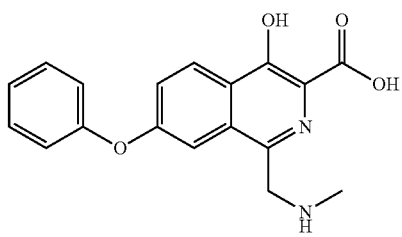

I is dissolved by water and acetonitrile, the concentration of the substance containing the compound containing the isoquinoline ring represented by formula I

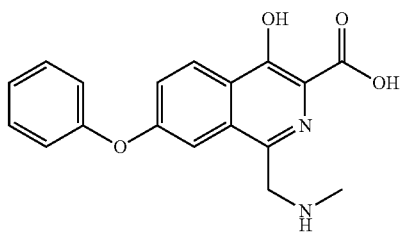

I in the formed solution may be 20 mg/mL.

In the preparation method of the compound containing the isoquinoline ring represented by formula I, parameters of the gradient elution by high performance liquid chromatography may be:

| min | Mobile phase A | Mobile phase B |
| --- | --- | --- |
| 0 | 50% | 50% |
| 2 | 40% | 60% |
| 12 | 5% | 95% |
| 15 | 5% | 95% |
| 16 | 100% | 0% |
| 18 | 100% | 0% |

In the preparation method of the compound containing the isoquinoline ring represented by formula I, the times of the gradient elution by high performance liquid chromatography may be one or multiple times.

In the preparation method of the compound containing the isoquinoline ring represented by formula I, when the times of the gradient elution by high performance liquid chromatography is multiple times, the multiple times may be 2 times or 3 times.

In the preparation method of the compound containing the isoquinoline ring represented by formula I, the high performance liquid chromatography may be a preparative high performance liquid chromatography.

In the preparation method of the compound containing the isoquinoline ring represented by formula I, the chromatographic column of the high performance liquid chromatography may be YMC-Triart $C_{18}$ 10 μm 250*30 mm.

In the preparation method of the compound containing the isoquinoline ring represented by formula I, the detection wavelength of the high performance liquid chromatography may be a conventional detection wavelength in the art, such as 220 nm and/or 254 nm.

In the preparation method of the compound containing the isoquinoline ring represented by formula I, the injection volume of the high performance liquid chromatography may be a conventional injection volume in the art, such as 125 mg.

In the preparation method of the compound containing the isoquinoline ring represented by formula I, the column temperature of the high performance liquid chromatography may be a conventional column temperature in the art, such as room temperature.

In the preparation method of the compound containing the isoquinoline ring represented by formula I, the flow rate of the high performance liquid chromatography may be mL/min.

In the preparation method of the compound containing the isoquinoline ring represented by formula I, the retention time of the compound containing the isoquinoline ring represented by formula I may be 6.1 min.

In the preparation method of the compound containing the isoquinoline ring represented by formula I, the content of the compound containing the isoquinoline ring represented by formula I in the M2-A

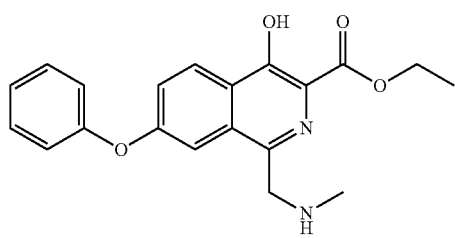

M2-A may be greater than or equal to 1.0%.

The preparation method of the compound containing the isoquinoline ring represented by formula I may further comprise the following steps: carrying out a reaction as shown below on compound M1-A

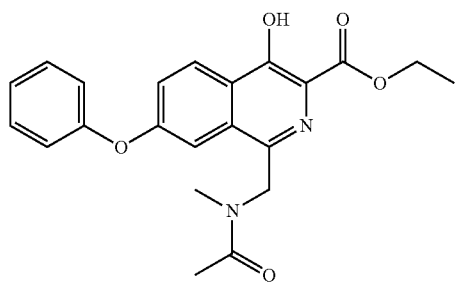

M1-A under the action of an acid to obtain the substance M2-A

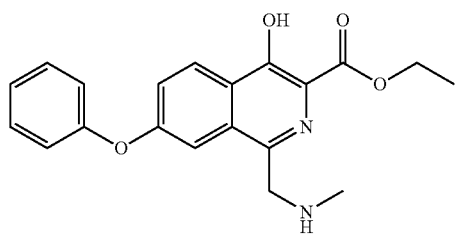

M2-A containing the compound containing the isoquinoline ring represented by formula I;

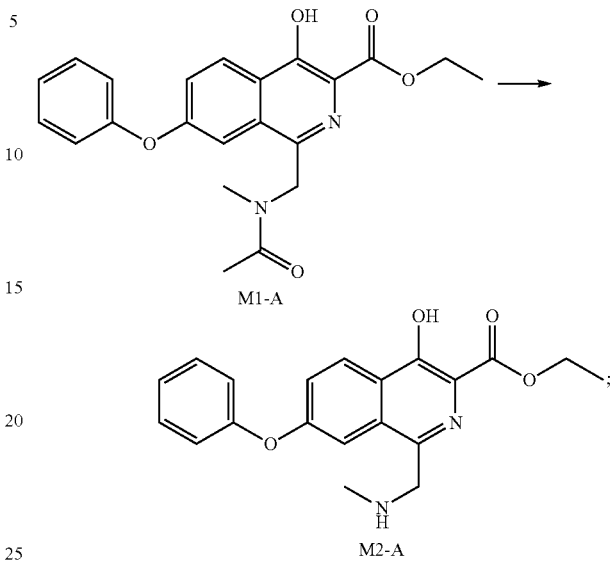

in the preparation method of the substance M2-A containing the compound containing the isoquinoline ring represented by formula I, the acid may be a conventional acid for such reactions in the art, such as an inorganic acid, an organic acid or a mixture thereof. The inorganic acid may be, for example, a hydrochloric acid (for example, a concentrated hydrochloric acid with a mass fraction of 36% or a hydrogen chloride ethanol solution), a sulfuric acid, a phosphoric acid or a mixture thereof (wherein a mass fraction of the sulfuric acid and the phosphoric acid may be, for example, 30%-85%). The organic acid may be, for example, an acetic acid, a trifluoroacetic acid, or a mixture thereof. The amount of the acid may be a conventional amount of the acid for such reactions in the art. Preferably, the acid is a concentrated hydrochloric acid with a mass fraction of 36%, or a hydrogen chloride ethanol solution. More preferably, the acid is the concentrated hydrochloric acid with the mass fraction of 36%, or the hydrogen chloride ethanol solution with a mass fraction of 33%.

In the preparation method of the substance M2-A containing the compound containing the isoquinoline ring represented by formula I, a solvent may be a conventional solvent for such reactions in the art, such as an ether solvent, an alcohol solvent, an amide solvent, a sulfoxide solvent or a mixture thereof. The ether solvent may be, for example, tetrahydrofuran, dioxane or a mixture thereof. The alcohol solvent may be, for example, methanol, ethanol, isopropanol or a mixture thereof. The amide solvent may be, for example, N,N-dimethylformamide, N,N-dimethylacetamide or a mixture thereof. The sulfoxide solvent may be, for example, DMSO. In the preparation method of the substance M2-A containing the compound containing the isoquinoline ring represented by formula I, the solvent of the reaction may be a single solvent or a mixture of two or more solvents. In an embodiment of the present disclosure, the solvent is preferably the alcohol solvent, or a mixed solvent of the ether solvent and the alcohol solvent, such as ethanol, or a mixed solvent of tetrahydrofuran and methanol. In the mixed solvent, a volume ratio of the ether solvent to the alcohol solvent may be 0.5:1-4:1, for example, 1:1-2:1. The amount of the solvent may be a conventional amount of the solvent for such reactions in the art. Preferably, the solvent is ethanol, or a mixed solvent of tetrahydrofuran and methanol. More preferably, the solvent is ethanol or a mixed solvent of tetrahydrofuran and methanol with a volume ratio of 1:1 to 2:1.

In the preparation method of the substance M2-A containing the compound containing the isoquinoline ring represented by formula I, the temperature of the reaction may be a conventional temperature for such reactions in the art. In the present disclosure, the temperature of the reaction may be 25° C. to 50° C., for example, 30° C. to 50° C., and for another example, 30° C. to 45° C.

In an embodiment of the present disclosure, in the preparation method of the substance M2-A containing the compound containing the isoquinoline ring represented by formula I, the temperature of the reaction is 30° C. to 40° C.

In another embodiment of the present disclosure, in the preparation method of the substance M2-A containing the compound containing the isoquinoline ring represented by formula I, the temperature of the reaction is 40° C. to 45° C.

In the preparation method of the substance M2-A containing the compound containing the isoquinoline ring represented by formula I, the progress of the reaction may be monitored by a conventional detection method in the art (such as TLC, MS, HPLC or NMR, etc.). In the present disclosure, the progress of the reaction is monitored by TLC when the compound M1-A disappears as the end point of the reaction.

In the preparation method of the substance M2-A containing the compound containing the isoquinoline ring represented by formula I, after monitoring the completion of the reaction, a conventional post-treatment method in the art may be used for a post-treatment. In the present disclosure, the post-treatment may comprise the following steps: concentrating the reaction solution after the completion of the reaction until the solvent is removed or a large amount of solid is precipitated (e.g., vacuum concentration), performing a solid-liquid separation (e.g., filtration under reduced pressure), washing a filter cake with the alcohol solvent (e.g., methanol), and drying (e.g., draining or vacuum drying) to obtain the substance M2-A containing the compound containing the isoquinoline ring represented by formula I.

The preparation method of the compound containing the isoquinoline ring represented by formula I may further comprise a preparation method of compound M1-A: carrying out a reaction as shown below on compound SM2 and DMA under the action of an oxidizing agent to obtain the compound M1-A;

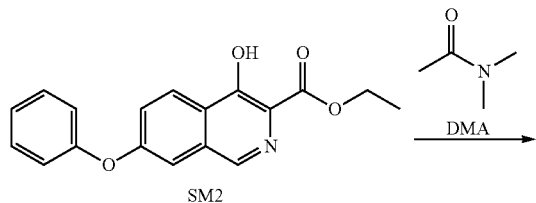

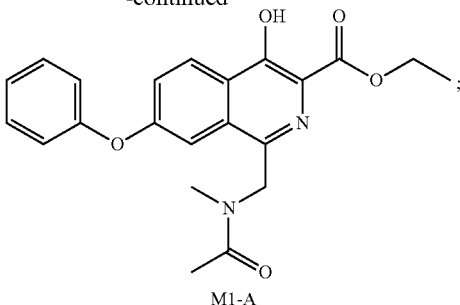

in the preparation method of compound M1-A, the oxidizing agent may be a conventional oxidizing agent for such reactions in the art. In the present disclosure, the oxidizing agent may be, a persulfate oxidizing agent, such as alkali metal persulfate. The alkali metal persulfate may be sodium persulfate, potassium persulfate, potassium peroxymonosulfate composite salt (Oxone) or a mixture thereof. Preferably, the oxidizing agent is sodium persulfate.

In the preparation method of the compound M1-A, the amount of the oxidizing agent may be a conventional amount of the oxidizing agent for such reactions in the art. In the present disclosure, a molar ratio of the compound SM2 to the oxidizing agent is 1:1-1:5, for example, 1:1.5-1:3, for another example, 1:2.

In the preparation method of the compound M1-A, the amount of the compound SM2 and the compound DMA may be the conventional amount for such reactions in the art. In the present disclosure, a molar ratio of the compound DMA to the compound SM2 may be greater than 1:1, for example, greater than 5:1, greater than 10:1, greater than 20:1, greater than 40:1, or greater than 50:1. In principle, in order to control the cost, those skilled in the art know that the amount of the compound DMA should be controlled within an appropriate range. Preferably, a molar ratio of the compound DMA to the compound SM2 is greater than 20:1.

In the preparation method of the compound M1-A, the solvent may be a conventional solvent for such reactions in the art, such as a chlorinated hydrocarbon solvent, an ether solvent or a mixture thereof. The solvent generally has good solubility for compound SM2, and is not easily oxidized or does not participate in the reaction. The compound DMA may also be used as a reaction solvent and a raw material at the same time. Preferably, compound DMA is used as both the reaction raw material and the solvent.

In the preparation method of compound M1-A, the temperature of the reaction may be a conventional temperature for such reactions in the art.

In the present disclosure, the temperature of the reaction may be 30° C. to 100° C., for example, 50° C. to 80° C., and for another example, 60° C. to 70° C. In an embodiment of the present disclosure, in the preparation method of compound M1-A, the temperature of the reaction may be 30° C. to 100° C., for example, 60° C. to 70° C., and for another example, 65° C. to 70° C. Preferably, the temperature of the reaction is 60° C. to 70° C.

In the preparation method of compound M1-A, the oxidizing agent may be directly used alone, or the oxidizing agent is used in the form of a mixed solution with water, or the oxidizing agent is used in the form of a mixed solution with an organic solvent.

The water is conventional water in the art, such as purified water, distilled water or a mixture thereof. The organic solvent may be, for example, the chlorinated hydrocarbon solvent, the ether solvent, or the mixture thereof. The organic solvent generally has good solubility for the oxidizing agent. The organic solvent may be, for example, dichloromethane, tetrahydrofuran, dioxane or a mixture thereof. In the mixed solution (a mixed solution with water or a mixed solution with organic solvent), a molar ratio of the oxidizing agent to the water or the organic solvent may be 1:1-1:50, for example, 1:2-1:35, for another example, 1:2-1:30, for still another example, 1:20-1:35, and for yet another example, 1:20-1:30. Preferably, the oxidizing agent is in the form of a mixed solution in which the molar ratio of sodium persulfate to water is 1:20-1:30.

In the preparation method of compound M1-A, the progress of the reaction may be monitored by a conventional detection method in the art (such as TLC, MS, HPLC or NMR, etc.). In the present disclosure, the progress of the reaction is monitored by TLC when the compound SM2 disappears as the end point of the reaction.

In the preparation method of compound M1-A, after monitoring the completion of the reaction, a conventional post-treatment method in the art may be used for a post-treatment. In present disclosure, the post-treatment may comprise the following steps: mixing the reaction solution after the completion of the reaction with water (for example, mixing at room temperature, the amount of water is appropriate to generate a large amount of solid in the reaction solution), performing a solid-liquid separation (for example, filtration under reduced pressure), and drying the filter cake (for example, vacuum drying) to obtain the target compound M1-A.

The present disclosure also provides a preparation method of the compound containing the isoquinoline ring represented by formula I, which is a preparation method using chemical target-oriented synthesis.

The present disclosure also provides a preparation method of the compound containing the isoquinoline ring represented by formula I, and the method comprises the following steps: carrying out a reaction as shown below on compound M1 under the action of an acid to obtain the compound containing the isoquinoline ring represented by formula I; the temperature of the reaction is 60 to 70° C.;

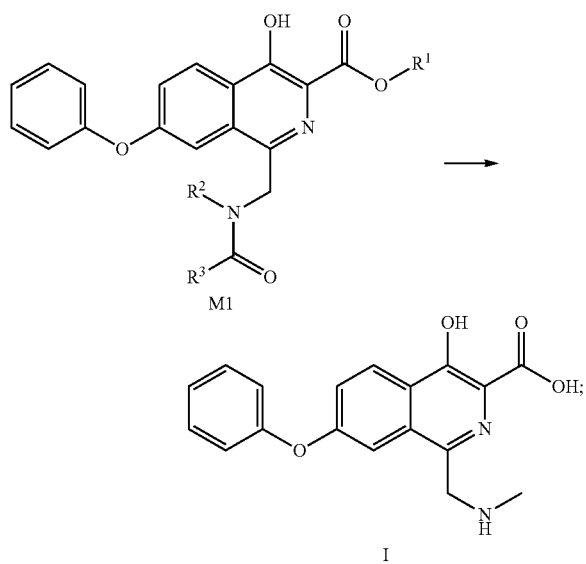

wherein, the definitions of $R^1$ and $R^3$ are the same as above, and $R^2$ is methyl.

Preferably, $R^1$ is H or $C_1$-$C_4$ alkyl; more preferably, $R^1$ is $C_1$-$C_4$ alkyl; further preferably, $R^1$ is methyl, ethyl, n-propyl, isopropyl, n-butyl, isobutyl, sec-butyl or tert-butyl; most preferably, $R^1$ is methyl or ethyl;

preferably, $R^3$ is H or $C_1$-$C_4$ alkyl; more preferably, $R^3$ is H, methyl, ethyl, n-propyl, isopropyl, n-butyl, isobutyl, sec-butyl or tert-butyl; most preferably, $R^3$ is methyl or H.

In the preparation method of the compound containing the isoquinoline ring represented by formula I, the compound M1 may be any of the following compounds:

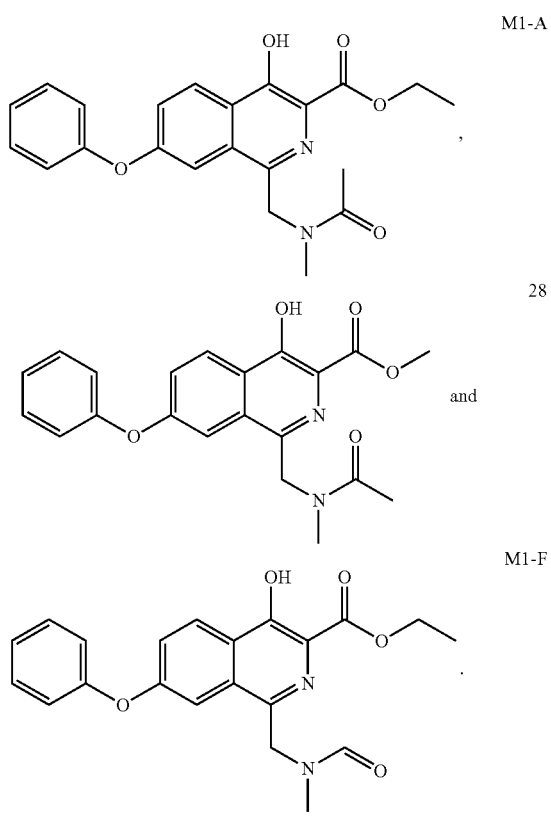

In the preparation method of the compound containing the isoquinoline ring represented by formula I, the acid may be a conventional acid for such reactions in the art, such as an inorganic acid, an organic acid or a mixture thereof. The inorganic acid may be, for example, a hydrochloric acid (for example, a concentrated hydrochloric acid with a mass fraction of 36% or a hydrogen chloride ethanol solution), a sulfuric acid, a phosphoric acid or a mixture thereof (wherein a mass fraction of the sulfuric acid and the phosphoric acid may be, for example, 30%-85%). The organic acid may be, for example, an acetic acid, a trifluoroacetic acid, or a mixture thereof. The amount of the acid may be a conventional amount of the acid for such reactions in the art. Preferably, the acid is a concentrated hydrochloric acid with a mass fraction of 36%, or a hydrogen chloride ethanol solution. More preferably, the acid is the concentrated hydrochloric acid with the mass fraction of 36%, or the hydrogen chloride ethanol solution with a mass fraction of 33%.

In the preparation method the compound containing the isoquinoline ring represented by formula I, the solvent may be a conventional solvent for such reactions in the art, such as an ether solvent, an alcohol solvent, an amide solvent, a sulfoxide solvent or a mixture thereof. The ether solvent may be, for example, tetrahydrofuran, dioxane or a mixture thereof. The alcohol solvent may be, for example, methanol, ethanol, isopropanol or a mixture thereof. The amide solvent may be, for example, N,N-dimethylformamide, N,N-dimethylacetamide or a mixture thereof. The sulfoxide solvent may be, for example, DMSO. In the preparation method the compound containing the isoquinoline ring represented by formula I, the solvent of the reaction may be a single solvent or a mixture of two or more solvents. In an embodiment of the present disclosure, the solvent is preferably the alcohol solvent, or a mixed solvent of the ether solvent and the alcohol solvent, such as ethanol, or a mixed solvent of tetrahydrofuran and methanol. In the mixed solvent, a volume ratio of the ether solvent to the alcohol solvent may be 0.5:1-4:1, for example, 1:1-2:1. The amount of the solvent may be a conventional amount of the solvent for such reactions in the art. Preferably, the solvent is ethanol, or a mixed solvent of tetrahydrofuran and methanol. More preferably, the solvent is ethanol or a mixed solvent of tetrahydrofuran and methanol with a volume ratio of 1:1 to 2:1. Further preferably, the solvent is ethanol, or a mixed solvent of tetrahydrofuran and methanol with a volume ratio of 2:1.

In the preparation method of the compound containing the isoquinoline ring represented by formula I, the temperature of the reaction may be 60° C. to 70° C.

In the preparation method of the compound containing the isoquinoline ring represented by formula I, the progress of the reaction may be monitored by a conventional detection method in the art (such as TLC, MS, HPLC or NMR, etc.). In the present disclosure, the progress of the reaction is monitored by TLC when the compound M1 disappears as the end point of the reaction.

In the preparation method of the compound containing the isoquinoline ring represented by formula I, after monitoring the completion of the reaction, a conventional post-treatment method in the art may be used for a post-treatment. In the present disclosure, the post-treatment may comprise the following steps: cooling the reaction solution after the completion of the reaction (for example, cooling to 15° C. to 25° C.) and/or adding a poor solvent (for example, isopropyl acetate or methyl tert-butyl ether), performing a solid-liquid separation (for example, filtration under reduced pressure), and drying (for example, draining or vacuum drying) to obtain the target compound I.

The preparation method of the compound containing the isoquinoline ring represented by formula I may further comprise a preparation method of compound M1: carrying out a reaction as shown below between compound SM and compound SM-A under the action of an oxidizing agent to obtain the compound M1;

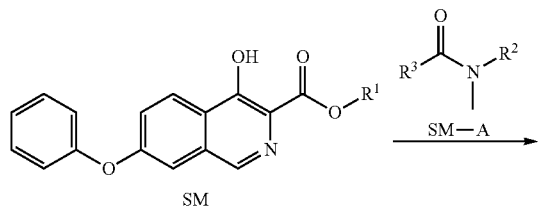

SM

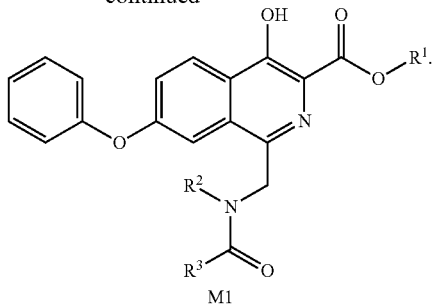

M1 wherein, the definitions of $R^1$ and $R^3$ are the same as above, and $R^2$ is methyl.

Preferably, $R^1$ is H or $C_1$-$C_4$ alkyl; more preferably, $R^1$ is $C_1$-$C_4$ alkyl; further preferably, $R^1$ is methyl, ethyl, n-propyl, isopropyl, n-butyl, isobutyl, sec-butyl or tert-butyl; most preferably, $R^1$ is methyl or ethyl;

preferably, $R^3$ is H or $C_1$-$C_4$ alkyl; more preferably, $R^3$ is H, methyl, ethyl, n-propyl, isopropyl, n-butyl, isobutyl, sec-butyl or tert-butyl; most preferably, $R^3$ is methyl or H.

In the preparation method of compound M1, $R^1$ is methyl or ethyl, $R^2$ is methyl, and $R^3$ is H or methyl.

In the preparation method of compound M1, the oxidizing agent may be a conventional oxidizing agent for such reactions in the art. In the present disclosure, the oxidizing agent may be, for example, a persulfate oxidizing agent, such as an alkali metal persulfate. The alkali metal persulfate may be sodium persulfate, potassium persulfate, potassium peroxymonosulfate composite salt (Oxone) or a mixture thereof. Preferably, the oxidizing agent is sodium persulfate.

In the preparation method of the compound M1, the amount of the oxidizing agent may be a conventional amount of the oxidizing agent for such reactions in the art. In the present disclosure, a molar ratio of the compound SM2 to the oxidizing agent is 1:1-1:5, for example, 1:1.5-1:3, for another example, 1:2.

In the preparation method of the compound M1, the amount of the compound SM and the compound SM-A may be the conventional amount for such reactions in the art. In the present disclosure, a molar ratio of the compound SM-A to the compound SM may be greater than 1:1, for example, greater than 5:1, greater than 10:1, greater than 20:1, greater than 40:1, or greater than 50:1. In principle, in order to control the cost, those skilled in the art know that the amount of the compound SM-A should be controlled within an appropriate range. Preferably, a molar ratio of the compound SM-A to the compound SM is greater than 20:1.

In the preparation method of the compound M1, the solvent may be a conventional solvent for such reactions in the art, such as a chlorinated hydrocarbon solvent, an ether solvent or a mixture thereof. The solvent generally has good solubility for compound SM, and is not easily oxidized or does not participate in the reaction. The compound SM-A may also be used as a reaction solvent and a raw material at the same time. Preferably, compound SM-A is used as both the reaction raw material and the solvent.

In the preparation method of compound M1, the temperature of the reaction may be a conventional temperature for such reactions in the art. In the present disclosure, the reaction temperature may be 30° C. to 100° C., for example, 50° C. to 80° C., and for another example, 60° C. to 70° C.

In an embodiment of the present disclosure, in the preparation method of compound M1, the temperature of the reaction may be 30° C. to 100° C., for example, 60° C. to 70°

C., and for another example, 65° C. to 70° C. Preferably, the temperature of the reaction is 60° C. to ° C.

In the preparation method of compound M1, the oxidizing agent may be directly used alone, or the oxidizing agent is used in the form of a mixed solution with water, or the oxidizing agent is used in the form of a mixed solution with an organic solvent. The water is conventional water in the art, such as purified water, distilled water or a mixture thereof. The organic solvent may be, for example, a chlorinated hydrocarbon solvent, an ether solvent, or a mixture thereof. The organic solvent generally has good solubility for the oxidizing agent. The organic solvent may be, for example, dichloromethane, tetrahydrofuran, dioxane or a mixture thereof. In the mixed solution (a mixed solution with water or a mixed solution with organic solvent), a molar ratio of the oxidizing agent to the water or the organic solvent may be 1:1-1:50, for example, 1:2-1:35, for another example, 1:2-1:30, for still another example, 1:20-1:35, and for yet another example, 1:20-1:30. Preferably, the oxidizing agent is in the form of a mixed solution in which the molar ratio of sodium persulfate to water is 1:20-1:30.

In the preparation method of compound M1, the progress of the reaction may be monitored by a conventional detection method in the art (such as TLC, MS, HPLC or NMR, etc.). In the present disclosure, the progress of the reaction is monitored by TLC when the compound SM2 disappears as the end point of the reaction. The time of the reaction may be, for example, 20 minutes to 10 hours (e.g., 1 hour, 4 hours, 5 hours, 6 hours, or 8 hours).

In the preparation method of compound M1, after monitoring the completion of the reaction, a conventional post-treatment method in the art may be used for a post-treatment. In the present disclosure, the post-treatment may comprise the following steps: extracting the reaction solution after the completion of the reaction with an organic solvent, concentrating the organic phase, optionally slurrying a residue obtained after the concentration with the organic solvent, performing a solid-liquid separation, and optionally washing the solid with the organic solvent and drying to obtain the target compound; or, mixing the reaction solution after the completion of the reaction with water, performing a solid-liquid separation, and optionally washing the solid with the organic solvent and drying to obtain the target compound.

The present disclosure also provides a use of a compound containing an isoquinoline ring represented by formula I or a salt thereof in the quality control of rosalostat synthesis intermediate M2-A

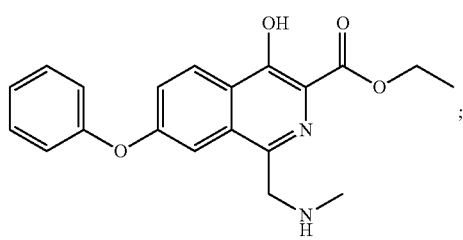

M2-A

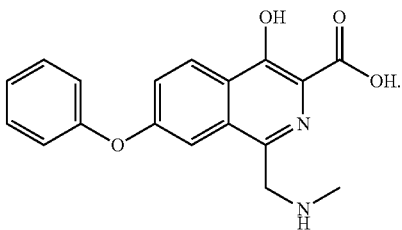

I

In the use, the compound containing the isoquinoline ring represented by formula I or the salt thereof may be used as a reference substance.

In the present disclosure, the term "$C_1$-$C_4$ alkyl" refers to methyl, ethyl, n-propyl, isopropyl, n-butyl, isobutyl, sec-butyl or tert-butyl.

In the present disclosure, the term "$C_1$-$C_4$ alkoxy" refers to methoxy, ethoxy, n-propoxy, isopropoxy, n-butoxy, isobutoxy, sec-butoxy or tert-butoxy.

In the present disclosure, the term $C_1$-$C_4$ alkyl or benzoyl substituted by 1, 2 or 3 halogens means that one or more hydrogens in the $C_1$-$C_4$ alkyl or phenyl are substituted by halogens. For example, trifluoromethyl, difluoromethyl, trifluoroethyl, difluoroethyl or perfluoroethyl.

In the present disclosure, the term "optionally substituted by 1, 2 or 3 R" means that a group is unsubstituted or substituted by 1, 2 or 3 R, wherein R is defined in the present disclosure.

In the present disclosure, the term "halogen" refers to F, Cl, Br or I.

In the present disclosure, the term "hydrochloric acid" refers to a concentrated hydrochloric acid with a mass fraction of about 36%, or a saturated solution of hydrogen chloride in an organic solvent, such as a hydrogen chloride ethanol solution.

In the present disclosure, the term "DMA" refers to N,N-dimethylacetamide;

in the present disclosure, the term "DMF" refers to N,N-dimethylformamide;

In the present disclosure, compound SM may be prepared according to methods known in the prior art, for example, the methods disclosed in CN201210152768.1 and CN201310302822.0. Compound 5 may be prepared according to CN201310302822.0. Compound SM2 may be prepared according to CN201210152768.1.

On the basis of not violating the common sense in the art, the above-mentioned preferred conditions may be arbitrarily combined to obtain the preferred embodiments of the present disclosure.

In the present disclosure, the room temperature generally refers to an ambient temperature, such as 0° C. to 40° C., preferably 10° C. to 30° C., more preferably 25° C.

The reagents and raw materials used in the present disclosure are commercially available.

The positive progressive effect of the present disclosure is that:

The synthesis method of the present disclosure has cheap and easily available raw materials, short steps (only 3 steps are needed to prepare intermediate M3 from the starting raw material SM), mild reaction conditions and a high yield, and is suitable for industrial production. The synthesis method of the present disclosure does not use high-boiling point reagents and noble metal reagents (such as palladium catalysts) that are difficult to remove, and the post-treatment is simple and the three wastes are few. On the other hand, the compound containing the isoquinoline ring in the present disclosure participates in the subsequent reaction, and the derivative impurities of the compound containing the isoquinoline ring are difficult to remove, which has a great impact on the quality of a roxadustat active pharmaceutical ingredient (API). The compound containing the isoquinoline ring may be used as a reference substance to control the quality of roxadustat synthesis intermediates and roxadustat API, which is necessary to control the quality of the roxadustat API and even the drug product.

DETAILED DESCRIPTION OF THE PREFERRED EMBODIMENT

The following embodiments further illustrate the present disclosure, but the present disclosure is not limited thereto. The experimental methods not specified in the specific conditions in the following embodiments are selected according to the conventional methods and conditions, or according to the commodity instructions.

The specific embodiments of a synthesis method of roxadustat and an intermediate thereof in the present disclosure are described in the following embodiments:

In the following embodiments, where a reaction or an operation does not specifically specify the temperature, the reaction or the operation is generally performed at room temperature.

In the following embodiments, a purity refers to a HPLC purity or a GC purity unless otherwise stated.

HPLC purity and impurity detection conditions (embodiments 1-8, unless otherwise stated): chromatographic column: Waters Xbridge C18 3.5 μm 4.6×100 mm; mobile phase: mobile phase A 0.08% formic acid aqueous solution, mobile phase B acetonitrile-water-formic acid=900:100:0.8; mobile phase gradient: 70% A/30% B to 20% A/80% B for 35 min, then 20% A/80% B to 100% B for 4 min, held at 100% B for 10 min, and returned to 70% A/30% B for 1 min, held this gradient for 10 min, for a total of 60 min; flow rate: 1.0 mL/min; wavelength: 295 nm; column temperature: 40° C.

LC-MS detection conditions (embodiments 1-8, unless otherwise stated): model: Agilent liquid chromatography/tandem mass spectrometry 1260/6120; ion source: ESI; sample solvent: acetonitrile.

Embodiment 1 Synthesis of Roxadustat

The synthetic route is as follows:

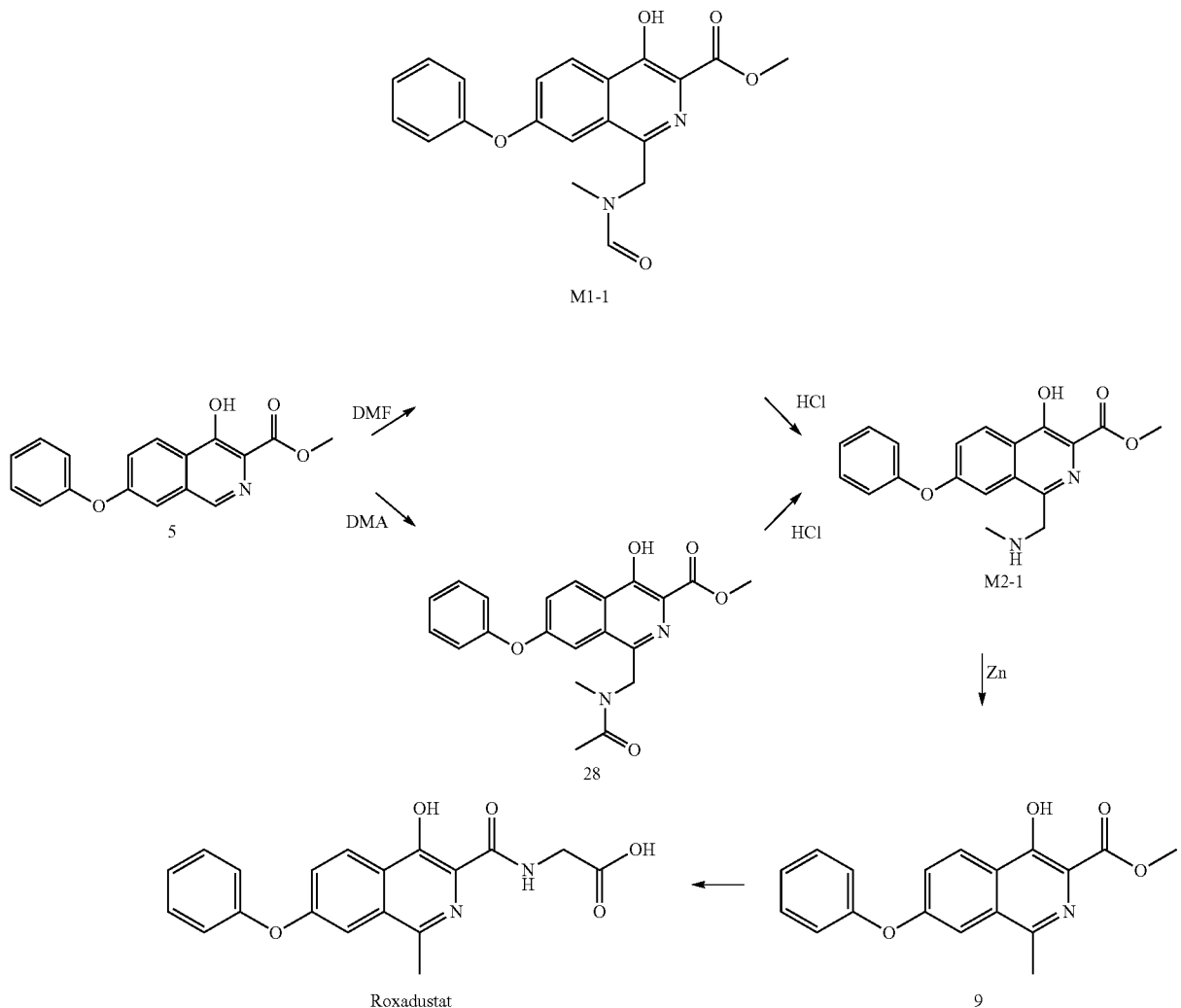

1.1 Synthesis of Intermediate M1-1

2.95 g (0.01 mol) of compound 5 was completely dissolved in 29.5 g (about 0.4 mol) of N, N-dimethylformamide (DMF) by heating to 60° C. to 70° C. 4.76 g (0.02 mol) of sodium persulfate was dissolved in 9.6 g (about 0.53 mol) of water and then added to the above solution, and the obtained mixture was stirred for 6 hours. The completion of the reaction was monitored by TLC. The reaction solution was cooled to room temperature, and ethyl acetate (80 mL) was added thereto, and the mixture was washed with water (40 mL×4). An organic phase was concentrated to a volume of 8-10 mL, filtered under reduced pressure, washed with a small amount of ethyl acetate, and the filter cake was dried in vacuum to obtain 2.7 g of a white solid with a yield of 73.5% and a purity of 97.22%.

MS (ESI) m/z: 367.1 [M+1]$^+$, $^1$H-NMR (400 MHz, DMSO-d$_6$) δ 11.62 (s, 1H), 8.38 (t, J=8.1 Hz, 1H), 8.11 (d, J=58.9 Hz, 1H), 7.72 (d, J=22.0 Hz, 1H), 7.44-7.58 (m, 3H), 7.26 (dd, J=16.0, 7.8 Hz, 1H), 7.12-7.18 (m, 2H), 4.86 (d, J=34.9 Hz, 2H), 3.96 (d, J=5.0 Hz, 3H), 2.73 (d, J=48.0 Hz, 3H).

1.2 Synthesis of Intermediate 28

29.5 g (0.1 mol) of compound 5 was completely dissolved in 295 g (about 3.4 mol) of N,N-dimethylacetamide (DMA) by heating to 60° C. to 70° C. 47.6 g (0.2 mol) of sodium persulfate was dissolved in 95.2 g (about 5.3 mol) of water and then added to the above solution, and the obtained mixture was stirred for 20 minutes. The completion of the reaction was monitored by TLC. The reaction solution was cooled to room temperature. 500 g of water was added to the solution, and the mixture was stirred and then filtered under reduced pressure, and the filter cake was dried in vacuum to obtain 34.1 g of a white solid with a yield of 89.6% and a purity of 96.6%.

MS(ESI) m/z: 381.2 [M+1]$^+$, $^1$H-NMR (400 MHz, DMSO-d$_6$) δ 11.58 (s, 1H), 8.36 (t, J=8.9 Hz, 1H), 7.68 (d, J=33.4 Hz, 1H), 7.42-7.58 (m, 3H), 7.11-7.30 (m, 3H), 4.90 (d, J=36.0 Hz, 2H), 3.97 (d, J=10.3 Hz, 3H), 2.86 (d, J=25.7 Hz, 3H), 1.97 (d, J=17.8 Hz, 3H).

1.3 Synthesis of Intermediate M2-1

3.0 g (about 0.008 mol) of intermediate M1-1 was dissolved in a mixed solution of tetrahydrofuran (10 mL) and methanol (5 mL) by heating to 30° C. to 40° C. A concentrated hydrochloric acid (5 mL, hydrochloric acid with a mass fraction of 36%) was added while stirring, and the stirring was continued for 16 hours. The completion of the reaction was monitored by TLC. The reaction solution was concentrated in vacuum to a concentrated solution with a volume of about 3-5 mL to precipitate a solid, filtered under reduced pressure, washed with a small amount of methanol, and the filter cake was dried in vacuum to obtain 2.7 g of a white solid with a yield of 88.7% (calculated on the basis of hydrochloride salt) and a purity of 98.64%.

MS(ESI) m/z: 339.1 [M+1]$^+$, $^1$H-NMR (400 MHz, DMSO-d$_6$) δ 11.62 (s, 1H), 9.21 (s, 2H), 8.41 (d, J=9.0 Hz, 1H), 7.72 (s, 1H), 7.59 (d, J=9.1 Hz, 1H), 7.47 (t, J=7.2 Hz, 2H), 7.26 (t, J=7.1 Hz, 1H), 7.17 (d, J=7.5 Hz, 2H), 4.66 (s, 2H), 3.99 (s, 3H), 2.71 (s, 3H).

1.4 Synthesis of Intermediate M2-1

30.0 g (about 0.079 mol) of intermediate 28 was dissolved in a mixed solvent of tetrahydrofuran (100 mL) and methanol (50 mL) by heating to 30° C. to 40° C. A concentrated hydrochloric acid (50 mL, hydrochloric acid with a mass fraction of 36%) was added while stirring, and the stirring was continued for 16 hours. The completion of the reaction was monitored by TLC. The reaction solution was concentrated in vacuum until a large amount of solid precipitated, filtered under reduced pressure, washed with a small amount of methanol, and the filter cake was dried in vacuum to obtain 27.1 g of a white solid with a yield of 91.8% (calculated on the basis of hydrochloride salt) and a purity of 98.20%.

MS (ESI) m/z: 339.1 [M+1]$^+$, $^1$H-NMR (400 MHz, DMSO-d$_6$) δ 11.62 (s, 1H), 9.21 (s, 2H), 8.41 (d, J=9.0 Hz, 1H), 7.72 (s, 1H), 7.59 (d, J=9.1 Hz, 1H), 7.47 (t, J=7.2 Hz, 2H), 7.26 (t, J=7.1 Hz, 1H), 7.17 (d, J=7.5 Hz, 2H), 4.66 (s, 2H), 3.99 (s, 3H), 2.71 (s, 3H).

1.5 Synthesis of Intermediate 9

25.0 g (about 0.074 mol) of intermediate M2-1 was dissolved in an acetic acid (250 g), then 26.1 g of zinc powder was added, and the mixture was heated to 50° C. to 60° C. and stirred for 6 hours. The completion of the reaction was monitored by TLC. The reaction solution was filtered, and the filter cake was washed twice with a mixed solvent of dichloromethane (50 mL) and methanol (25 mL). The filtrates were combined and then concentrated to a concentrated solution with a volume of about 10-15 mL. Isopropanol (25 mL) and water (50 mL) were added, and the mixture was stirred and then filtered under reduced pressure. The filter cake was slurried in methanol/water (1:3/v:v, 75 mL), filtered under reduced pressure and the filter cake was dried in vacuum to obtain 15.6 g of a brown solid with a yield of 75.3% and a purity of 96.57%.

MS (ESI) m/z: 310.1 [M+1]$^+$, $^1$H-NMR (400 MHz, DMSO-d$_6$) δ 11.45 (s, 1H), 8.25 (d, J=8.9 Hz, 1H), 7.55-7.39 (m, 4H), 7.24 (t, J=7.3 Hz, 1H), 7.16 (d, J=7.9 Hz, 2H), 3.93 (s, 3H), 2.58 (s, 3H).

1.6 Synthesis of Roxadustat 15.0 g (about 0.05 mol) of intermediate 9 was added to methanol (150 g), then 14.1 g of sodium glycinate was added, and the mixture was heated to 105° C. to 115° C. in a pressure-resistant container and stirred for 8 hours with sealing. The reaction solution was cooled to room temperature, filtered under reduced pressure, washed with a small amount of methanol, and then drained to obtain a crude product of a roxadustat sodium salt. The crude product of the roxadustat sodium salt was dissolved in 90 mL of water, and an aqueous phase was washed with 40 mL of ethyl acetate. Under stirring, an acetic acid was slowly added to the aqueous phase to adjust the pH to less than 7, and a large amount of solid was precipitated, filtered under reduced pressure. The filter cake was washed with water, dried in vacuum to obtain 14.1 g of a finished product of roxadustat with a yield of 82.6% and a purity of 99.47%.

MS (ESI) m/z: 353.2 [M+H]$^+$, $^1$H-NMR (400 MHz, DMSO-d$_6$) δ 13.28 (s, 1H), 9.08 (t, J=5.8 Hz, 1H), 8.25 (t, J=12.0 Hz, 1H), 7.59 (s, 1H), 7.55-7.41 (m, 3H), 7.24 (t, J=7.3 Hz, 1H), 7.16 (d, J=7.9 Hz, 2H), 4.04 (d, J=5.9 Hz, 2H), 2.68 (s, 3H).

Embodiment 2 Synthesis of Intermediate 9

The synthetic route is as follows:

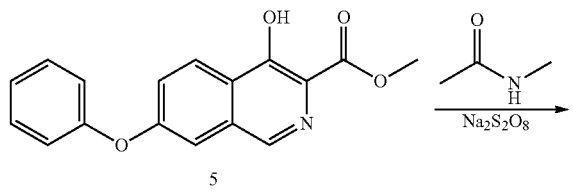

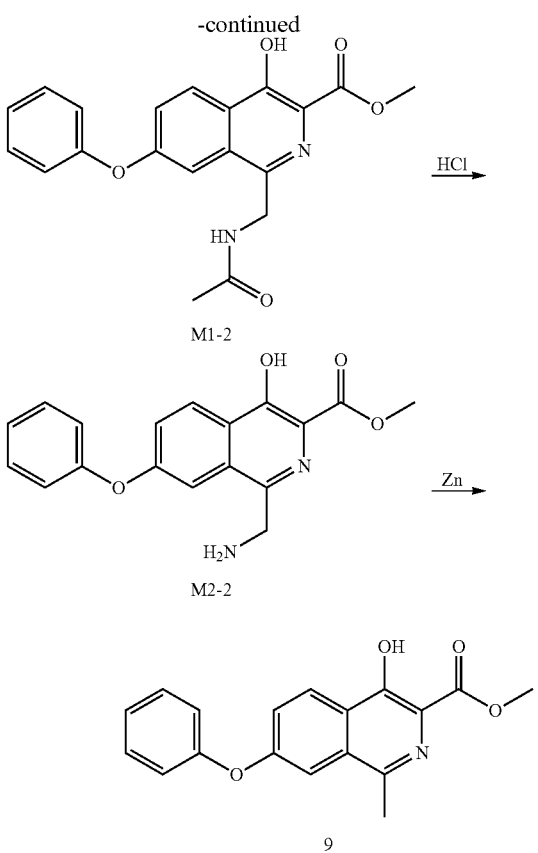

2.1 Synthesis of Intermediate M1-2

2.95 g (0.01 mol) of compound 5 was completely dissolved in 29.5 g (about 0.4 mol) of N-methylacetamide by heating to 60° C. to 70° C. 4.76 g (0.02 mol) of sodium persulfate was dissolved in 9.6 g (about 0.53 mol) of water and then added to the above solution, and the mixture was stirred for 8 hours. The completion of the reaction was monitored by TLC. The reaction solution was cooled to room temperature, ethyl acetate (80 mL) was added, and the mixture was washed with water (30 mL×4). An organic phase was concentrated to a volume of about 8-10 mL, filtered under reduced pressure, washed with a small amount of ethyl acetate, and drained to obtain 2.4 g of a white solid with a yield of 65.0% and a purity of 98.76%.

MS (ESI) m/z: 367.2 [M+1]$^+$, $^1$H-NMR (400 MHz, DMSO-d$_6$) δ 11.59 (s, 1H), 8.36 (t, J=7.3 Hz, 2H), 7.71 (s, 1H), 7.56 (d, J=9.0 Hz, 1H), 7.46 (t, J=7.4 Hz, 2H), 7.25 (t, J=7.3 Hz, 1H), 7.14 (d, J=7.7 Hz, 2H), 4.62 (d, J=5.0 Hz, 2H), 3.97 (s, 3H), 1.76 (s, 3H).

2.2 Synthesis of Intermediate M2-2

2.0 g (about 0.0055 mol) of intermediate M1-2 was dissolved in tetrahydrofuran (10 mL) and methanol (5 mL) by heating to 30° C. to 40° C. A concentrated hydrochloric acid (5 mL, hydrochloric acid with a mass fraction of 36%) was added while stirring, and the mixture was stirred for 16 hours. The completion of the reaction was monitored by TLC. The reaction solution was concentrated in vacuum to obtain a concentrated solution with a volume of about 2-3 mL to precipitate a solid, filtered under reduced pressure, washed with a small amount of methanol, and drained to obtain 1.7 g of a white solid with a yield of 83.3% (calculated on the basis of hydrochloride salt) and a purity of 97.80%.

MS (ESI) m/z: 325.1 [M+1]$^+$, $^1$H-NMR (400 MHz, DMSO-d$_6$) δ 11.62 (s, 1H), 8.51-8.39 (m, 4H), 7.75 (s, 1H), 7.60 (d, J=9.0 Hz, 1H), 7.49 (t, J=7.4 Hz, 2H), 7.27 (t, J=7.3 Hz, 1H), 7.18 (d, J=7.7 Hz, 2H), 4.53 (s, 2H), 4.00 (s, 3H).

2.3 Synthesis of Intermediate 9

1.5 g (about 0.0046 mol) of intermediate M2-2 was dissolved in an acetic acid (15 mL), then 0.81 g of zinc powder was added, and the mixture was heated to 50° C. to 60° C. and stirred for 3 hours. The completion of the reaction was monitored by TLC. The reaction solution was filtered, and the filter cake was washed twice with a mixed solvent of dichloromethane (10 mL) and methanol (5 mL). The filtrates were combined and then concentrated to a concentrated solution with a volume of about 2-3 mL. Isopropanol (3 mL) and water (6 mL) were added, and the mixture was stirred and then filtered under reduced pressure. The filter cake was slurried in methanol/water (1:3/v:v, 9 mL), and filtered under reduced pressure to obtain 1.1 g of intermediate 9 with a yield of 74.4% and a purity of 96.23%.

MS (ESI) m/z: 310.1 [M+1]$^+$, $^1$H-NMR (400 MHz, DMSO-d$_6$) δ 11.47 (s, 1H), 8.30 (d, J=9.0 Hz, 1H), 7.56 (s, 1H), 7.54-7.42 (m, 3H), 7.25 (t, J=7.3 Hz, 1H), 7.17 (d, J=7.9 Hz, 2H), 3.94 (s, 3H), 2.61 (s, 3H).

Embodiment 3 Synthesis of Roxadustat

The synthetic route is as follows:

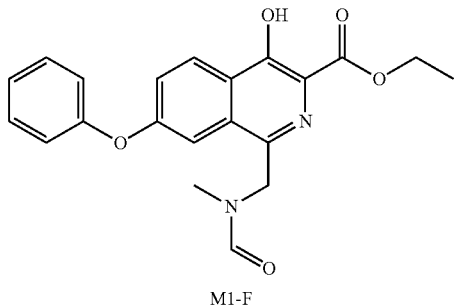

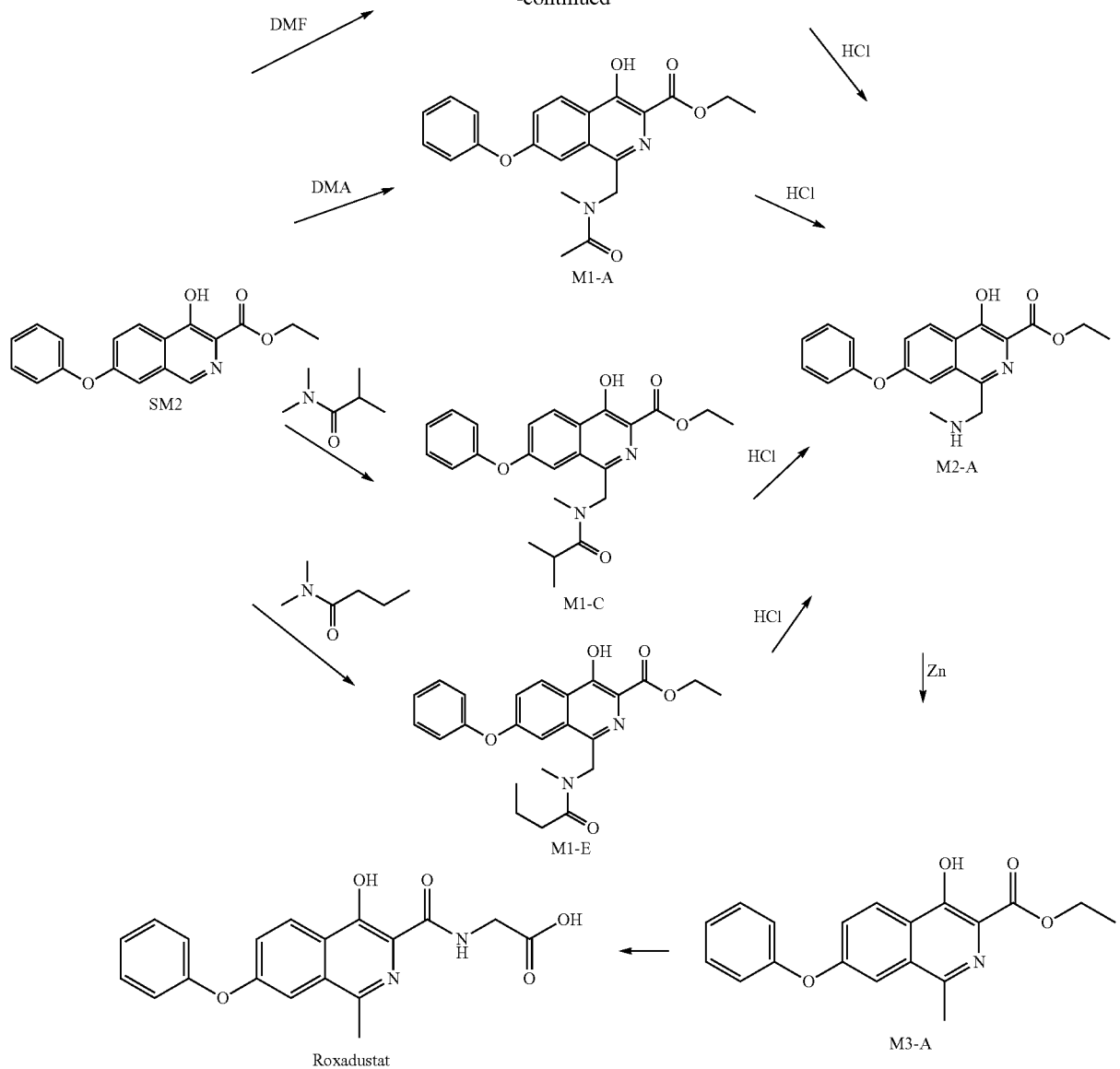

3.1 Synthesis of Intermediate M1-A 3.1 g (about 0.01 mol) of compound SM2 was completely dissolved in 31.0 g (about 0.36 mol) of N, N-dimethylacetamide (DMA) by heating to 60° C. to 70° C. 4.8 g (about 0.02 mol) of sodium persulfate was dissolved in 9.6 g (about 0.53 mol) of water and then added to the above solution, and the obtained mixture was stirred for 1 hour. The completion of the reaction was monitored by TLC. The reaction solution was cooled to room temperature. 50 g of water was added to the solution, and the mixture was stirred and then filtered under reduced pressure, and the filter cake was dried in vacuum to obtain 3.3 g of an off-white solid with a yield of 85.7% and a purity of 98.46%.

MS (ESI) m/z: 417.16 [M+Na]$^+$, $^1$H-NMR (400 MHz, DMSO-$d_6$) δ 11.66 (d, J=22.8 Hz, 1H), 8.32 (t, J=9.0 Hz, 1H), 7.68 (dd, J=14.5, 2.2 Hz, 1H), 7.44-7.57 (m, 3H), 7.12-7.30 (m, 3H), 4.88 d, J=34.0 Hz, 2H), 4.44 (q, J=14.0, 7.0 Hz, 2H), 2.83 (d, J=40.0 Hz, 3H), 1.97 (d, J=8.3 Hz, 3H), 1.39 (t, J=7.1 Hz, 3H).

3.2 Synthesis of Intermediate M1-C 3.1 g (about 0.01 mol) of compound SM2 was completely dissolved in 31.0 g (about mol) of N,N-dimethylisobutyramide by heating to 60° C. to 70° C. 4.8 g (0.02 mol) of sodium persulfate was dissolved in 9.6 g (about 0.53 mol) of water and then added to the above solution, and the obtained mixture was stirred for 5 hours. The completion of the reaction was monitored by TLC. The reaction solution was cooled to room temperature, and ethyl acetate (80 mL) was added, and the mixture was washed with water (50 mL×4). The organic phase was concentrated. The residue was slurried with a mixed solvent (12 mL) of ethyl acetate and n-heptane (1:2/v:v), and then filtered under reduced pressure, then the filter cake was dried in vacuum to obtain 2.7 g of an off-white solid with a yield of 64.2% and a purity of 97.55%.

MS (ESI) m/z: 423.2 [M+H]$^+$, $^1$H-NMR (400 MHz, DMSO-$d_6$) δ 11.66 (d, J=18.0, 1H), 8.32 (t, J=8.1 Hz, 1H), 7.70 (d, J=31.0 Hz, 1H), 7.41-7.54 (m, 3H), 7.22 (t, J=7.2 Hz, 1H), 7.13 (dd, J=17.8, 7.9 Hz, 2H), 4.94 (d, J=56.0 Hz, 2H), 4.48 (q, J=14.0, 7.0 Hz, 2H), 2.94 (s, 3H), 2.85 (m, 1H), 1.33 (t, J=7.0 Hz 3H), 0.94-1.00 (m, 6H).

3.2 Synthesis of Intermediate M1-E 3.1 g (about 0.01 mol) of compound SM2 was completely dissolved in 31.0 g (about 0.27 mol) of N,N-dimethyl-n-butyramide by heating to 60° C. to 70° C. 4.8 g (about 0.02 mol) of sodium persulfate was dissolved in 9.6 g (about 0.53 mol) of water and then added to the above solution, and the obtained mixture was stirred for 4 hours. The completion of the reaction was monitored by TLC. The reaction solution was cooled to room temperature, then ethyl acetate (80 mL) was added, and the mixture was washed with water (50 mL×4). The organic phase was concentrated. The residue was slurried with a mixed solvent (12 mL) of ethyl acetate and n-heptane (1:2/v:v) and then filtered under reduced pressure, then the filter cake was dried in vacuum to obtain 2.8 g of an off-white solid with a yield of 66.7% and a purity of 98.08%.

MS (ESI) m/z: 445.3 [M+Na]$^+$, $^1$H-NMR (400 MHz, DMSO-d$_6$) δ 11.62 (d, J=20.3 Hz, 1H), 8.33 (t, J=8.2 Hz, 1H), 7.68 (d, J=14.5 Hz, 1H), 7.39-7.56 (m, 3H), 7.06-7.25 (m, 3H), 4.85 (s, 2H), 4.41 (dd, J=14.2 7.1 Hz, 2H), 2.86 (s, 3H), 2.23 (t, J=7.2 Hz 2H), 1.46 (m, 2H), 1.34 (t, J=7.0 Hz 3H), 0.83 (t, J=7.3 Hz 3H).

3.4 Synthesis of Intermediate M1-F 3.1 g (about 0.01 mol) of compound SM2 was completely dissolved in 31.0 g (about mol) of N,N-dimethylformamide by heating to 65° C. to 70° C. 4.8 g (about 0.02 mol) of sodium persulfate was dissolved in 9.6 g (about 0.53 mol) of water and then added to the above solution, and the obtained mixture was stirred for 4 hours. The completion of the reaction was monitored by TLC. The reaction solution was cooled to room temperature. 50 g of water was added to the solution, stirred and then filtered under reduced pressure, and the filter cake was dried in vacuum to obtain 2.8 g of an off-white solid with a yield of 72.3% and a purity of 99.79%.

MS (ESI) m/z: 403.1 [M+Na]$^+$, $^1$H-NAIR (400 MHz, DMSO-d$_6$) δ 11.67 (s, 1H), 8.29-8.41 (m, 1H), 8.09 (d, J=59.1 Hz, 1H), 7.69 (d, J=17.7 Hz, 1H), 7.41-7.51 (m, 3H), 7.24 (t, J=7.8 Hz, 1H), 7.07-7.18 (m, 2H), 4.83 (d, J=35.8 Hz, 2H), 4.41 (dd, J=14.2 7.1 Hz, 2H), 2.71 (d, J=44.0 Hz, 3H), 1.35 (t, J=7.1 Hz 3H).

3.5 Synthesis of Intermediate M2-A 3.0 g (about 0.008 mol, prepared in embodiment 3.1) of intermediate M1-A was dissolved in tetrahydrofuran (10 mL) and methanol (5 mL) by heating to 30° C. to 40° C. A concentrated hydrochloric acid (5 mL, hydrochloric acid with a mass fraction of 36%) was added while stirring, and the obtained mixture was stirred for 5 hours. The completion of the reaction was monitored by TLC. The reaction solution was concentrated in vacuum until a large amount of solid precipitated, filtered under reduced pressure, washed with a small amount of methanol, and drained to obtain 2.8 g of a white solid with a yield of 94.7% (calculated on the basis of hydrochloride salt) and a purity of 98.40%; wherein the content of impurity compound I (retention time was 4.95 min) was 1.4%.

MS (ESI) m/z: 353.16 [M+H]$^+$, $^1$H-NMR (400 MHz, DMSO-d$_6$) δ 11.72 (s, 1H), 9.32 (s, 2H), 8.42 (d, J=9.1 Hz, 1H), 7.75 (d, J=2.2 Hz, 1H), 7.60 (dd, J=9.1, 2.3 Hz, 1H), 7.49 (t, J=7.9 Hz, 2H), 7.27 (t, J=7.4 Hz, 1H), 7.19 (d, J=7.7 Hz, 2H), 4.67 (s, 2H), 4.50 (q, J=7.1 Hz, 2H), 2.74 (s, 3H), 1.41 (t, J=7.1 Hz, 3H).

3.6 Synthesis of Intermediate M2-A 3.0 g (about 0.007 mol) of intermediate M1-C was dissolved in tetrahydrofuran (10 mL) and methanol (10 mL) by heating to 30° C. to 40° C. A concentrated hydrochloric acid (5 mL, hydrochloric acid with a mass fraction of 36%) was added while stirring, and the obtained mixture was stirred for 8 hours. The completion of the reaction was monitored by TLC. The reaction solution was concentrated in vacuum until a large amount of solid precipitated, filtered under reduced pressure, washed with a small amount of methanol, and drained to obtain 2.4 g of a white solid with a yield of 88.4% (calculated on the basis of hydrochloride salt) and a purity of 98.18%.

MS (ESI) m/z: 353.16 [M+H]$^+$, $^1$H-NMR (400 MHz, DMSO-d$_6$) δ 11.72 (s, 1H), 9.32 (s, 2H), 8.42 (d, J=9.1 Hz, 1H), 7.75 (d, J=2.2 Hz, 1H), 7.60 (dd, J=9.1, 2.3 Hz, 1H), 7.49 (t, J=7.9 Hz, 2H), 7.27 (t, J=7.4 Hz, 1H), 7.19 (d, J=7.7 Hz, 2H), 4.67 (s, 2H), 4.50 (q, J=7.1 Hz, 2H), 2.74 (s, 3H), 1.41 (t, J=7.1 Hz, 3H).

3.7 Synthesis of Intermediate M2-A 3.0 g (about 0.007 mol) of intermediate M1-E was dissolved in tetrahydrofuran (10 mL) and methanol (10 mL) by heating to 30° C. to 40° C. A concentrated hydrochloric acid (5 mL, hydrochloric acid with a mass fraction of 36%) was added while stirring, and the stirring was continued for 8 hours after the addition. The completion of the reaction was monitored by TLC. The reaction solution was concentrated in vacuum until a large amount of solid precipitated, filtered under reduced pressure, washed with a small amount of methanol, and drained to obtain 2.4 g of a white solid with a yield of 86.2% (calculated on the basis of hydrochloride salt) and a purity of 98.83%.

MS (ESI) m/z: 353.16 [M+H]$^+$, $^1$H-NMR (400 MHz, DMSO-d$_6$) δ 11.72 (s, 1H), 9.32 (s, 2H), 8.42 (d, J=9.1 Hz, 1H), 7.75 (d, J=2.2 Hz, 1H), 7.60 (dd, J=9.1, 2.3 Hz, 1H), 7.49 (t, J=7.9 Hz, 2H), 7.27 (t, J=7.4 Hz, 1H), 7.19 (d, J=7.7 Hz, 2H), 4.67 (s, 2H), 4.50 (q, J=7.1 Hz, 2H), 2.74 (s, 3H), 1.41 (t, J=7.1 Hz, 3H).

3.8 Synthesis of Intermediate M2-A 3.0 g (about 0.008 mol) of intermediate M1-F was dissolved in tetrahydrofuran (10 mL) and methanol (10 mL) by heating to 30° C. to 40° C. A concentrated hydrochloric acid (5 mL, hydrochloric acid with a mass fraction of 36%) was added while stirring, and the obtained mixture was stirred for 8 hours. The completion of the reaction was monitored by TLC. The reaction solution was concentrated in vacuum until a large amount of solid precipitated, filtered under reduced pressure, washed with a small amount of methanol, and drained to obtain 2.6 g of a white solid with a yield of 84.5% (calculated on the basis of hydrochloride salt) and a purity of 98.11%.

MS (ESI) m/z: 353.16 [M+H]$^+$, $^1$H-NMR (400 MHz, DMSO-d$_6$) δ 11.72 (s, 1H), 9.32 (s, 2H), 8.42 (d, J=9.1 Hz, 1H), 7.75 (d, J=2.2 Hz, 1H), 7.60 (dd, J=9.1, 2.3 Hz, 1H), 7.49 (t, J=7.9 Hz, 2H), 7.27 (t, J=7.4 Hz, 1H), 7.19 (d, J=7.7 Hz, 2H), 4.67 (s, 2H), 4.50 (q, J=7.1 Hz, 2H), 2.74 (s, 3H), 1.41 (t, J=7.1 Hz, 3H).

3.9 Synthesis of Intermediate M3-A 2.5 g (about 0.007 mol, prepared in embodiment 3.5) of intermediate M2-A was dissolved in an acetic acid (25 mL). 2.6 g (0.04 mol) of zinc powder was added, and the obtained mixture was heated to 50° C. to 60° C. and stirred for 6 hours. The completion of the reaction was monitored by TLC. The reaction solution was filtered, and the filter cake was washed with a mixed solvent of dichloromethane (20 mL) and methanol (10 mL). The filtrates were combined and then concentrated to a small amount of solvent (for example, the volume of the concentrated solution was about 2-3 mL). Isopropanol (4 mL) and water (8 mL) were added, and the mixture was stirred and filtered under reduced pressure. The filter cake was slurried in methanol/water (1:3/v:v, 12 mL)

and filtered under reduced pressure to obtain 1.6 g of an off-white solid with a yield of 76.7% and a purity of 96.90%, wherein the content of impurity compound II (retention time was 6.8 min) was 1.2%.

MS (ESI) m/z: 346.10 [M+Na]$^+$, $^1$H-NMR (400 MHz, DMSO-d$_6$) δ 11.63 (s, 1H), 8.32 (d, J=9.0 Hz, 1H), 7.58 (d, J=2.0 Hz, 1H), 7.55-7.44 (m, 3H), 7.27 (t, J=7.4 Hz, 1H), 7.19 (d, J=7.9 Hz, 2H), 4.44 (q, J=7.1 Hz, 2H), 2.64 (s, 3H), 1.37 (q, J=7.3 Hz, 3H).

3.10 Synthesis of Roxadustat

Synthesis Method 1 of Roxadustat:

1.5 g of intermediate M3-A (prepared in embodiment 3.9) was added to 15 g of ethanol, and 1.4 g of sodium glycinate was added, and the obtained mixture was heated to 105° C. to 115° C. in a pressure-resistant container and stirred for 8 hours with sealing. The reaction solution was cooled to room temperature, filtered under reduced pressure, washed with a small amount of methanol, and drained to obtain a crude product of a roxadustat sodium salt. The crude product of the roxadustat sodium salt was dissolved in 25 g of water, and the aqueous phase was washed with 10 mL of ethyl acetate. Under stirring, an acetic acid was slowly added to the aqueous phase to adjust the pH to less than 7, and a large amount of solid was precipitated, filtered under reduced pressure. The filter cake was washed with water and drained, dried in vacuum to obtain 1.3 g of a finished product of roxadustat with a yield of 83.4% and a purity of 99.57%, wherein the content of impurity compound II (retention time was 6.8 min) was 0.41%.

MS (ESI) m/z: 353.2 [M+H]$^+$, $^1$H-NMR (400 MHz, DMSO-d$_6$) δ 13.28 (s, 1H), 9.08 (t, J=5.8 Hz, 1H), 8.25 (t, J=12.0 Hz, 1H), 7.59 (s, 1H), 7.55-7.41 (m, 3H), 7.24 (t, J=7.3 Hz, 1H), 7.16 (d, J=7.9 Hz, 2H), 4.04 (d, J=5.9 Hz, 2H), 2.68 (s, 3H).

Synthesis Method 2 of Roxadustat:

3.2 g of intermediate M3-A, 1.5 g of glycine and 3.0 g of 1,8-diazabicycloundec-7-ene were successively added to 32 mL of acetonitrile, and the obtained mixture was heated to 60° C. and stirred for 3 hours. The reaction solution was cooled to room temperature, concentrated under reduced pressure in vacuum until the volume of the concentrated solution was about 3-5 mL. 32 mL of water was added, and 2.4 g of an acetic acid was added dropwise to the aqueous phase under stirring, and a solid was precipitated, then the mixture was filtered under reduced pressure. The filter cake was washed with water (10 mL×3) and drained. The filter cake was transferred to methanol/water (6 mL/18 mL), stirred at room temperature for hours, filtered under reduced pressure, and dried in vacuum to obtain 3.1 g of a finished product of roxadustat with a yield of 87.5% and a purity of 99.18%.

MS (ESI) m/z: 353.2 [M+H]$^+$, $^1$H-NMR (400 MHz, DMSO-d$_6$) δ 13.28 (s, 1H), 9.08 (t, J=5.8 Hz, 1H), 8.25 (t, J=12.0 Hz, 1H), 7.59 (s, 1H), 7.55-7.41 (m, 3H), 7.24 (t, J=7.3 Hz, 1H), 7.16 (d, J=7.9 Hz, 2H), 4.04 (d, J=5.9 Hz, 2H), 2.68 (s, 3H).

Synthesis Method 3 of Roxadustat:

3.2 g of intermediate M3-A and 2.9 g of sodium glycinate were added to 32 mL of absolute ethanol, and the obtained mixture was heated to reflux, and kept stirring for 8 hours. The reaction solution was cooled to room temperature, concentrated under reduced pressure until the volume of the concentrated solution was about 3-5 mL. 45 mL of water was added, and the aqueous phase was washed with ethyl acetate (10 mL×2). 2.4 g of an acetic acid was added dropwise to the aqueous phase under stirring, and a solid was precipitated, and the mixture was filtered under reduced pressure. The filter cake was transferred to methanol/water (6 mL/18 mL), stirred at room temperature for 0.5 hours, filtered under reduced pressure, and dried in vacuum to obtain 3.0 g of a finished product of roxadustat with a yield of 86.4% and a purity of 99.34%.

MS (ESI) m/z: 353.2 [M+H]$^+$, $^1$H-NMR (400 MHz, DMSO-d$_6$) δ 13.28 (s, 1H), 9.08 (t, J=5.8 Hz, 1H), 8.25 (t, J=12.0 Hz, 1H), 7.59 (s, 1H), 7.55-7.41 (m, 3H), 7.24 (t, J=7.3 Hz, 1H), 7.16 (d, J=7.9 Hz, 2H), 4.04 (d, J=5.9 Hz, 2H), 2.68 (s, 3H).

Embodiment 4 Synthesis of Intermediate M3-A

The synthetic route is as follows:

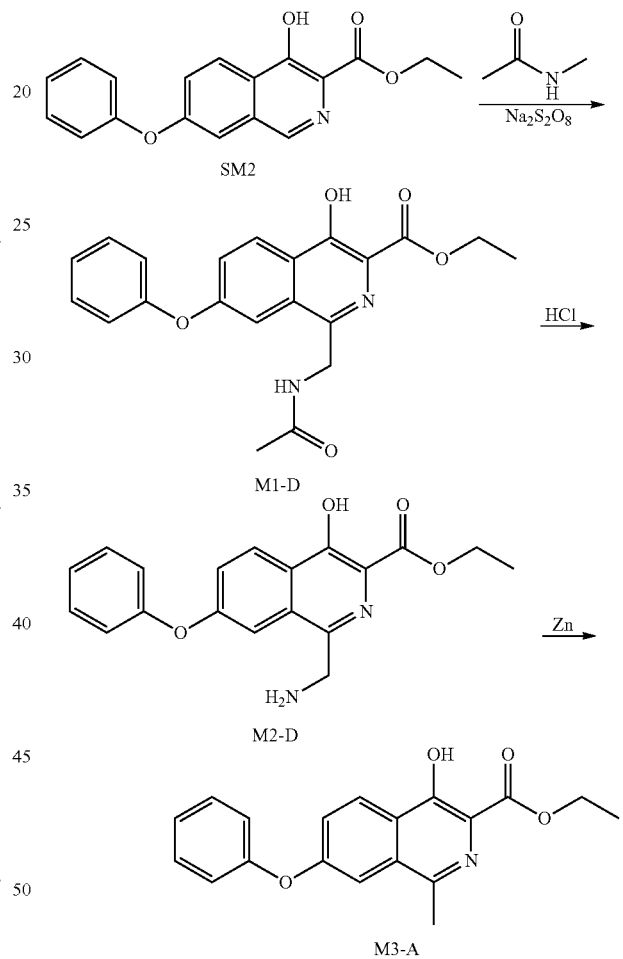

4.1 Synthesis of Intermediate M1-D 3.1 g (about 0.01 mol) of compound SM2 was completely dissolved in 31.0 g (about mol) of N-methylacetamide by heating to 65° C. to 70° C. 4.8 g (about 0.02 mol) of sodium persulfate was dissolved in 9.6 g (about 0.53 mol) of water and then added to the above solution, and the obtained mixture was stirred for 5 hours. A small amount of raw materials remained were monitored by TLC. The reaction solution was cooled to room temperature, and ethyl acetate (80 mL) was added, and the mixture was washed with water (50 mL×4). The organic phase was concentrated. The residue was slurried with a mixed solvent (12 mL) of ethyl acetate and n-heptane (1:2/v:v) and then filtered under reduced pressure, then the filter cake was dried in vacuum to obtain 2.3 g of an off-white solid with a yield of 73.5% and a purity of 95.61%.

MS (ESI) m/z: 403.1 [M+Na]$^+$, $^1$H-NMR (400 MHz, DMSO-d$_6$) δ 11.66 (s, 1H), 8.33 (d, J=9.0 Hz, 2H), 7.67 (s, 1H), 7.53 (dd, J=9.1, 1.9 Hz, 1H), 7.44 (t, J=7.8 Hz, 2H), 7.22 (t, J=7.4 Hz, 1H), 7.12 (d, J=7.9 Hz, 2H), 4.59 (d, J=5.5 Hz, 2H), 4.43 (q, J=7.1 Hz, 2H), 1.74 (s, 3H), 1.36 (t, J=7.1 Hz, 3H).

4.2 Synthesis of Intermediate M2-D 3.0 g (about 0.008 mol) of intermediate M1-D was dissolved in tetrahydrofuran (10 mL) and methanol (10 mL) by heating to 30° C. to 40° C. A concentrated hydrochloric acid (5 mL, hydrochloric acid with a mass fraction of 36%) was added while stirring, and the stirring was continued for 5 hours after the addition. The completion of the reaction was monitored by TLC. The reaction solution was concentrated in vacuum to a concentrated solution with a volume of about 2-4 mL, a large amount of solid was precipitated, and the mixture was filtered under reduced pressure. The filter cake was dried in vacuum to obtain 2.8 g of a white solid with a yield of 92.4% (calculated on the basis of hydrochloride salt) and a purity of 88.40%.

MS (ESI) m/z: 339.1 [M+H]$^+$, $^1$H-NMR (400 MHz, DMSO-d$_6$) δ 11.69 (s, 1H), 8.39 (d, J=9.2 Hz, 4H), 7.73 (s, 1H), 7.57 (d, J=9.1 Hz, 1H), 7.46 (t, J=7.8 Hz, 2H), 7.25 (t, J=7.4 Hz, 1H), 7.16 (d, J=7.9 Hz, 2H), 7.44-7.52 (m, 4H), 1.38 (t, J=7.1 Hz, 3H).

4.3 Synthesis of Intermediate M3-A 2.5 g (about 0.007 mol) of intermediate M2-D was dissolved in an acetic acid (25 mL), then 2.6 g of zinc powder was added, and the obtained mixture was heated to 50° C. to 60° C. and stirred for 6 hours. The completion of the reaction was monitored by TLC. The reaction solution was filtered, and the filter cake was dissolved by stirring with a mixed solvent of dichloromethane (20 mL) and methanol (10 mL). The zinc powder was removed by filtering under reduced pressure, and the organic phase was concentrated until a large amount of solid was precipitated. 1.6 g of off-white solid with a yield of 72.1% and a purity of 92.94% was obtained by filtering under reduced pressure.

MS (ESI) m/z: 346.10 [M+Na]$^+$, $^1$H-NMR (400 MHz, DMSO-d$_6$) δ 11.63 (s, 1H), 8.32 (d, J=9.0 Hz, 1H), 7.58 (d, J=2.0 Hz, 1H), 7.55-7.44 (m, 3H), 7.27 (t, J=7.4 Hz, 1H), 7.19 (d, J=7.9 Hz, 2H), 4.44 (q, J=7.1 Hz, 2H), 2.64 (s, 3H), 1.37 (q, J=7.3 Hz, 3H).

Embodiment 5 Synthesis of Roxadustat 5.1 Synthesis of Intermediate M1-A 1.1 kg (about 3.5 mol) of compound SM2 was completely dissolved in 6.6 kg of N,N-dimethylacetamide by heating to 60° C. to 70° C. 1.7 kg (about 7 mol) of sodium persulfate was dissolved in 4 kg of water and then added to the above solution, and the obtained mixture was stirred for 1 hour. The completion of the reaction was monitored by TLC. The reaction solution was cooled to room temperature. 5 kg of water was added to the solution, and the mixture was stirred and then filtered under reduced pressure, and the filter cake was dried in vacuum to obtain 1.25 kg of an off-white solid, which was intermediate M1-A, with a yield of 89.1% and a purity of 91.74% detected by HPLC.

5.2 Synthesis of Intermediate M2-A 1 kg (about 2.5 mol) of intermediate M1-A was dissolved in tetrahydrofuran (2 L) and methanol (2 L) by heating to 30° C. to 40° C. A concentrated hydrochloric acid (500 mL, hydrochloric acid with a mass fraction of 36%) was added while stirring, and the obtained mixture was stirred for 5 hours. The completion of the reaction was monitored by TLC. The reaction solution was concentrated in vacuum until a large amount of solid precipitated, filtered under reduced pressure, washed with a small amount of methanol, and drained to obtain 886 g of a white solid, which was intermediate M2-A, with a yield of 89.9% (calculated on the basis of hydrochloride salt) and a purity of 97.79% detected by HPLC.

5.3 Synthesis of Intermediate M2-A 3.00 g of intermediate M1-A was stirred in 20 mL of absolute ethanol and heated to to 40° C. After reaching the specified temperature, 5 mL of a hydrogen chloride ethanol solution (hydrogen chloride ethanol solution with a mass fraction of about 30%-35%) was added, and the mixture was stirred and reacted for 8 hours while keeping the temperature. TLC monitored the reaction to be basically complete, and the reaction was finished. The reaction solution was concentrated under reduced pressure and evaporated to dryness, and a large amount of solid was precipitated, and the mixture was filtered under reduced pressure. The filter cake was stirred and washed with 12 mL of methyl tert-butyl ether, and dried to obtain 2.52 g of an off-white solid, which was intermediate M2-A, with a yield of 85.2% (calculated on the basis of hydrochloride salt) and a purity of 97.83% detected by HPLC.

5.4 Synthesis of Intermediate M2-A 300 g of intermediate M1-A and absolute ethanol (1.2 L) were added to a 5 L reaction flask, stirred and the temperature was raised to 40 to 45° C. 500 mL of a hydrogen chloride absolute ethanol solution (hydrogen chloride ethanol solution with a mass fraction of about 30%-35%) was slowly added dropwise, and the dropwise addition was finished in about 0.5 hours; the mixture was kept the temperature at 40 to 45° C. and stirred overnight. TLC detected that the reaction of the raw materials were basically complete. The reaction solution was cooled to about 30° C., and isopropyl ether (3.3 L) was added dropwise. A white solid was precipitated, and the mixture was stirred at room temperature for 1 hour, filtered under reduced pressure. The filter cake was washed with isopropyl ether (300 mL×2 times), drained, dried in vacuum (50° C., vacuum degree ≤−0.09 MPa) for 12 hours, stopped the drying to obtain 243 g of an off-white solid, which was intermediate M2-A, with a yield of 82% (calculated on the basis of hydrochloride salt) and a purity of 99.26% detected by HPLC.

5.5 Synthesis of Intermediate M3-A 2.50 g (6.43 mmol) of intermediate M2-A, 1.03 g (19.29 mmol) of ammonium chloride, 45 mL of N,N-dimethylformamide, 5 mL of acetic acid and 0.84 g (12.86 mmol) of zinc powder were sequentially added in a 100 mL round-bottomed flask, and the mixture was magnetic stirred, heated to 50 to 60° C. and stirred for 4 hours. A sample was taken for TLC detection, and the reaction of the raw materials was basically complete. The reaction solution was cooled to 0 to 10° C. An aqueous solution of sodium chloride (15.0 g of sodium chloride and 50 mL of water) was slowly added dropwise, and the dropwise addition was finished in about 5 minutes, then the mixture was kept stirring at 0 to 10° C. for 1 hour, and then filtered under reduced pressure. The filter cake was washed with water (15 mL×3 times), drained, dried in vacuum (50 to 55° C., vacuum degree ≤0.09 MPa) for 8 hours, stopped drying to obtain M3-A, which was 1.77 g of a brown-yellow solid with a yield of 85.1% and a purity of 96.18% detected by HPLC.

5.6 Synthesis of Intermediate M3-A 100 g of intermediate M2-A, 40 g of ammonium chloride, 200 mL of acetic acid and 1800 mL of DMF were added sequentially to a 5 L reaction flask, and the obtained mixture was stirred and heated to 40 to 50° C. 8 g of zinc powder was added every half an hour, and added 6 times in total. After adding the zinc powder, the mixture was stirred for 3 hours. TLC detected that the reaction of the raw materials was basically complete, and the temperature was lowered to room temperature. A sodium chloride aqueous solution (660 g sodium chloride dissolved in 2200 mL of water) was added. After the dropwise addition, the mixture was cooled to 0 to 10° C., stirred for 1 hour, filtered under reduced pressure, and the filter cake was washed with water (100 mL×2 times), and drained. The filter cake was transferred to a 500 mL round-bottomed flask. 100 mL of acetone was added, and the mixture was cooled to to 10° C., stirred for 0.5 hours, filtered under reduced pressure, and the filter cake was washed once with 30 mL of pre-cooled acetone (0 to 10° C.), drained, and dried in vacuum (40° C., vacuum degree ≤−0.09 MPa) for 2 hours to obtain 58 g of a light yellow solid, which was M3-A, with a yield of 70% and a purity of 98.77% detected by HPLC.

5.7 Synthesis of Roxadustat 200 g of M3-A was weighed in a 20 L reactor, and 120 g of sodium glycinate and 4 L of absolute ethanol were added, and the obtained mixture was stirred evenly at room temperature. 96 g DBU was slowly added dropwise at room temperature. After the dropwise addition was completed, the mixture was heated to an internal temperature of about 78° C. for a reflux reaction for 24 hours. After the mixture was cooled, the solvent was concentrated and removed, and 4 L of water was added to stir and dissolve, and 160 g of an acetic acid was slowly added dropwise. At this time, a solid was precipitated. After stirring for 1 hour at this temperature, the heating was turned off. When the temperature in the system was lowered to room temperature, the mixture was filtered under reduced pressure. The solid filter cake was dried in vacuum (50° C., vacuum degree <−0.08 MPa) for 24 hours, and the material was collected to obtain 179 g of a crude product of roxadustat with a yield 82% and a purity of 99.73% detected by HPLC. 100 g of the crude product of roxadustat was weighed in a 5 L three-necked flask, and 1 L of purified water was added, and the obtained mixture was stirred evenly at room temperature. A sodium hydroxide aqueous solution (13 g of sodium hydroxide dissolved in 1.3 L of purified water) was slowly added dropwise at room temperature. After the dropwise addition, the reaction solution was pale yellow-green. The mixture was heated to an internal temperature of about 70° C. An acetic acid aqueous solution (26 g of acetic acid dissolved in 100 mL of purified water) was slowly added dropwise. At the same time, the pH value of the mixture was monitored. When the pH was about 7, the dropwise addition of the acetic acid solution was stopped, and a small amount of a crystalline solid was precipitated. After keeping the temperature and stirring for 1 hour, the remaining acetic acid solution was added dropwise. After the dropwise addition, the mixture was continued to be kept the temperature and stirred for 1 hour. The heating was turned off, and when the internal temperature of the system was lowered to about 45° C., the mixture was filtered under reduced pressure. The filter cake was washed with 500 mL of purified water, and the solid of the filter cake was dried in vacuum (50° C., vacuum degree <−0.08 Mpa). The materials were collected to obtain 97.36 g of a pure product of roxadustat with a yield of 97.36% and a purity of 99.91% detected by HPLC.

After a LC-MS detection, the content of compound Z3 ((4-hydroxy-14N-methylacetamido)methyl)-7-phenoxyisoquinoline-3-carbonyl)glycine in the obtained pure product of roxadustat was 14 ppm (part of the intermediate M1-A did not participate in the reduction reaction in a reduction step, and then was introduced into the condensation step to react with sodium glycine to generate compound Z3); LC-MS detection conditions: Agilent 1260/6125B quadrupole liquid chromatography mass spectrometer, chromatographic column: YMC Triart Phenyl, 4.6 mm×250 mm, 5 μm, 224 nm of a detection wavelength, mobile phase A: 20 mM of ammonium formate buffer (pH 4.5), mobile phase B: acetonitrile-water-formic acid (900:100:0.8), elution gradient: mobile phase A: 0-35 minutes: 65%→50%, 35-45 minutes: 50%→0%, 45-50 minutes: 0%, 50-51 minutes: 0%→65%, 51-60 minutes: 65%); structural identification data of compound Z3: MS: m/z=422.1360 (M−H); $^1$H-NMR (400 MHz, DMSO) δ 13.40 (s, 1H), 8.98 (t, J=5.8 Hz, 1H), 8.32 (d, J=9.1 Hz, 1H), 7.78 (d, J=2.3 Hz, 1H), 7.67-7.50 (m, 2H), 7.47 (t, J=8.0 Hz, 2H), 7.25 (t, J=7.4 Hz, 1H), 7.15 (d, J=7.9 Hz, 2H), 4.90 (s, 2H), 4.09 (d, J=5.9 Hz, 2H), 2.93 (s, 3H), 2.03 (s, 3H); $^{13}$C NMR (101 MHz, DMSO) δ 170.75, 169.76, 169.71, 158.16, 155.44, 153.74, 145.37, 130.64, 130.39, 125.39, 124.59, 123.82, 122.74, 119.77, 119.53, 111.53, 49.29, 40.83, 35.20, 21.54.

Embodiment 6 Separation, Purification and Identification of Compound I in Intermediate M2-A with a Preparative High Performance Liquid Chromatography The method described in embodiment 3.5 was repeated. 2 g of the obtained crude product of M2-A was added to water and acetonitrile (water/acetonitrile=4/1, v/v) to dissolve and dilute to 100 mL, filtered by a needle filter (nylon NY 0.45 μm-25 mm) and used for later use. The mixture was separated and purified under the following conditions, and a target fraction was collected (retention time was 6.1 min):

Instrument information: preparative high performance liquid chromatograph (equipment name: Sepfocus preparative high performance liquid chromatography), chromatographic column: YMC-Triart $C_{18}$ 7 μm 250*30 mm, mobile phase A: 10 mmol/L $NH_4HCO_3$ aqueous solution, mobile phase B: acetonitrile:isopropanol (1:1), detection wavelength: 220 nm, 254 nm, injection volume: 125 mg per needle, column temperature: room temperature, flow rate: 30 mL/min, gradient elution method is as follows:

| Time (min) | Mobile phase A | Mobile phase B |
| --- | --- | --- |
| 0 | 50% | 50% |
| 2 | 40% | 60% |
| 12 | 5% | 95% |
| 15 | 5% | 95% |
| 16 | 100% | 0% |
| 18 | 100% | 0% |

After the target fraction was concentrated into a solid by using a rotary evaporator, the solid was dried in a vacuum drying oven at 50° C. for 18 hours, and then a target substance (referred to as impurity compound I) with an HPLC purity of 98.6% and a retention time of 4.95 min was obtained. The identification data of the target substance are as follows:

$^1$H NMR (400 MHz, DMSO-$d_6$) δ=8.311 (d, J=9.2 Hz, 1H), 7.343-7.493 (m, 4H), 7.086-7.194 (m, 3H), 4.482 (s, 2H), 2.682 (s, 3H). $^{13}$C NMR (400 MHz, DMSO-$d_6$)

δ=157.049, 156.334, 134.475, 130.512, 129.319, 126.693, 126.414, 124.309, 123.911, 121.546, 119.096, 110.816, 49.346, 32.991. m/z=325.11 (M+H)⁺, m/z=347.09 (M+Na)⁺.

After analysis, its structure is

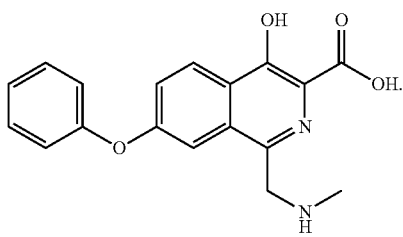

Embodiment 7 Synthesis of Compound I

7.1 Preparation of Compound I from Intermediate M1-A

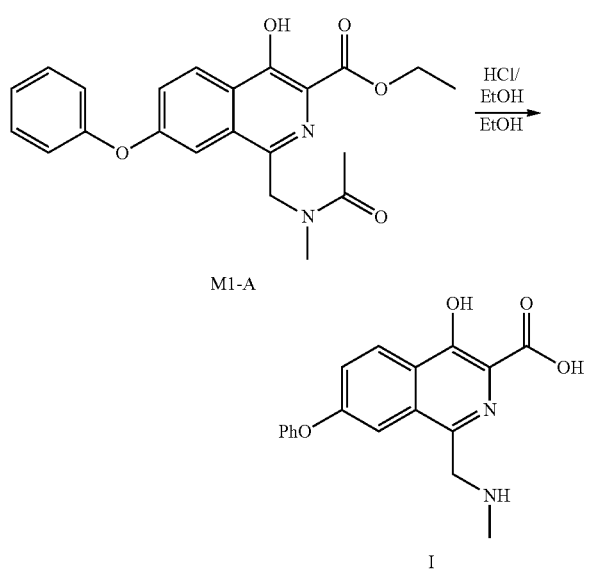

Ethyl 4-hydroxy-1-((N-methylacetamido)methyl)-7-phenoxyisoquinoline-3-carboxylate (intermediate M1-A, prepared with reference to the method of embodiment 3.1, 4 g, 0.01 mol) was added to ethanol (12 mL), then a 33% hydrogen chloride ethanol solution (8 mL) was added, and the temperature was heated to 60 to 70° C., and the mixture was stirred for about 24 hours. TLC showed that the raw material disappeared, and the heating was stopped, and the temperature was lowered to 15 to 25° C. Methyl tert-butyl ether (40 mL) was added, and a solid was precipitated. After stirring for about 1 hour, the mixture was filtered under reduced pressure to obtain 2.4 g of a white solid, namely compound I, with a yield of 67% (calculated on the basis of hydrochloride salt); a HPLC purity was greater than 98%, and the retention time was 4.95 min, which was consistent with the retention time of impurity compound I obtained in embodiment 6.

MS (ESI) m/z: m/z=325.11 (M+H)⁺, m/z=347.09 (M+Na)⁺.

¹H-NMR (400 MHz, DMSO-d₆): δ=11.699 (s, 1H), 9.593 (s, 2H), 8.411 (d, J=8.8 Hz, 1H), 7.687 (s, 1H), 7.575-7.614 (m, 1H), 7.478 (t, J=8.8 Hz, 2H), 7.262 (t, J=7.6 Hz, 1H), 7.175 (d, J=8.8 Hz, 2H), 4.675 (s, 2H), 2.730 (s, 3H).

7.2 Preparation of Compound I from Intermediate 28

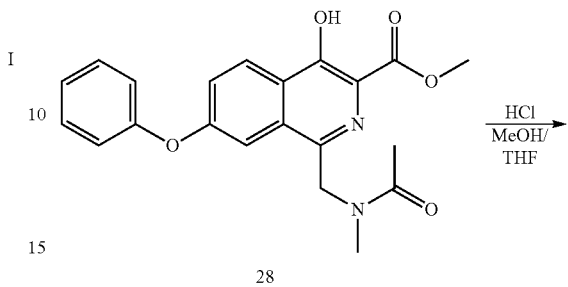

Methyl 4-hydroxy-1-((N-methylacetamido)methyl)-7-phenoxyisoquinoline-3-carboxylate (intermediate 28, prepared with reference to the method of embodiment 1.2, 4 g, mol) was added to methanol (10 mL) and tetrahydrofuran (20 mL), then a 36% concentrated hydrochloric acid (15 mL) was added, and the temperature was heated to 60 to 70° C. and the mixture was stirred for about 24 hours. TLC showed that the raw material disappeared, the heating was stopped, and the temperature was lowered to 15 to 25° C. A solid was precipitated. After stirring for about 1 hour, the mixture was filtered under reduced pressure to obtain 1.6 g of a white solid, namely compound I, with a yield of 44% (calculated on the basis of hydrochloride salt). After identification, the ¹H-NMR and mass spectrometry data of compound I were the same as those of embodiment 7.1. The HPLC purity was greater than 97%, and the retention time was 4.95 min, which was consistent with the retention time of the impurity compound I obtained in embodiment 6.

7.3. Preparation of Compound I from Intermediate M1-F

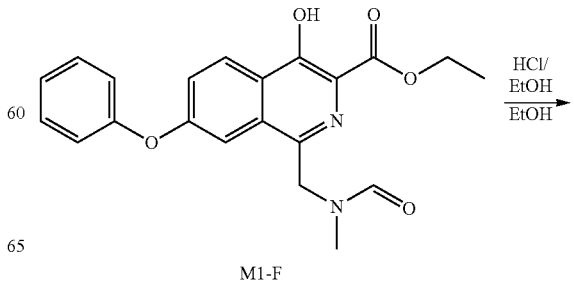

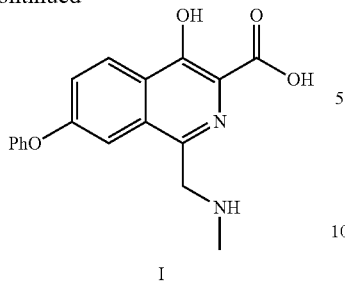

Ethyl 4-hydroxy-14N-methylformamido)methyl)-7-phenoxyisoquinoline-3-carboxylate (intermediate M1-F, prepared with reference to the method of embodiment 3.4, 4 g, 0.01 mol) was added to ethanol (12 mL), then a 33% hydrogen chloride ethanol solution (8 mL) was added, and the temperature was heated to 60 to 70° C. and the mixture was stirred for about 24 hours. TLC showed that the raw material disappeared, and the heating was stopped, and the temperature was lowered to 15 to 25° C. Isopropyl acetate (50 mL) was added, and a solid was precipitated. After stirring for about 1 hour, the mixture was filtered under reduced pressure to obtain 2.1 g of a white solid, namely compound I, with a yield of 58% (calculated on the basis of hydrochloride salt). After identification, the 41-NMR and mass spectrometry data of compound I were the same as those of embodiment 7.1. The HPLC purity was greater than 97%, and the retention time was 4.95 min, which was consistent with the retention time of the impurity compound I obtained in embodiment 6.

Embodiment 8 Refining Method of Intermediate and Content Control of Compound I 8.1 Refining Method of Intermediate M2-A The preparation method described in embodiment 3.5 was repeated. 6.8 g (0.018 mol) of intermediate M1-A was used as raw material to prepare 5.6 g of a crude product of M2-A (white solid) with a purity of 98.40% detected by HPLC, 1.4% of the content of target impurity (compound I, retention time was 4.95 min), and a crude product yield of 92% (calculated on the basis of hydrochloride salt).

Ethanol (2 mL) and isopropyl acetate (10 mL) were added to 2.8 g of the obtained crude product of M2-A, stirred at 10 to 25° C. for about 2 hours, and filtered under reduced pressure to obtain 1.5 g of a white solid, which was a refined product of intermediate M2-A. The refined yield was about 54% (calculated on the basis of hydrochloride salt), the purity was 99.0% detected by HPLC, the main impurity was compound I (retention time was 4.95 min), and the content was 0.8%.

8.2 Synthesis and Refining Method of Intermediate M3-A 1.5 g of the refined product of intermediate M2-A obtained in embodiment 8.1 (purity 99.0%, impurity content of compound I 0.8%) was dissolved in 15 mL of acetic acid, then 1.56 g of zinc powder was added, and the mixture was heated to 50° C. to 60° C., stirred for 6 hours. The completion of the reaction was monitored by TLC, and the mixture was filtered. A mixed solvent of dichloromethane (12 mL) and methanol (6 mL) was added to wash the filter cake. The filtrates were combined and concentrated to obtain an off-white solid. The obtained off-white solid was added to 10 mL of acetone and stirred at 45 to 55° C. for about 1 hour. The mixture was cooled to 15 to 25° C., stirred for 1 hour, and filtered under reduced pressure to obtain 0.96 g of a refined product of M3-A with a yield of 70% and a purity of 98.9% detected by HPLC, wherein the content of impurity compound II (retention time was 6.8 min) was 0.05%.

Structural identification data for impurity compound II:
MS (ESI) m/z: 294.0767 (M–H)$^+$;
H-NMR (DMSO-d$_6$, 400 Hz): δ=8.420 (d, J=8.8 Hz, 1H), 7.749 (s, 1H), 7.637-7.664 (m, 1H), 7.491 (t, J=8 Hz, 2H), 7.276 (t, J=7.2 Hz, 1H), 7.211 (d, J=7.6 Hz, 2H), 2.865 (s, 3H); C NMR (DMSO-d6, 400 Hz): δ=166.09, 161.97, 158.81, 155.17, 142.78, 130.59, 130.48, 127.96, 126.67, 124.88, 124.82, 119.61, 114.26, 113.75, 16.61.

8.3 Synthesis of Roxadustat 0.9 g of the refined product of intermediate M3-A (HPLC purity 98.9%, impurity compound II content was 0.05%) obtained in embodiment 8.2 was added to 9 mL of ethanol, and 0.84 g of sodium glycinate was added, and the mixture was heated to 105° C. to 115° C. in a pressure-resistant container and stirred for 8 hours. The reaction solution was cooled to room temperature, filtered under reduced pressure, washed with a small amount of methanol, and drained to obtain a crude product of a roxadustat sodium salt. The crude product of the roxadustat sodium salt was dissolved in 15 mL of water. 6 mL of ethyl acetate was added for extraction. The pH of the aqueous phase was adjusted to less than 7 by acetic acid. A large amount of solid was precipitated, filtered under reduced pressure. The filter cake was washed with water and drained, dried in vacuum to obtain 0.84 g of a finished product of roxadustat with a yield of 86% and a purity of 99.81%, and the content of impurity compound II (retention time was 6.8 min) was 0.03%.

Comparative Embodiment 1

Reaction of Hydroxyisoquinoline with Sodium Persulfate in N,N-Dimethylacetamide

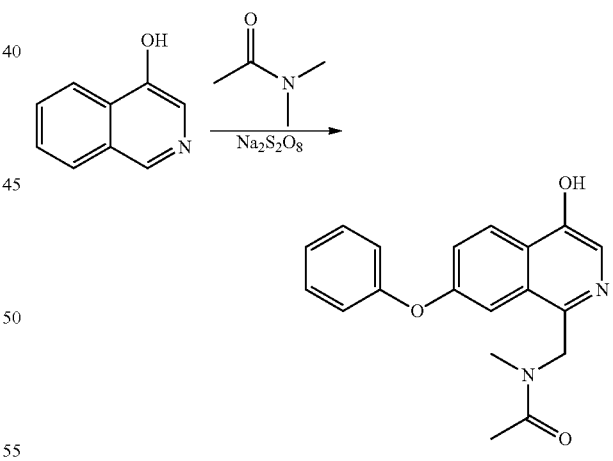

1.45 g (0.01 mol) of hydroxyisoquinoline and 14.5 g (about 0.2 mol) of N,N-dimethylacetamide were successively added to a 50 mL three-necked flask. After stirring and dissolving, 4.76 g (0.02 mol) of sodium persulfate was dissolved in 9.52 g (about 0.53 mol) of water then added dropwise to the above solution, and the obtained mixture was heated to 70° C. and stirred for 1 hour. TLC detected that most of the raw materials remained, and no major products were produced. After heating to 80° C. and stirring for 2 hours, TLC detected that most of the raw materials still remained, and no major products were produced.

HPLC: stirring at 70° C. for 1 hour, leaving 85.64% of raw materials; stirring at 80° C. for 2 hours, leaving 75.01% of raw materials; MS (ESI) m/z: 146.0 [m+1]⁺ (raw material molecular weight), and no molecular weight of the product was detected.

What is claimed is:

1. A synthesis method of compound M1, and the method comprises the following steps: carrying out a reaction as shown below between compound SM and compound SM-A under the action of an oxidizing agent;

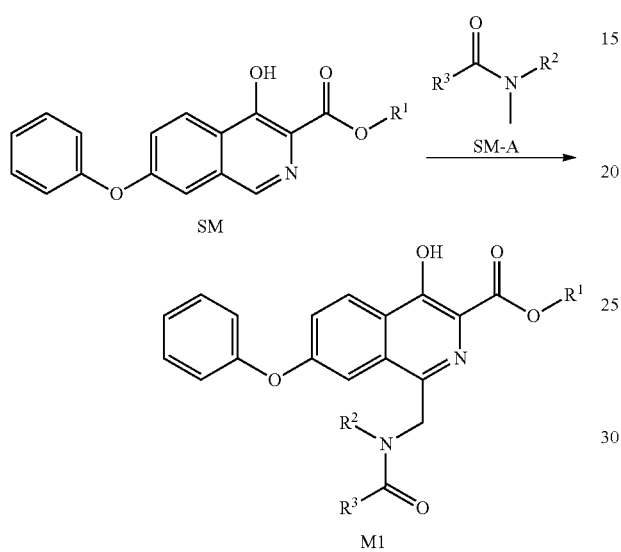

$R^1$ is H, $C_1$-$C_4$ alkyl or $C_6$-$C_{10}$ aryl;
$R^2$ is H or methyl;
$R^3$ is H, $C_1$-$C_4$ alkyl, $C_4$-$C_6$ cycloalkyl or $C_6$-$C_{10}$ aryl;
wherein, the $C_1$-$C_4$ alkyl, the $C_6$-$C_{10}$ aryl and the $C_4$-$C_6$ cycloalkyl are optionally substituted by 1, 2 or 3 R, and each R is independently halogen, hydroxyl, amino, $C_1$-$C_4$ alkyl, $C_1$-$C_4$ alkoxy, mono($C_1$-$C_4$ alkyl)amino, di($C_1$-$C_4$ alkyl)amino, cyano or nitro.

2. The synthesis method of compound M1 as claimed in claim 1, wherein,
$R^1$ is H, methyl, ethyl, n-propyl, isopropyl, n-butyl, isobutyl, sec-butyl, tert-butyl, phenyl or naphthyl;
or, $R^3$ is H, methyl, ethyl, n-propyl, isopropyl, n-butyl, isobutyl, sec-butyl, tert-butyl, cyclobutyl, cyclopentyl, cyclohexyl, phenyl or naphthyl;
or, the oxidizing agent is a persulfate oxidizing agent, a peroxide oxidizing agent or a mixture thereof;
or a molar ratio of the compound SM-A to the compound SM is greater than 1:15;
or a temperature of the reaction is 30° C. to 100° C.

3. The synthesis method of compound M1 as claimed in claim 1, wherein,
compound SM-A is

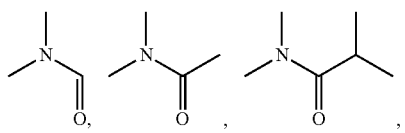

-continued

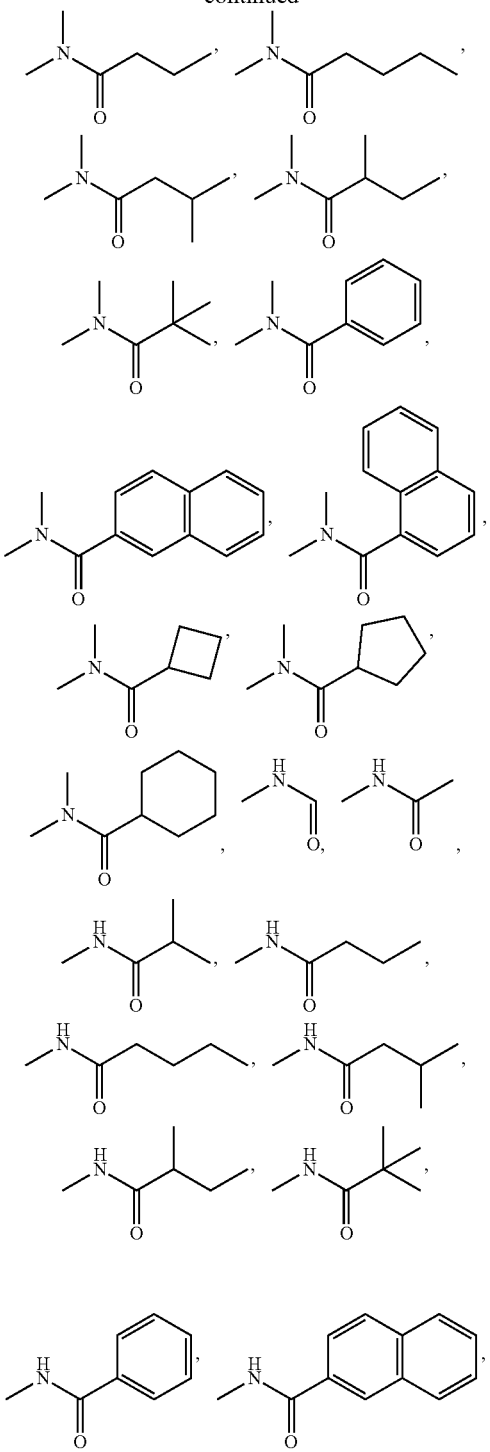

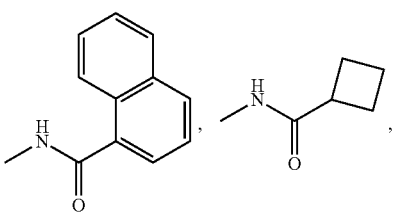

-continued

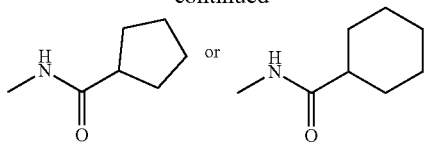

optionally substituted by 1, 2 or 3 R;

or, when the compound SM-A is a liquid, the compound SM-A serves as a reaction raw material and a solvent simultaneously; when the compound SM-A is a solid, the synthesis of the compound M1 is carried out in the presence of a solvent; the solvent is a chlorinated hydrocarbon solvent, an ether solvent or a mixture thereof, the solvent is dichloromethane, tetrahydrofuran, dioxane or a mixture thereof.

4. The synthesis method of compound M1 as claimed in claim 3, wherein, compound SM is

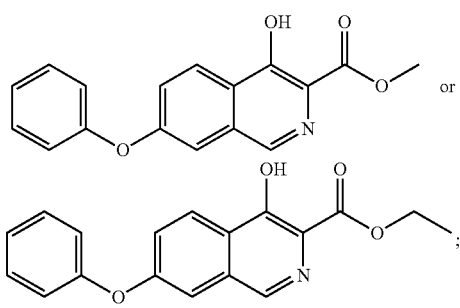

or, compound SM-A is

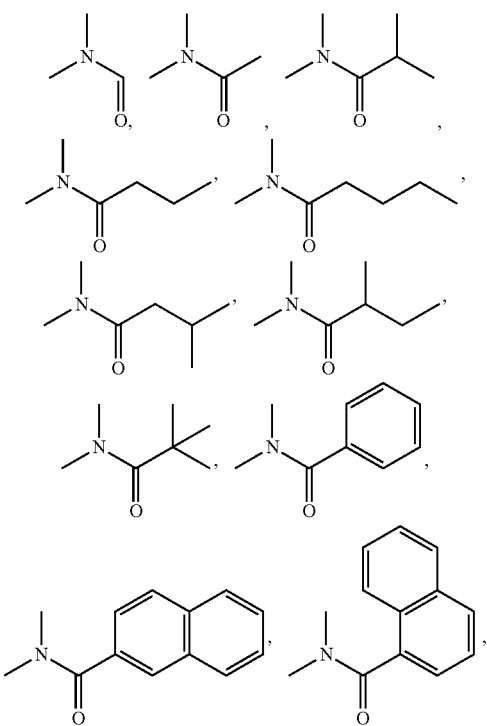

-continued

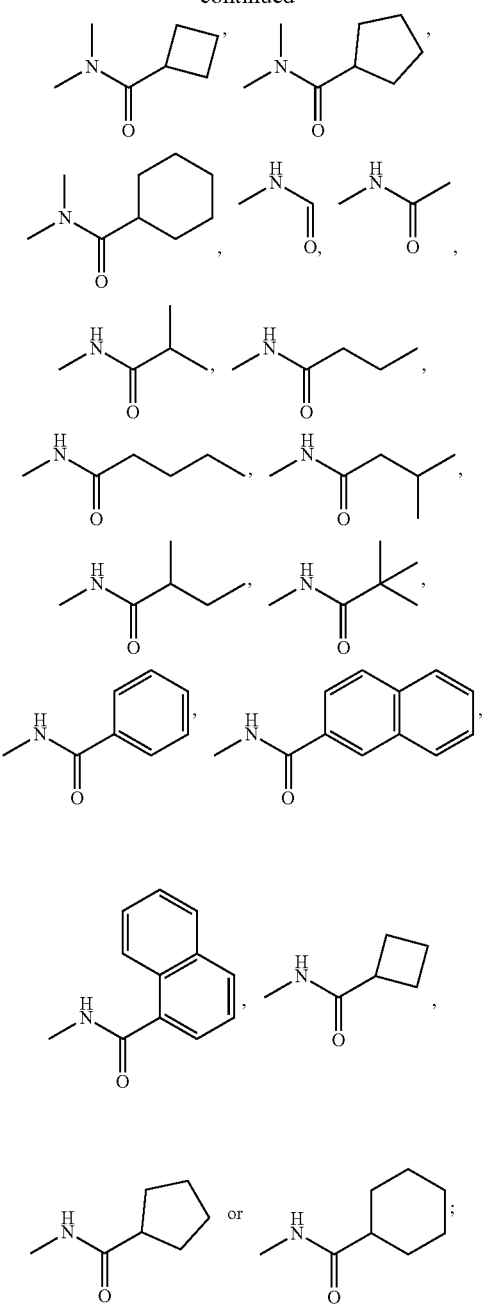

or, compound M1 is

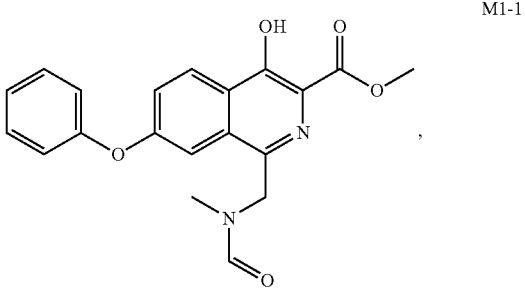

M1-1

28

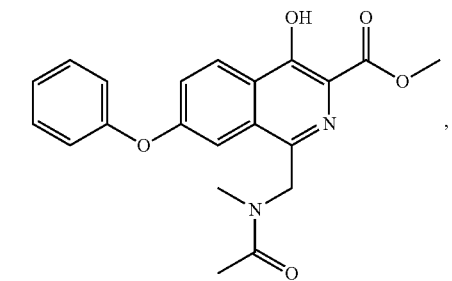

M1-2

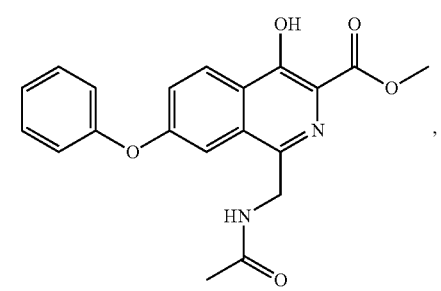

M1-F

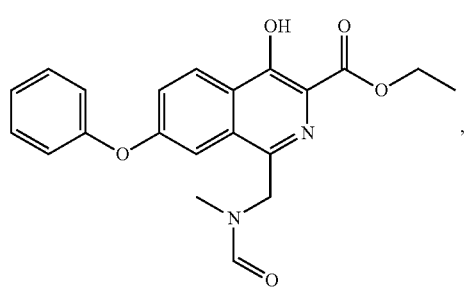

M1-A

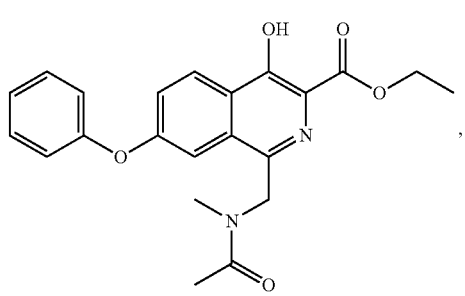

M1-C

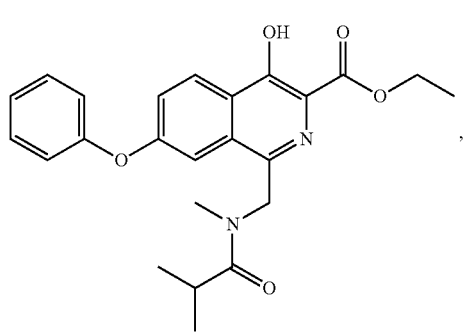

M1-D

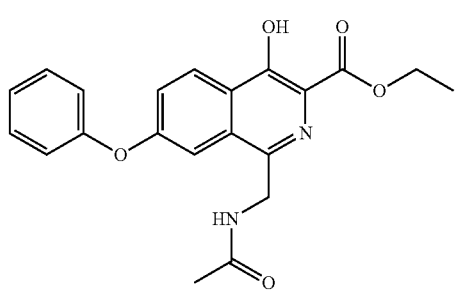

or

M1-E

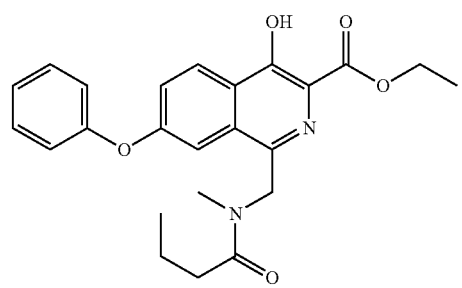

5. A synthesis method of compound M2, and the method comprises the following steps: carrying out a reaction as shown below on compound M1 under the action of an acid; wherein the synthesis method of compound M2 comprises the synthesis method of compound M1 as defined in claim 1; m

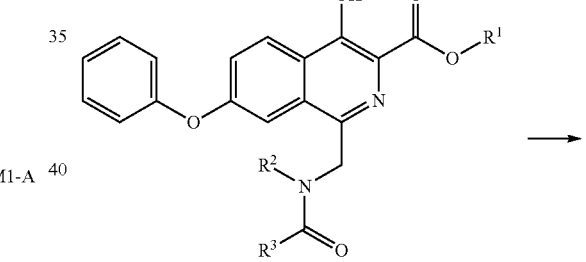

M1

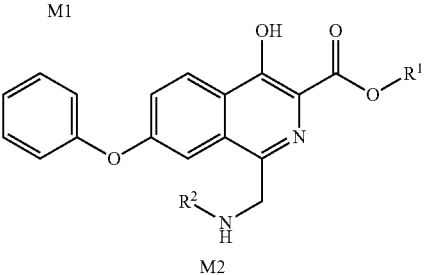

M2

$R^1$ is H, $C_1$-$C_4$ alkyl or $C_6$-$C_{10}$ aryl;
$R^2$ is H or methyl;
$R^3$ is H, $C_1$-$C_4$ alkyl, $C_4$-$C_6$ cycloalkyl or $C_6$-$C_{10}$ aryl;
wherein, the $C_1$-$C_4$ alkyl, the $C_6$-$C_{10}$ aryl and the $C_4$-$C_6$ cycloalkyl are optionally substituted by 1, 2 or 3 R, and each R is independently halogen, hydroxyl, amino, $C_1$-$C_4$ alkyl, $C_1$-$C_4$ alkoxy, mono($C_1$-$C_4$ alkyl)amino, di($C_1$-$C_4$ alkyl)amino, cyano or nitro.

6. The synthesis method of compound M2 as claimed in claim 5, wherein, in the synthesis method of compound M2, the acid is an inorganic acid, an organic acid or a mixture thereof;

or, in the synthesis method of compound M2, the solvent is an ether solvent, an alcohol solvent, an amide solvent, a sulfoxide solvent or a mixture thereof;

or, in the synthesis method of compound M2, a temperature of the reaction is 25° C. to 50° C.

7. The synthesis method of compound M2 as claimed in claim 6, wherein, in the synthesis method of compound M2, the solvent in the reaction is a single solvent or a mixture of two or more solvents.

8. A synthesis method of compound M3, and the method comprises the following steps: carrying out a reaction as shown below on compound M2 under the presence of a hydrogen source; wherein the synthesis method of compound M3 comprises the synthesis method of compound M2 as defined in claim 5;

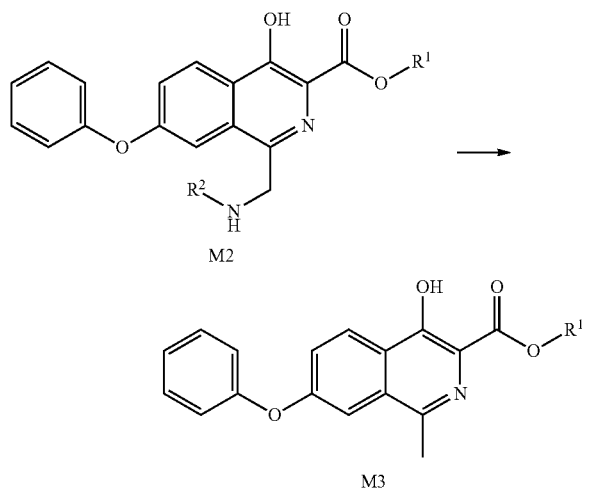

$R^1$ is H, $C_1$-$C_4$ alkyl or $C_6$-$C_{10}$ aryl;

$R^2$ is H or methyl;

wherein, the $C_1$-$C_4$ alkyl and the $C_6$-$C_{10}$ aryl are optionally substituted by 1, 2 or 3 R, and each R is independently halogen, hydroxyl, amino, $C_1$-$C_4$ alkyl, $C_1$-$C_4$ alkoxy, mono($C_1$-$C_4$ alkyl)amino, di($C_1$-$C_4$ alkyl)amino, cyano or nitro.

9. The synthesis method of compound M3 as claimed in claim 8, wherein, in the synthesis method of compound M3, the hydrogen source is a metal element/a hydrogen donor.

10. The synthesis method of compound M3 as claimed in claim 8, wherein, in the synthesis method of compound M3, compound M2 is

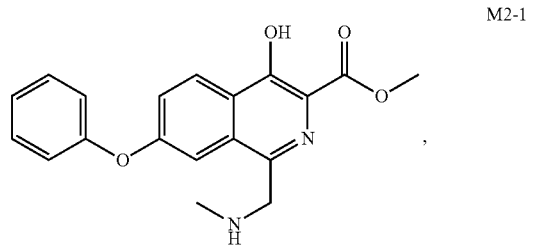

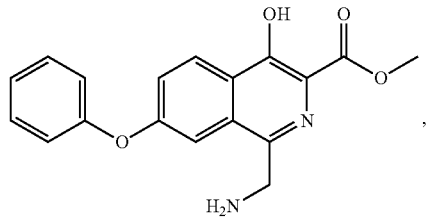

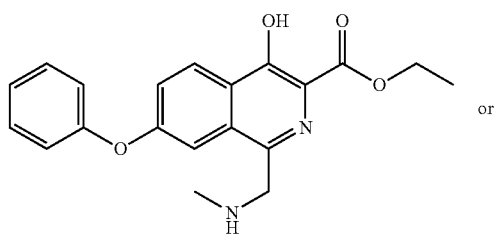

or

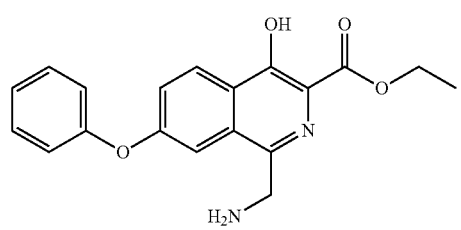

11. A synthesis method of roxadustat, and the method comprises the following steps:

carrying out a reaction as shown below between compound M3 and $NH_2CH_2COOR^a$; wherein the synthesis method of roxadustat comprises the synthesis method of compound M3 as defined in claim 8;

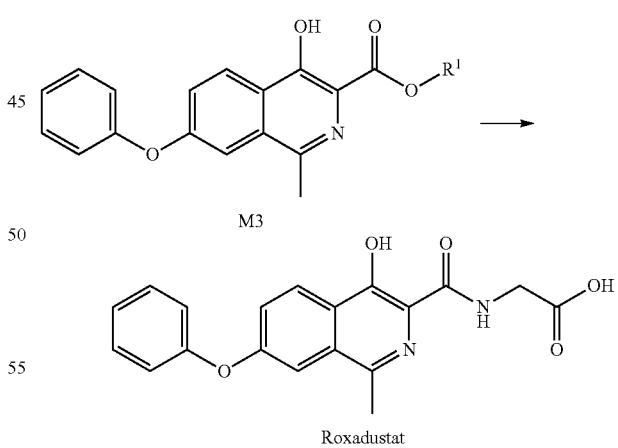

wherein, $R^a$ is H or Na; $R^1$ is H, $C_1$-$C_4$ alkyl or $C_6$-$C_{10}$ aryl;

the $C_1$-$C_4$ alkyl and the $C_6$-$C_{10}$ aryl are optionally substituted by 1, 2 or 3 R, and each R is independently halogen, hydroxyl, amino, $C_1$-$C_4$ alkyl, $C_1$-$C_4$ alkoxy, mono($C_1$-$C_4$ alkyl)amino, di($C_1$-$C_4$ alkyl)amino, cyano or nitro.

12. The synthesis method of compound M1 as claimed in claim 2, wherein,
the persulfate oxidizing agent is alkali metal persulfate, alkaline earth metal persulfate or a mixture thereof,
or, the peroxide oxidizing agent is R'''—O—O—R''; wherein R''' and R'' are independently H, $C_1$-$C_4$ alkyl or benzoyl optionally substituted by 1, 2 or 3 halogens;
or, a molar ratio of the compound SM to the oxidizing agent is 1:1.5-1:3;
or, a molar ratio of the compound SM-A to the compound SM is greater than 5:1, greater than 10:1, greater than 20:1, greater than 40:1, or greater than 50:1;
or, a temperature of the reaction is 50° C. to 80° C.

13. The synthesis method of compound M2 as claimed in claim 6, wherein,
in the synthesis method of compound M2, the inorganic acid is a hydrochloric acid, a sulfuric acid, a phosphoric acid or a mixture thereof;
or, in the synthesis method of compound M2, the organic acid is an acetic acid, a trifluoroacetic acid or a mixture thereof;
or, in the synthesis method of compound M2, the ether solvent is tetrahydrofuran, dioxane or a mixture thereof;
or, in the synthesis method of compound M2, the alcohol solvent is methanol, ethanol, isopropanol or a mixture thereof;
or, in the synthesis method of compound M2, the amide solvent is N,N-dimethylformamide, N,N-dimethylacetamide or a mixture thereof; the sulfoxide solvent is DMSO.

14. The synthesis method of compound M3 as claimed in claim 9, wherein, the metal element is a zinc powder, an iron powder or a mixture thereof; the hydrogen donor is any one of an acid, ammonium formate, ammonium chloride, or a mixture of the acid and ammonium chloride, or a mixture of the acid and ammonium formate.

15. The synthesis method of compound M3 as claimed in claim 14, wherein, in the synthesis method of compound M3, the metal element is the zinc powder.

16. The synthesis method of compound M3 as claimed in claim 14, wherein, when the hydrogen donor is the acid, the acid is an inorganic acid, an organic acid or a mixture thereof.

17. The synthesis method of compound M3 as claimed in claim 14, wherein, when the hydrogen donor is the mixture of the acid and ammonium chloride, or the mixture of the acid and ammonium formate, the acid is an inorganic acid, an organic acid or a mixture thereof.

18. A compound M1, a compound M2 or a salt thereof:

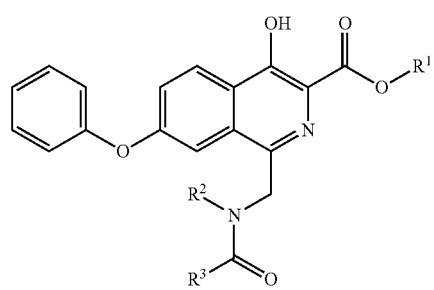

M1

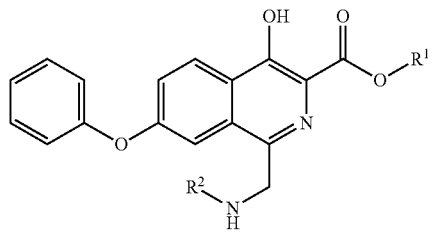

M2 wherein,
$R^1$ is H, $C_1$-$C_4$ alkyl or $C_6$-$C_{10}$ aryl;
$R^2$ is H or methyl;
$R^3$ is H, $C_1$-$C_4$ alkyl, $C_4$-$C_6$ cycloalkyl or $C_6$-$C_{10}$ aryl;
wherein, the $C_1$-$C_4$ alkyl, the $C_0$-$C_{10}$ aryl and the $C_4$-$C_6$ cycloalkyl are optionally substituted by 1, 2 or 3 R, and each R is independently halogen, hydroxyl, amino, $C_1$-$C_4$ alkyl, $C_1$-$C_4$ alkoxy, mono($C_1$-$C_4$alkyl)amino, di($C_1$-$C_4$ alkyl)amino, cyano or nitro.

19. The compound M1, the compound M2 or the salt thereof as claimed in claim 5, wherein, the compound M1 is

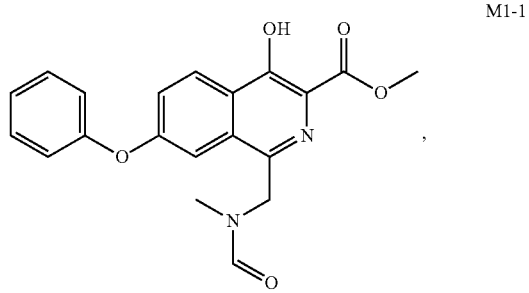

M1-1

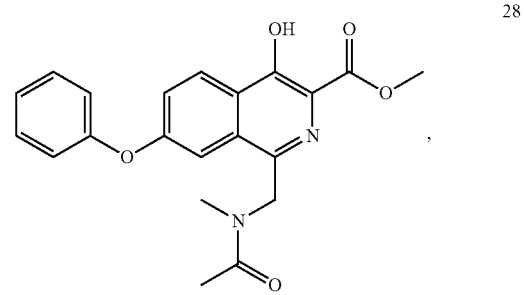

28

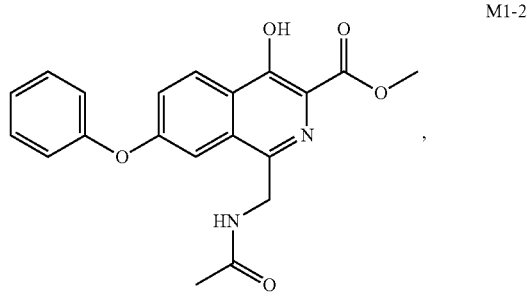

M1-2

M1-F

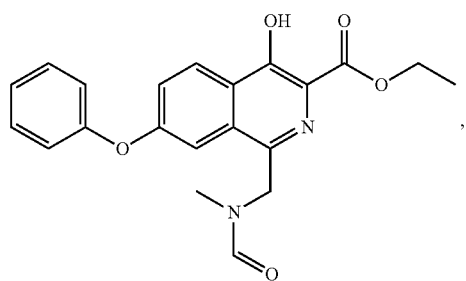

,

M1-A

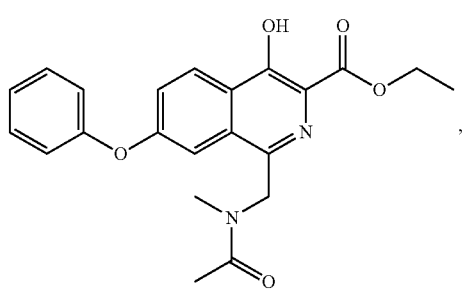

,

M1-C

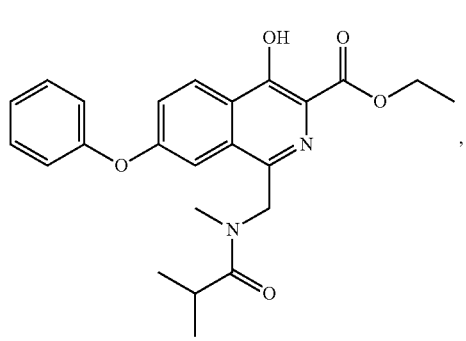

,

M1-D

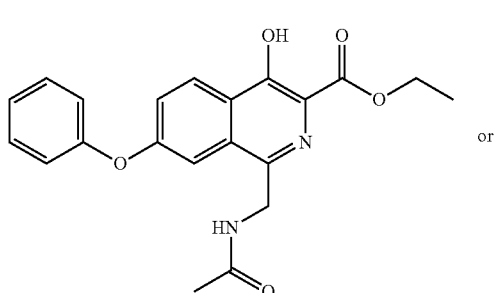 or

M1-E

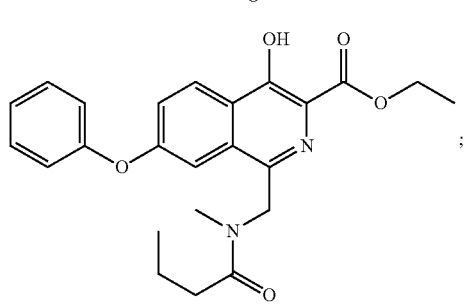 ;

or the compound M2 is

M2-1

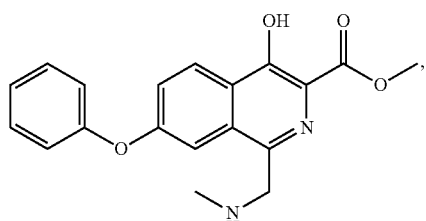 ,

M2-2

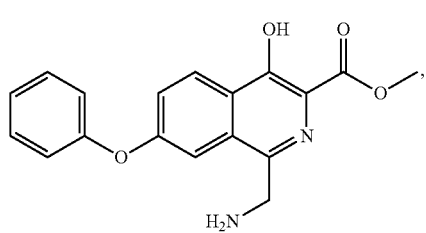 ,

M2-A

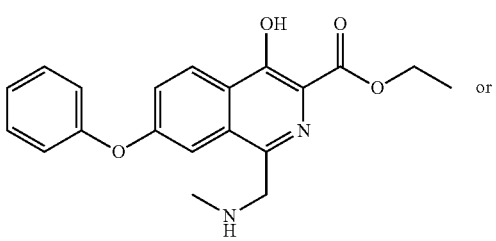 or

M2-D

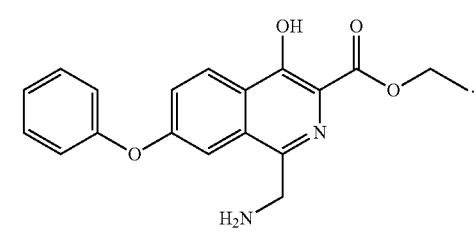 .

20. The synthesis method of compound M1 as claimed in claim 12, wherein, the alkali metal persulfate is sodium persulfate, potassium persulfate, potassium peroxymonosulfate composite salt or a mixture thereof, or, the alkaline earth metal persulfate is magnesium persulfate;

or, the peroxide oxidizing agent is hydrogen peroxide, peracetic acid, peroxytrifluoroacetic acid, benzoyl peroxide, tert-butyl hydroperoxide, di-tert-butyl peroxide or a mixture thereof;

or, a molar ratio of the compound SM to the oxidizing agent is 1:2;

or, a temperature of the reaction is 65° C. to 70° C.

* * * * *